(12) United States Patent
Hauptmann et al.

(10) Patent No.: US 7,264,944 B1
(45) Date of Patent: *Sep. 4, 2007

(54) TNF RECEPTORS, TNF BINDING PROTEINS AND DNAS CODING FOR THEM

(75) Inventors: Rudolf Hauptmann, Ebreichsdorf (AT); Adolf Himmler, Vienna (AT); Ingrid Maurer-Fogy, Vienna (AT); Christian Stratowa, Vienna (AT)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/525,998

(22) Filed: Mar. 15, 2000

Related U.S. Application Data

(60) Continuation of application No. 08/383,676, filed on Feb. 1, 1995, now Pat. No. 6,294,352, which is a continuation of application No. 08/153,287, filed on Nov. 17, 1993, now abandoned, which is a continuation of application No. 07/821,750, filed on Jan. 2, 1992, now abandoned, which is a division of application No. 07/511,430, filed on Apr. 20, 1990, now abandoned.

(30) Foreign Application Priority Data

| Apr. 21, 1989 | (DE) | ................. 39 13 101 |
| Jun. 21, 1989 | (DE) | ................. 39 20 282 |
| Apr. 6, 1990 | (EP) | ................. 90106624 |

(51) Int. Cl.
*C12N 15/00* (2006.01)
*C12N 15/09* (2006.01)

(52) U.S. Cl. ............... 435/69.1; 435/320.1; 435/252.3; 435/363; 536/23.5; 530/350

(58) Field of Classification Search ............... 530/350; 536/23.5; 435/69.1, 320.1
See application file for complete search history.

(56) References Cited

U.S. PATENT DOCUMENTS

| 4,289,690 | A |   | 9/1981 | Pestka et al. |
| 4,560,649 | A |   | 12/1985 | Saxena et al. |
| 4,578,335 | A |   | 3/1986 | Urdal et al. |
| 4,609,546 | A |   | 9/1986 | Hiratani |
| 4,675,285 | A |   | 6/1987 | Clark et al. |
| 4,789,658 | A |   | 12/1988 | Yoshimoto et al. |
| 4,847,325 | A | * | 7/1989 | Shadle et al. ............... 525/54.1 |
| 4,902,502 | A |   | 2/1990 | Nitecki et al. |
| 4,904,584 | A |   | 2/1990 | Shaw |
| 4,931,544 | A |   | 6/1990 | Katre et al. |
| 4,935,233 | A |   | 6/1990 | Bell et al. |
| 4,966,888 | A |   | 10/1990 | Saxena et al. |
| 5,089,261 | A |   | 2/1992 | Nitecki et al. |
| 5,116,964 | A |   | 5/1992 | Capon |
| 5,136,021 | A |   | 8/1992 | Dembinski et al. |
| 5,153,265 | A |   | 10/1992 | Shandle et al. |
| 5,162,430 | A |   | 11/1992 | Rhee et al. |
| 5,214,131 | A |   | 5/1993 | Sano et al. |
| 5,252,714 | A |   | 10/1993 | Harris et al. |
| 5,344,915 | A |   | 9/1994 | LeMaire et al. |
| 5,359,037 | A |   | 10/1994 | Wallach et al. |
| 5,382,657 | A |   | 1/1995 | Karasiewicz et al. |
| 5,395,760 | A |   | 3/1995 | Smith et al. |
| 5,478,925 | A |   | 12/1995 | Wallach et al. |
| 5,512,544 | A |   | 4/1996 | Wallach et al. |
| 5,605,690 | A |   | 2/1997 | Jacobs et al. |
| 5,610,279 | A |   | 3/1997 | Brockhaus et al. |
| 5,633,145 | A |   | 5/1997 | Feldmann et al. |
| 5,695,953 | A | * | 12/1997 | Wallach et al. ............ 435/69.1 |
| 5,712,155 | A |   | 1/1998 | Smith et al. |
| 5,808,029 | A |   | 9/1998 | Brockhaus et al. |
| 5,811,261 | A | * | 9/1998 | Wallach et al. ............ 435/69.1 |
| 5,863,786 | A |   | 1/1999 | Feldmann et al. |
| 6,294,352 | B1 |   | 9/2001 | Hauptmann et al. |

FOREIGN PATENT DOCUMENTS

| DE | 03913101.7 | 4/1989 |
| DE | 03920282.8 | 6/1989 |
| DE | 03910323 A1 | 10/1989 |

(Continued)

OTHER PUBLICATIONS

Wang et al., Nuc. Acids Res. 27: 4609-4618, 1999; p. 4617.*
Kaufman et al, Blood 94: 3178-3184, 1999.*
Wigley et al. Reprod Fert Dev 6: 585-588, 1994.*
Campbell et al. Theriology 47(1): 63-72, 1997.*
Phillips, A., J Pharm Pharmacology 53: 1169-1174, 2001.*
Aggarwal et al., "Characterization of receptors for human tumour necrosis factor and their regulation by gamma-interferon," Nature 318:665-67 (1985).
Baglioni et al., "Binding of human tumor necrosis factor to high affinity receptors on HeLa and lymphoblastoid cells sensitive to growth inhibition," J. Biol. Chem. 260:13395-97 (1985).

(Continued)

*Primary Examiner*—Eileen B. O'Hara
(74) *Attorney, Agent, or Firm*—McDonnell Boehnen Hulbert & Berghoff LLP

(57) ABSTRACT

The present invention provides DNA sequences coding for a TNF-binding protein and for the TNF receptor of which this protein constitutes the soluble domain. The DNA sequences can be used for preparing recombinant DNA molecules in order to produce TNF-binding protein and TNF receptor. Recombinant TNF-binding protein is used in pharmaceutical preparations for treating indications in which TNF has a harmful effect. With the aid of the TNF receptor or fragments thereof or with the aid of suitable host organisms transformed with recombinant DNA molecules containing the DNA which codes for the TNF receptor or fragments or modifications thereof, it is possible to investigate substances for their interaction with the TNF receptor and/or for their effect on the biological activity of TNF.

13 Claims, 22 Drawing Sheets

FOREIGN PATENT DOCUMENTS

| | | |
|---|---|---|
| EP | 0154316 A2 | 9/1985 |
| EP | 0162699 | 11/1985 |
| EP | 0247860 A2 | 12/1987 |
| EP | 0259863 A2 | 3/1988 |
| EP | 0308378 | 3/1989 |
| EP | 0154316 B1 | 9/1989 |
| EP | 0334165 A2 | 9/1989 |
| EP | 0225579 A3 | 11/1989 |
| EP | 0393438 A2 | 10/1990 |
| EP | 0398327 A1 | 11/1990 |
| EP | 0412486 | 2/1991 |
| EP | 0417563 A2 | 3/1991 |
| EP | 0418014 A1 | 3/1991 |
| EP | 0422339 | 4/1991 |
| EP | 0433900 | 6/1991 |
| EP | 0512528 A2 | 11/1992 |
| EP | 0526905 A2 | 2/1993 |
| GB | 2218101 | 11/1989 |
| GB | 2246569 A | 2/1992 |
| WO | WO92/01002 | 2/1990 |
| WO | WO90/13575 | 11/1990 |
| WO | WO91/03553 | 3/1991 |
| WO | WO92/07076 | 4/1992 |
| WO | WO92/13095 | 8/1992 |
| WO | WO92/15682 | 9/1992 |
| WO | WO92/16221 | 10/1992 |
| WO | WO93/01474 | 1/1993 |
| WO | WO94/06476 | 3/1994 |

OTHER PUBLICATIONS

Bakouche et al., "Plasma membrane-associated tumor necrosis factor. A non-integral membrane protein possibly bound to its own receptor," J. Immunol. 140:1142-47 (1988).

Beutler et al., "Passive immunization against cachectin/tumor necrosis factor protects mice from lethal effect of endotoxin," Science 229:869-71 (1985).

Binkert et al., "Cloning, sequence analysis and expression of a cDNA encoding a novel insulin-like growth factor binding protein (IGFBP-2)," EMBO J. 8:2497-502 (1989).

Bowie et al., "Deciphering the message in protein sequences: tolerance to amino acid substitutions," Science 247:1306-10 (1990).

Brennan et al., "Inhibitory effect of TNF alpha antibodies on synovial cell interleukin-1 production in rheumatoid arthritis," Lancet 2:244-47 (1989).

Brockhaus, M. et al., Proc. Natl. Acad. Sci. USA 87:3127-3131 (1990).

Capaldi et al., "Changes in order of migration of polypeptides in complex III and cytochrome C oxidase under different conditions of SDS polyacrylamide gel electrophoresis," Biochem. Biophys. Res. Commun. 74:425-33 (1977).

Carlino et al., Use of a Sensitive Receptor Binding Assay to Discriminate Between Full-Length and Truncated Human Recombinant TNF.

Colletti et al., "The production of tumor necrosis factor alpha and the development of a pulmonary capillary injury following hepatic ischemia/reperfusion," Transplantation 49:268-72 (1990).

Creasy, A. et al., Proc. Natl. Acad. Sci. USA 84:3293-3297 (1987).

Dayer et al., "Purification and Characterization of Human Tumor Necrosis Factor a Inhibitor," Chemical Abstracts 113(38760n):454 (1990).

Engelmann et al., "A tumor necrosis factor-binding protein purified to homogeneity from human urine protects cells from tumor necrosis factor toxicity," J. Biol. Chem. 264:11974-80 (1989).

Engelmann et al., "Antibodies to a soluble form of a tumor necrosis factor (TNF) receptor have TNF-like activity,," J. Biol. Chem. 265:14497-504 (1990).

Espevik et al., "Characterization of binding and biological effects of monoclonal antibodies against a human tumor necrosis factor receptor," J. Exp. Med. 171:415-26 (1990).

Evans, "The steroid and thyroid hormone receptor superfamily," Science 240:889-95 (1988).

Frohman et al., "Rapid production of full-length cDNAs from rare transcripts: amplification using a single gene-specific oligonucleotide primer," Proc. Natl. Acad. Sci. U. S. A. 85:8998-9002 (1988).

Gatanaga et al., Purification and characterization of an inhibitor (soluble tumor necrosis factor receptor) for tumor necrosis factor and lymphotoxin . . . , Proc. Natl. Acad. Sci. USA 87:8781-8784 (1990).

Goodson et al., "Site-Directed Pegylation of Recombinant Interleukin-2 At Its Glycosylation Site," BioTechnology 8:343-346 (1990).

Goodwin et al., "Molecular cloning and expression of the type 1 and type 2 murine receptors for tumor necrosis factor," Mol. Cell. Biol. 11:3020-26 (1991).

Gray et al., "Cloning of human tumor necrosis factor (TNF) receptor cDNA and expression of recombinant soluble TNF-binding protein," Proc. Natl. Acad. Sci. U. S. A. 87:7380-84 (1990).

Grizzard et al., "Affinity-labeled somatomedin-C receptors and binding proteins from the human fetus," J. Clin. Endocrinol. Metab. 58:535-43 (1984).

Hale et al., "Cytokines and Their Receptors: From Clonal to Clinical Investigation, Demonstration of In Vitro and In Vivo Efficacy of Two Biologically Active Human Soluble TNF Receptors Expressed in E. coli," J. Cell Biochem. Suppl. 15F:113(1991).

Hass et al., "Characterization of specific high affinity receptors for human tumor necrosis factor on mouse fibroblasts," J. Biol. Chem. 260:12214-18 (1985).

Hatakeyama et al., "Interleukin-2 receptor beta chain gene: generation of three receptor forms by cloned human alpha and beta chain cDNA's," Science 244:551-56 (1989).

Hauser et al., "Cytokine accumulations in CSF of multiple sclerosis patients: frequent detection of interleukin-1 and tumor necrosis factor but not interleukin-6," Neurology 40:1735-39 (1990).

Heller et al., "Amplified expression of tumor necrosis factor receptor in cells transfected with Epstein-Barr virus shuttle vector cDNA libraries," J. Biol. Chem. 265:5708-17 (1990).

Himmler at al., "Molecular cloning and expression of human and rat tumor necrosis factor receptor chain (p60) and its soluble derivative, tumor necrosis factor-binding protein," DNA Cell Biol. 9:705-15 (1990).

Hofman et al., "Tumor necrosis factor identified in multiple sclerosis brain," J. Exp. Med. 170:607-12 (1989).

Israel et al., "Binding of Human TNF-alpha to High-Affinity Cell Surface Receptors: Effect of IFN," Immunol. Lett. 12:217-224(1986).

Kasukabe et al., "Purification of a novel growth inhibitory factor for partially differentiated myeloid leukemic cells," J. Biol. Chem. 263:5431-35 (1988).

Kohno et al., "A Second Tumor Necrosis Factor Receptor Gene Product Can Shed a Naturally Occurring Tumor Necrosis Factor Inhibitor," Proc. Natl. Acad. Sci. USA 87:8331-8335 (1990).

Kull et al., "Cellular receptor for 125I-labeled tumor necrosis factor: specific binding, affinity labeling, and relationship to sensitivity," Proc. Natl. Acad. Sci. U. S. A. 82:5756-60 (1985).

Lantz et al., "Characterization in vitro of a human tumor necrosis factor-binding protein. A soluble form of a tumor necrosis factor receptor," J. Clin. Invest. 86:1396-42 (1990).

Le et al., "Tumor necrosis factor and interleukin 1: cytokines with multiple overlapping biological activities," Lab. Invest. 56:234-48 (1987).

Lee et al., "Generation of cDNA probes directed by amino acid sequences: cloning of urate oxidase," Science 239:1288-91 (1988).

Lehmann and Droge, "Demonstration of membrane receptors for human natural and recombinant 125I-labeled tumor necrosis factor on HeLa cell clones and their role in tumor cell sensitivity," Eur. J. Biochem. 158:1-5 (1986).

Leung et al., "Growth hormone receptor and serum binding protein: purification, cloning and expression," Nature 330:537-43 (1987).

Liao et al., "Identification of a specific interleukin 1 inhibitor in the urine of febrile patients," J. Exp. Med. 159:126-36 (1984).

Liao et al., "Characterization of a Human Interleukin 1 Inhibitor," J. Immunol. 134(6):3882-3886 (1995).

Liblau et al., "Tumor Necrosis Factor-a and Disease Progreesion in Multiple Sclerosis," New Engl. J. Med. 326(4):272-273 (1992).

Lindvall et al., "Modulation of the constitutive gene expression of the 55 kD tumor necrosis factor receptor in hematopoietic cells," Biochem. Biophys. Res. Commun. 172:557-63 (1990).

Loetscher et al., "Recombinant 55-kDa tumor necrosis factor (TNF) receptor. Stoichiometry of binding to TNF alpha and TNF beta and inhibition of TNF activity," J. Biol. Chem. 266:18324-29 (1991).

March et al., "Cloning, sequence and expression of two distinct human interleukin-1 complementary DNAs," Nature 315:641-47 (1985).

Nexl et al., "Lectin-agarose immobilization, a new method for detecting soluble membrane receptors. Application to studies with epidermal growth factor-urogastrone and transcobalamin-II," J. Biol. Chem. 254:8740-43 (1979).

Nophar et al., "Soluble forms of tumor necrosis factor receptors (TNF-Rs). The cDNA of the type 1 TNF-R, cloned using amino acid sequence data of its soluble form, encodes both the cell surface and a soluble form of the receptor," The EMBO J. 9(10):3269-3278 (1990).

Novick et al., "Soluble cytokine receptors are present in normal human urine," J. Exp. Med. 170:1409-14 (1989).

Novick et al., "Soluble Cytokine Receptors are Present in Normal Human Urine," The Physiological and Pathological Effects of Cytokines pp. 413-21 (1990).

Novick et al., "Purification of soluble cytokine receptors from normal human urine by ligand-affinity and immunoaffinity chromatography," J. Chromatogr. 510:331-37 (1990).

Olsson et al., "Isolation and characterization of a tumor necrosis factor binding protein from urine," Eur. J. Haematol. 42:270-75 (1989).

Peetre, C. et al., Eur. J. Haematol 41:414-419 (1988).

Peppel et al., "A Tumor Necrosis Factor (TNF) Receptor-IgG Heavy Chain Chimeric Protein as a Bivalent Antagonist of TNF Activity," J. Exp. Med. 174:1483-1489 (1991).

Piguet et al., "Tumor necrosis factor/cachectin plays a key role in bleomycin-induced pneumopathy and fibrosis," J. Exp. Med. 170:655-63 (1989).

Ruddle et al., "An Antibody to Lymphotoxin and Tumor Necrosis Factor Prevents Transfer of Experimental Allergic Encephalomyelitis," J. Exp. Med. 172:1193-1200 (1990).

Schall, T. J. et al., Cell 61:361-370 (1990).

Scheurich et al., "Quantification and characterization of high-affinity membrane receptors for tumor necrosis factor on human leukemic cell lines," Int. J. Cancer 38:127-33 (1986).

Stauber and Aggarwal, "Characterization and affinity cross-linking of receptors for human recombinant lymphotoxin (tumor necrosis factor-beta) on a human histiocytic lymphoma cell line, U-937," J. Biol. Chem. 264:3573-76 (1989).

Suffys et al., "Involvement of a serine protease in tumour-necrosis-factor-mediated cytotoxicity," Eur. J. Biochem. 178:257-65 (1988).

Suggs et al., "Use of synthetic oligonucleotides as hybridization probes: isolation of cloned cDNA sequences for human beta 2-microglobulin," Proc. Natl. Acad. Sci. U. S. A. 78:6613-17 (1981).

The Cytokine Factsbook pp. 244-246 (Callard, ed., Academic Press, 1994).

Tracey et al., "Cachectin/tumor necrosis factor induces cachexia, anemia and inflammation," J. Exp. Med. 167:1211-27 (1988).

Tracey et al., "Metabolic effects of cachectin/tumor necrosis factor are modified by site of production. Cachectin/tumor necrosis factor-secreting tumor in skeletal muscle induces chronic cachexia, while implantation in brain induces predominantly acute anorexia," J. Clin. Invest. 86:2014-24 (1990).

Tracey et al., "Physiological responses to cachectin," Tumor Necrosis Factor and Related Cytotoxins pp. 88-108 (Ciba Foundation Symposium 131, Wiley, Chichester, 1987).

Unglaub et al., "Downregulation of tumor necrosis factor (TNF) sensitivity via modulation of TNF binding capacity by protein kinase C activators," J. Exp. Med. 166:1788-97 (1987).

Vilcek et al., "Tumor necrosis factor: receptor binding and mitogenic action in fibroblasts," J. Cell. Physiol. 5:57-61 (1987).

Wallach et al., "Mechanisms which take part in regulation of the response to tumor necrosis factor," Lymphokine Res. 8:359-63 (1989).

Wallach, "Preparations of lymphotoxin induce resistance to their own cytotoxic effect," J. Immunol. 132:2464-69 (1984).

Walsh et al., "Isolation and purification of U.S. an interleukin 1 inhibitor produced by human gingival epithelial cells," Clin. Exp. Immunol. 68:366-74 (1987).

Weber et al., "Production of an epidermal growth factor receptor-related protein," Science 224:294-97 (1984).

Yoshie et al., "Binding and Crosslinking of 125I-Labeled Recombinant Human Tumor Necrosis Factor to Cell Surface Receptors," J. Biochem. 100:531-541 (1986).

Ziegler, "Tumor necrosis factor in humans," N. Engl. J. Med. 318:1533-35 (1988).

Anderson et al., "Quantitative Filter Hybridization," *Nucleic Acid Hybridization: A Practical Approach* pp. 73-111 (Hawes et al., eds., 1985).

Dembic et al., "Two Human TNF Receptors Have Similar Extracellular, But Distinct Intracellular, Domain Sequences," *Cytokine* 2:231-37 (1990).

Neda, "Analysis of the Tumor Necrosis Factor (TNF) Receptor of Various Tumor Cells," *Tumor Necrosis Factor (TNF) Receptor* 56:305-17 (1987).

Rhein et al., "Another Sepsis Drug Down—Immunex TNF Receptor," *Biotechnology Newswatch* pp. 1, 3 (Monday, Oct. 4, 1993).

Vitt et al., "Biological and Structural Characterization of the Tumor Necrosis Factor Receptor on Multiple Cell Types: Relationship to Function," *Fed. Proc. 78th Annual Meeting of the American Society of Biological Chemists* 46:2117 (1987).

Wallach et al., "Regulation of the Response to Tumor Necrosis Factor," *Int. Conf. Tumor Necrosis Factor/Cachectin and Related Cytokines* pp. 134-147 (Bonavida et al., eds., 1987).

Selmaj et al., "Tumor Necrosis Factor Mediates Myelin and Oligodendrocyte Damage in Vitro", Annals of Neurolgoy 23(4):339-346 (1988).

Selmaj et al., "Proliferation of Astrocytes in Vitro in Response to Cytokines: A Primary Role for Tumor Necrosis Factor," J. Immunol. 144(1):129-135(1990).

Seckinger et al., "A Urine Inhibitor of Interleukin 1 Activity Affects Both Interleukin 1 α and 1β But Not Tumor Necrosis Factor α," J. Exp. Med. 139(5):1541-1545 (1987).

Seckinger et al., "A Urine Inhibitor of Interleukin 1 Activity That Blocks Ligand Binding", Immunol. 139(5):1546-1549 (1987).

Seckinger et al., "Characterization of a Tumor Necrosis Factor α (TNF-α) Inhibitor: Evidence of Immunological Cross-Reactivity with the TNF Receptor," Proc. Natl. Acad. Sci. USA 87:5188-5192 (1990).

Seckinger et al., "Purification and Biologic Characterization of a Specific Tumor Necrosis Factor α Inhibitor", The Journal of Biological Chemistry, vol. 264, No. 20 Issue of Jul. 15, pp. 11966-11973, 1989.

Smith et al., "A Receptor for Tumor Necrosis Factor Defines an Unusual Family of Cellular and Viral Proteins", Science 248:1019-1023 (1990).

Smith et al., "Species Specificity of Human and Murine Tumor Necrosis Factor", J.Biol. Chem. 261(32):14871-14874 (1986).

Socher et al., "Antibodies Against Amino Acids 1-15 of Tumor Necrosis Factor Block its Binding to Cell-Surface Receptor", Proc. Natl. Acad. Sci, vol. 84, pp. 8829-8833, Dec. 1987.

Spinas et al., "Induction of Plasma Inhibitors of Interleukin 1 and TNF-α activity by endotoxin administration to normal humans", Am. J. Physiol. 259: R993-R997 (1990).

Stauber et al., "Human Tumor Necrosis Factor-Alpha Receptor", J. Biol. Chem. 263(35):19098-19104 (1988).

Shimuzu et al., "Three Human Transforming Genes are Related to the Viral ras Oncogenes," Proc. Natl. Acad. Sci. U.S.A. 80:2112-16 (1983).

Heller et al., "Complementary DNA cloning of a receptor for Tumor Necrosis Factor and Demonstration of a Shed Form of the Receptor", Proc. Natl. Acad. Sci. vol. 87, pp. 6151-6155, Aug. 1990.

Hohmann et al., "Two Different Cell Types Have Different Major Receptors for Human Tumor Necrosis factor (TNFα),", J. Biol. Chem. 264(25):14927-14934 (1989).

Loetscher et al., "Molecular Cloning and Expression of the Human 55kd TNF Necrosis Factor Receptor," Cell 61:351-359 (1990).

European Search Report for the corresponding European Appl. No. EP90106624.1 corresponding to U.S. Appl. No. 07/511,430.

Tracey et al., "Anti-cachectin/TNF Monoclonal Antibodies Prevent Septic Shock During Lethal Bacteraemia," Nature 330:662-664 (1987).

Tsujimoto et al., "Characterization and Affinity Crosslinking of Receptors for Tumor Necrosis Factor on Human Cells", Archives of Biochem. & Biophys. 249(2):563-568 (1986).

Tracey et al., Physiological responses to cachectin, Tumor Necrosis Factor and Related Cytotoxins pp. 88-108 (Ciba Foundation Symposium 131, Wiley, Chichester, 1987).

US 5,843,791, 12/1998, Hauptmann et al. (withdrawn)

* cited by examiner

FIG. 1A

```
                              GAATTCTCTGGACTGAGGCTCCAGTTCTGGCCTTTGGGG

TTCAAGATCACTGGGACCAGGCCGTGATCTCTATGCCCGAGTCTCAACCCTCAACTGTC

ACCCCAAGGCACTTGGGACGTCCTGGACAGACCGAGTCCCGGGAAGCCCCAGCACTGCC
                                                         ***
GCTGCCACACTGCCCTGAGCCCAAATGGGGGAGTGAGAGGCCA TAG CTG TCT GGC
```

|  S1 |  |  |  | S5 |  |  |  |  | S10 |  |  |  | S15 |  |
|---|---|---|---|---|---|---|---|---|---|---|---|---|---|---|
| Met | Gly | Leu | Ser | Thr | Val | Pro | Asp | Leu | Leu | Leu | Pro | Leu | Val | Leu |
| ATG | GGC | CTC | TCC | ACC | GTG | CCT | GAC | CTG | CTG | CTG | CCA | CTG | GTG | CTC |
| 216 |  |  |  | 225 |  |  |  | 234 |  |  |  | 243 |  | 252 |

|  |  |  |  | S20 |  |  |  |  | S25 |  |  |  | S29 | 1 |
|---|---|---|---|---|---|---|---|---|---|---|---|---|---|---|
| Leu | Glu | Leu | Leu | Val | Gly | Ile | Tyr | Pro | Ser | Gly | Val | Ile | Gly | Leu |
| CTG | GAG | CTG | TTG | GTG | GGA | ATA | TAC | CCC | TCA | GGG | GTT | ATT | GGA | CTG |
| 261 |  |  |  | 270 |  |  |  | 279 |  | 288 |  |  |  | 297 |

|  |  |  |  | 5 |  |  |  |  | 10 |  |  |  | 15 |  |
|---|---|---|---|---|---|---|---|---|---|---|---|---|---|---|
| Val | Pro | His | Leu | Gly | Asp | Arg | Glu | Lys | Arg | Asp | Ser | Val | Cys | Pro |
| GTC | CCT | CAC | CTA | GGG | GAC | AGG | GAG | AAG | AGA | GAT | AGT | GTG | TGT | CCC |
| 306 |  |  |  | 315 |  |  |  | 324 |  |  |  | 333 |  | 342 |

|  |  |  |  | 20 |  |  |  |  | 25 |  |  |  | 30 |  |
|---|---|---|---|---|---|---|---|---|---|---|---|---|---|---|
| Gln | Gly | Lys | Tyr | Ile | His | Pro | Gln | Asn | Asn | Ser | Ile | Cys | Cys | Thr |
| CAA | GGA | AAA | TAT | ATC | CAC | CCT | CAA | AAT | AAT | TCG | ATT | TGC | TGT | ACC |
| 351 |  |  |  | 360 |  |  |  | 369 |  |  |  | 378 |  | 387 |

|  |  |  |  | 35 |  |  |  |  | 40 |  |  |  | 45 |  |
|---|---|---|---|---|---|---|---|---|---|---|---|---|---|---|
| Lys | Cys | His | Lys | Gly | Thr | Tyr | Leu | Tyr | Asn | Asp | Cys | Pro | Gly | Pro |
| AAG | TGC | CAC | AAA | GGA | ACC | TAC | TTG | TAC | AAT | GAC | TGT | CCA | GGC | CCG |
| 396 |  |  |  | 405 |  |  |  | 414 |  |  |  | 423 |  | 432 |

|  |  |  |  | 50 |  |  |  |  | 55 |  |  |  | 60 |  |
|---|---|---|---|---|---|---|---|---|---|---|---|---|---|---|
| Gly | Gln | Asp | Thr | Asp | Cys | Arg | Glu | Cys | Glu | Ser | Gly | Ser | Phe | Thr |
| GGG | CAG | GAT | ACG | GAC | TGC | AGG | GAG | TGT | GAG | AGC | GGC | TCC | TTC | ACC |
| 441 |  |  |  | 450 |  |  |  | 459 |  |  |  | 468 |  | 477 |

|  |  |  |  | 65 |  |  |  |  | 70 |  |  |  | 75 |  |
|---|---|---|---|---|---|---|---|---|---|---|---|---|---|---|
| Ala | Ser | Glu | Asn | His | Leu | Arg | His | Cys | Leu | Ser | Cys | Ser | Lys | Cys |
| GCT | TCA | GAA | AAC | CAC | CTC | AGA | CAC | TGC | CTC | AGC | TGC | TCC | AAA | TGC |
| 486 |  |  |  | 495 |  |  |  | 504 |  |  |  | 513 |  | 522 |

|  |  |  |  | 80 |  |  |  |  | 85 |  |  |  | 90 |  |
|---|---|---|---|---|---|---|---|---|---|---|---|---|---|---|
| Arg | Lys | Glu | Met | Gly | Gln | Val | Glu | Ile | Ser | Ser | Cys | Thr | Val | Asp |
| CGA | AAG | GAA | ATG | GGT | CAG | GTG | GAG | ATC | TCT | TCT | TGC | ACA | GTG | GAC |
| 531 |  |  |  | 540 |  |  |  | 549 |  |  |  | 558 |  | 567 |

FIG. 1B

|  | 95 |  | 100 |  | 105 |  |
|---|---|---|---|---|---|---|
| Arg Asp Thr | Val Cys Gly | Cys Arg Lys | Asn Gln Tyr | Arg His Tyr |
| CGG GAC ACC | GTG TGT GGC | TGC AGG AAG | AAC CAG TAC | CGG CAT TAT |
| 576 | 585 | 594 | 603 | 612 |

|  | 110 |  | 115 |  | 120 |
|---|---|---|---|---|---|
| Trp Ser Glu | Asn Leu Phe | Gln Cys Phe | Asn Cys Ser | Leu Cys Leu |
| TGG AGT GAA | AAC CTT TTC | CAG TGC TTC | AAT TGC AGC | CTC TGC CTC |
| 621 | 630 | 639 | 648 | 657 |

|  | 125 |  | 130 |  | 135 |
|---|---|---|---|---|---|
| Asn Gly Thr | Val His Leu | Ser Cys Gln | Glu Lys Gln | Asn Thr Val |
| AAT GGG ACC | GTG CAC CTC | TCC TGC CAG | GAG AAA CAG | AAC ACC GTG |
| 666 | 675 | 684 | 693 | 702 |

|  | 140 |  | 145 |  | 150 |
|---|---|---|---|---|---|
| Cys Thr Cys | His Ala Gly | Phe Phe Leu | Arg Glu Asn | Glu Cys Val |
| TGC ACC TGC | CAT GCA GGT | TTC TTT CTA | AGA GAA AAC | GAG TGT GTC |
| 711 | 720 | 729 | 738 | 747 |

|  | 155 |  | 160 |  | 165 |
|---|---|---|---|---|---|
| Ser Cys Ser | Asn Cys Lys | Lys Ser Leu | Glu Cys Thr | Lys Leu Cys |
| TCC TGT AGT | AAC TGT AAG | AAA AGC CTG | GAG TGC ACG | AAG TTG TGC |
| 756 | 765 | 774 | 783 | 792 |

|  | 170 |  | 175 |  | 180 |
|---|---|---|---|---|---|
| Leu Pro Gln | Ile Glu Asn | Val Lys Gly | Thr Glu Asp | Ser Gly Thr |
| CTA CCC CAG | ATT GAG AAT | GTT AAG GGC | ACT GAG GAC | TCA GGC ACC |
| 801 | 810 | 819 | 828 | 837 |

|  | 185 |  | 190 |  | 195 |
|---|---|---|---|---|---|
| Thr Val Leu | Leu Pro Leu | Val Ile Phe | Phe Gly Leu | Cys Leu Leu |
| ACA GTG CTG | TTG CCC CTG | GTC ATT TTC | TTT GGT CTT | TGC CTT TTA |
| 846 | 855 | 864 | 873 | 882 |

|  | 200 |  | 205 |  | 210 |
|---|---|---|---|---|---|
| Ser Leu Leu | Phe Ile Gly | Leu Met Tyr | Arg Tyr Gln | Arg Trp Lys |
| TCC CTC CTC | TTC ATT GGT | TTA ATG TAT | CGC TAC CAA | CGG TGG AAG |
| 891 | 900 | 909 | 918 | 927 |

|  | 215 |  | 220 |  | 225 |
|---|---|---|---|---|---|
| Ser Lys Leu | Tyr Ser Ile | Val Cys Gly | Lys Ser Thr | Pro Glu Lys |
| TCC AAG CTC | TAC TCC ATT | GTT TGT GGG | AAA TCG ACA | CCT GAA AAA |
| 936 | 945 | 954 | 963 | 972 |

|  | 230 |  | 235 |  | 240 |
|---|---|---|---|---|---|
| Glu Gly Glu | Leu Glu Gly | Thr Thr Thr | Lys Pro Leu | Ala Pro Asn |
| GAG GGG GAG | CTT GAA GGA | ACT ACT ACT | AAG CCC CTG | GCC CCA AAC |
| 981 | 990 | 999 | 1008 | 1017 |

FIG. 1C

```
              245                      250                       255
Pro Ser Phe Ser Pro Thr Pro Gly Phe Thr Pro Thr Leu Gly Phe
CCA AGC TTC AGT CCC ACT CCA GGC TTC ACC CCC ACC CTG GGC TTC
 1026        1035        1044        1053        1062

260                      265                       270
Ser Pro Val Pro Ser Ser Thr Phe Thr Ser Ser Ser Thr Tyr Thr
AGT CCC GTG CCC AGT TCC ACC TTC ACC TCC AGC TCC ACC TAT ACC
 1071        1080        1089        1098        1107

275                      280                       285
Pro Gly Asp Cys Pro Asn Phe Ala Ala Pro Arg Arg Glu Val Ala
CCC GGT GAC TGT CCC AAC TTT GCG GCT CCC CGC AGA GAG GTG GCA
 1116        1125        1134        1143        1152

290                      295                       300
Pro Pro Tyr Gln Gly Ala Asp Pro Ile Leu Ala Thr Ala Leu Ala
CCA CCC TAT CAG GGG GCT GAC CCC ATC CTT GCG ACA GCC CTC GCC
 1161        1170        1179        1188        1197

305                      310                       315
Ser Asp Pro Ile Pro Asn Pro Leu Gln Lys Trp Glu Asp Ser Ala
TCC GAC CCC ATC CCC AAC CCC CTT CAG AAG TGG GAG GAC AGC GCC
 1206        1215        1224        1233        1242

320                      325                       330
His Lys Pro Gln Ser Leu Asp Thr Asp Asp Pro Ala Thr Leu Tyr
CAC AAG CCA CAG AGC CTA GAC ACT GAT GAC CCC GCG ACG CTG TAC
 1251        1260        1269        1278        1287

335                      340
Ala Val Val Glu Asn Val Pro Pro Leu Arg Trp
GCC GTG GTG GAG AAC GTG CCC CCG TTG CGC TGG AA GGAATTC
 1296        1305        1314        1323        1332
```

FIG. 6A pAD-CMV1 : 6414 bp

```
TCGACATTGA TTATTGACTA GTTATTAATA GTAATCAATT ACGGGGTCAT TAGTTCATAG      60
CCCATATATG GAGTTCCGCG TTACATAACT TACGGTAAAT GGCCCGCCTG GCTGACCGCC     120
CAACGACCCC CGCCCATTGA CGTCAATAAT GACGTATGTT CCCATAGTAA CGCCAATAGG     180
GACTTTCCAT TGACGTCAAT GGGTGGAGTA TTTACGGTAA ACTGCCCACT TGGCAGTACA     240
TCAAGTGTAT CATATGCCAA GTACGCCCCC TATTGACGTC AATGACGGTA AATGGCCCGC     300
CTGGCATTAT GCCCAGTACA TGACCTTATG GACTTTCCT ACTTGGCAGT ACATCTACGT      360
ATTAGTCATC GCTATTACCA TGGTGATGCG GTTTTGGCAG TACATCAATG GGCGTGGATA     420
GCGGTTTGAC TCACGGGGAT TTCCAAGTCT CCACCCCATT GACGTCAATG GGAGTTTGTT     480
TTGGCACCAA AATCAACGGG ACTTTCCAAA ATGTCGTAAC AACTCCGCCC CATTGACGCA     540
AATGGGCGGT AGGCGTGTAC GGTGGGAGGT CTATATAAGC AGAGCTCTCT GGCTAACTAG     600
AGAACCCACT GCTTAACTGG CTTATCGAAA TTAATACGAC TCACTATAGG GAGACCCAAG     660
CTTCTGCAGG TCGACATCGA TGGATCCGGT ACCTCGAGCG CGAATTCTCT AGAGGATCTT     720
TGTGAAGGAA CCTTACTTCT GTGGTGTGAC ATAATTGGAC AAACTACCTA CAGAGATTTA     780
AAGCTCTAAG GTAAATATAA AATTTTTAAG TGTATAATGT GTTAAACTAC TGATTCTAAT     840
TGTTTGTGTA TTTTAGATTC CAACCTATGG AACTGATGAA TGGGAGCAGT GGTGGAATGC     900
CTTTAATGAG GAAAACCTGT TTTGCTCAGA AGAAATGCCA TCTAGTGATG ATGAGGCTAC     960
TGCTGACTCT CAACATTCTA CTCCTCCAAA AAAGAAGAGA AAGGTAGAAG ACCCCAAGGA    1020
CTTTCCTTCA GAATTGCTAA GTTTTTTGAG TCATGCTGTG TTTAGTAATA GAACTCTTGC    1080
TTGCTTTGCT ATTTACACCA CAAAGGAAAA AGCTGCACTG CTATACAAGA AAATTATGGA    1140
AAAATATTTG ATGTATAGTG CCTTGACTAG AGATCATAAT CAGCCATACC ACATTTGTAG    1200
AGGTTTTACT TGCTTTAAAA AACCTCCCAC ACCTCCCCCT GAACCTGAAA CATAAAATGA    1260
ATGCAATTGT TGTTGTTAAC TTGTTTATTG CAGCTTATAA TGGTTACAAA TAAAGCAATA    1320
GCATCACAAA TTTCACAAAT AAAGCATTTT TTTCACTGCA TTCTAGTTGT GGTTTGTCCA    1380
AACTCATCAA TGTATCTTAT CATGTCTGGA TCAATTCTGA GAAACTAGCC TTAAAGACAG    1440
```

FIG. 6B

```
ACAGCTTTGT TCTAGTCAGC CAGGCAAGCA TATGTAAATA AAGTTCCTCA GGGAACTGAG    1500
GTTAAAAGAT GTATCCTGGA CCTGCCAGAC CTGGCCATTC ACGTAAACAG AAGATTCCGC    1560
CTCAAGTTCC GGTTAACAAC AGGAGGCAAC GAGATCTCAA ATCTATTACT TCTAATCGGG    1620
TAATTAAAAC CTTTCAACTA AAACACGGAC CCACGGATGT CACCCACTTT TCCTTCCCCG    1680
GCTCCGCCCT TCTCAGTACT CCCCACCATT AGGCTCGCTA CTCCACCTCC ACTTCCGGGC    1740
GCGACACCCA CGTGCCCTCT CCCACCCGAC GCTAACCCCG CCCTGCCCG TCTGACCCCG     1800
CCCACCACCT GGCCCCGCCC CGTTGAGGAC AGAAGAAACC CCGGGCAGCC GCAGCCAAGG    1860
CGGACGGGTA GACGCTGGGG GCGCTGAGGA GTCGTCCTCT ACCTTCTCTG CTGGCTCGGT    1920
GGGGGACGCG GTGGATCTCA GGCTTCCGGA AGACTGGAAG AACCGGCTCA GAACCGCTTG    1980
TCTCCGCGGG GCTTGGGCGG CGGAAGAATG GCCGCTAGAC GCGGACTTGG TGCGAGGCAT    2040
CGCAGGATGC AGAAGAGCAA GCCCGCCGGG AGCGCGCGGC TGTACTACCC CGCGCCTGGA    2100
GCGGCCACGC CGGACTGGGC GGGGCCGGCC TGGTGGAGGC GGAGTCTGAC CTCGTGGAGG    2160
CGGGGCCTCT GATGTTCAAA TAGGATGCTA GGCTTGTTGA GGCGTGGCCT CCGATTCACA    2220
AGTGGGAAGC AGCGCCGGGC GACTGCAATT TCGCGCCAAA CTTGGGGGAA GCACAGCGTA    2280
CAGGCTGCCT AGGTGATCGC TGCTGCTGTC ATGGTTCGAC CGCTGAACTG CATCGTCGCC    2340
GTGTCCCAGA ATATGGGCAT CGGCAAGAAC GGAGACCTTC CCTGGCCAAT GCTCAGGTAC    2400
TGGCTGGATT GGGTTAGGGA AACCGAGGCG GTTCGCTGAA TCGGGTCGAG CACTTGGCGG    2460
AGACGCGCGG GCCAACTACT TAGGGACAGT CATGAGGGGT AGGCCCGCCG GCTGCTGCCC    2520
TTGCCCATGC CCGCGGTGAT CCCCATGCTG TGCCAGCCTT TGCCCAGAGG CGCTCTAGCT    2580
GGGAGCAAAG TCCGGTCACT GGGCAGCACC ACCCCCCGGA CTTGCATGGG TAGCCGCTGA    2640
GATGGAGCCT GAGCACACGT GACAGGGTCC CTGTTAACGC AGTGTTTCTC TAACTTTCAG    2700
GAACGAGTTC AAGTACTTCC AAAGAATGAC CACCACCTCC TCAGTGGAAG GTAAACAGAA    2760
CCTGGTGATT ATGGGCCGGA AAACCTGGTT CTCCATTCCT GAGAAGAATC GACCTTTAAA    2820
GGACAGAATT AATATAGTTC TCAGTAGAGA GCTCAAGGAA CCACCACAAG GAGCTCATTT    2880
TCTTGCCAAA AGTCTGGACC ATGCCTTAAA ACTTATTGAA CAACCAGAGT TAGCAGATAA    2940
AGTGGACATG GTTTGGATAG TTGGAGGCAG TTCCGTTTAC AAGGAAGCCA TGAATCAGCC    3000
```

FIG. 6C

```
AGGCCATCTC AGACTCTTTG TGACAAGGAT CATGCAGGAA TTTGAAAGTG ACACGTTCTT    3060
CCCAGAAATT GATTTGGAGA AATATAAACT TCTCCCAGAG TACCCAGGGG TCCTTTCTGA    3120
AGTCCAGGAG GAAAAAGGCA TCAAGTATAA ATTTGAAGTC TATGAGAAGA AAGGCTAACA    3180
GAAAGATACT TGCTGATTGA CTTCAAGTTC TACTGCTTTC CTCCTAAAAT TATGCATTTT    3240
TACAAGACCA TGGGACTTGT GTTGGCTTTA GATCCTGTGC ATCCTGGGCA ACTGTTGTAC    3300
TCTAAGCCAC TCCCCAAAGT CATGCCCCAG CCCCTGTATA ATTCTAAACA ATTAGAATTA    3360
TTTTCATTTT CATTAGTCTA ACCAGGTTAT ATTAAATATA CTTTAAGAAA CACCATTTGC    3420
CATAAAGTTC TCAATGCCCC TCCCATGCAG CCTCAAGTGG CTCCCCAGCA GATGCATAGG    3480
GTAGTGTGTG TACAAGAGAC CCCAAAGACA TAGAGCCCCT GAGAGCATGA GCTGATATGG    3540
GGGCTCATAG AGATAGGAGC TAGATGAATA AGTACAAAGG GCAGAAATGG GTTTTAACCA    3600
GCAGAGCTAG AACTCAGACT TTAAAGAAAA TTAGATCAAA GTAGAGACTG AATTATTCTG    3660
CACATCAGAC TCTGAGCAGA GTTCTGTTCA CTCAGACAGA AAATGGGTAA ATTGAGAGCT    3720
GGCTCCATTG TGCTCCTTAG AGATGGGAGC AGGTGGAGGA TTATATAAGG TCTGGAACAT    3780
TTAACTTCTC CGTTTCTCAT CTTCAGTGAG ATTCCAAGGG ATACTACAAT TCTGTGGAAT    3840
GTGTGTCAGT TAGGGTGTGG AAAGTCCCCA GGCTCCCCAG CAGGCAGAAG TATGCAAAGC    3900
ATGCATCTCA ATTAGTCAGC AACCAGGTGT GGAAAGTCCC CAGGCTCCCC AGCAGGCAGA    3960
AGTATGCAAA GCATGCATCT CAATTAGTCA GCAACCATAG TCCCGCCCCT AACTCCGCCC    4020
ATCCCGCCCC TAACTCCGCC CAGTTCCGCC CATTCTCCGC CCCATGGCTG ACTAATTTTT    4080
TTTATTTATG CAGAGGCCGA GGCGCCTCTG AGCTATTCCA GAAGTAGTGA GGAGGCTTTT    4140
TTGGAGGCCT AGGCTTTTGC AAAAAAGCTA ATTCAGCCTG AATGGCGAAT GGGACGCGCC    4200
CTGTAGCGGC GCATTAAGCG CGGCGGGTGT GGTGGTTACG CGCAGCGTGA CCGCTACACT    4260
TGCCAGCGCC CTAGCGCCCG CTCCTTTCGC TTTCTTCCCT TCCTTTCTCG CCACGTTCGC    4320
CGGCTTTCCC CGTCAAGCTC TAAATCGGGG GCTCCCTTTA GGGTTCCGAT TTAGTGCTTT    4380
ACGGCACCTC GACCCCAAAA ACTTGATTAG GGTGATGGTT CACGTAGTGG GCCATCGCCC    4440
TGATAGACGG TTTTTCGCCC TTTGACGTTG GAGTCCACGT TCTTTAATAG TGGACTCTTG    4500
TTCCAAACTG GAACAACACT CAACCCTATC TCGGTCTATT CTTTTGATTT ATAAGGGATT    4560
```

FIG. 6D

```
TTGCCGATTT CGGCCTATTG GTTAAAAAAT GAGCTGATTT AACAAAAATT TAACGCGAAT    4620
TTTAACAAAA TATTAACGTT TACAATTTCA GGTGGCACTT TTCGGGGAAA TGTGCGCGGA    4680
ACCCCTATTT GTTTATTTTT CTAAATACAT TCAAATATGT ATCCGCTCAT GAGACAATAA    4740
CCCTGATAAA TGCTTCAATA ATATTGAAAA AGGAAGAGTA TGAGTATTCA ACATTTCCGT    4800
GTCGCCCTTA TTCCCTTTTT TGCGGCATTT TGCCTTCCTG TTTTTGCTCA CCCAGAAACG    4860
CTGGTGAAAG TAAAAGATGC TGAAGATCAG TTGGGTGCAC GAGTGGGTTA CATCGAACTG    4920
GATCTCAACA GCGGTAAGAT CCTTGAGAGT TTTCGCCCCG AAGAACGTTT TCCAATGATG    4980
AGCACTTTTA AAGTTCTGCT ATGTGGCGCG GTATTATCCC GTATTGACGC CGGGCAAGAG    5040
CAACTCGGTC GCCGCATACA CTATTCTCAG AATGACTTGG TTGAGTACTC ACCAGTCACA    5100
GAAAAGCATC TTACGGATGG CATGACAGTA AGAGAATTAT GCAGTGCTGC CATAACCATG    5160
AGTGATAACA CTGCGGCCAA CTTACTTCTG ACAACGATCG GAGGACCGAA GGAGCTAACC    5220
GCTTTTTTGC ACAACATGGG GGATCATGTA ACTCGCCTTG ATCGTTGGGA ACCGGAGCTG    5280
AATGAAGCCA TACCAAACGA CGAGCGTGAC ACCACGATGC CTGTAGCAAT GGCAACAACG    5340
TTGCGCAAAC TATTAACTGG CGAACTACTT ACTCTAGCTT CCCGGCAACA ATTAATAGAC    5400
TGGATGGAGG CGGATAAAGT TGCAGGACCA CTTCTGCGCT CGGCCCTTCC GGCTGGCTGG    5460
TTTATTGCTG ATAAATCTGG AGCCGGTGAG CGTGGGTCTC GCGGTATCAT TGCAGCACTG    5520
GGGCCAGATG GTAAGCCCTC CCGTATCGTA GTTATCTACA CGACGGGGAG TCAGGCAACT    5580
ATGGATGAAC GAAATAGACA GATCGCTGAG ATAGGTGCCT CACTGATTAA GCATTGGTAA    5640
CTGTCAGACC AAGTTTACTC ATATATACTT TAGATTGATT TAAAACTTCA TTTTTAATTT    5700
AAAAGGATCT AGGTGAAGAT CCTTTTTGAT AATCTCATGA CCAAAATCCC TTAACGTGAG    5760
TTTTCGTTCC ACTGAGCGTC AGACCCCGTA GAAAAGATCA AAGGATCTTC TTGAGATCCT    5820
TTTTTTCTGC GCGTAATCTG CTGCTTGCAA ACAAAAAAAC CACCGCTACC AGCGGTGGTT    5880
TGTTTGCCGG ATCAAGAGCT ACCAACTCTT TTTCCGAAGG TAACTGGCTT CAGCAGAGCG    5940
CAGATACCAA ATACTGTCCT TCTAGTGTAG CCGTAGTTAG GCCACCACTT CAAGAACTCT    6000
GTAGCACCGC CTACATACCT CGCTCTGCTA ATCCTGTTAC CAGTGGCTGC TGCCAGTGGC    6060
GATAAGTCGT GTCTTACCGG GTTGGACTCA AGACGATAGT TACCGGATAA GGCGCAGCGG    6120
```

FIG. 6E

```
TCGGGCTGAA CGGGGGGTTC GTGCACACAG CCCAGCTTGG AGCGAACGAC CTACACCGAA    6180
CTGAGATACC TACAGCGTGA GCATTGAGAA AGCGCCACGC TTCCCGAAGG GAGAAAGGCG    6240
GACAGGTATC CGGTAAGCGG CAGGGTCGGA ACAGGAGAGC GCACGAGGGA GCTTCCAGGG    6300
GGAAACGCCT GGTATCTTTA TAGTCCTGTC GGGTTTCGCC ACCTCTGACT TGAGCGTCGA    6360
TTTTTGTGAT GCTCGTCAGG GGGCGGAGC CTATGGAAAA ACGCCAGCAA CGCC
```

FIG. 8A raTNF-R

```
GAATTCCTTT TCTCCGAGTT TTCTGAACTC TGGCTCATGA TCGGGCTTAC TGGATACGAG    60
AATCCTGGAG, GACCGTACCC TGATTTCCAT CTACCTCTGA CTTTGAGCCT TTCTAACCCG   120
GGGCTCACGC TGCCAACACC CGGGCCACCT GGTCCGATCG TCTTACTTCA TTCACCAGCG   180
TTGCCAATTG CTGCCCTGTC CCCAGCCCCA ATGGGGAGT  GAGAGAGGCC ACTGCCGGCC   240
GGAC
```

| 245/1 | | | | | | | | | | 275/11 | | | | | | | | | |
|---|---|---|---|---|---|---|---|---|---|---|---|---|---|---|---|---|---|---|---|
| ATG | GGT | CTC | CCC | ATC | GTG | CCT | GGC | CTG | CTG | CTG | TCA | CTG | GTG | CTC | CTG | GCT | CTG | CTG | ATG |
| Met | Gly | Leu | Pro | Ile | Val | Pro | Gly | Leu | Leu | Leu | Ser | Leu | Val | Leu | Leu | Ala | Leu | Leu | Met |
| 305/21 | | | | | | | | | | 335/31 | | | | | | | | | |
| GGG | ATA | CAC | CCA | TCA | GGG | GTC | ACC | GGA | CTG | GTT | CCT | TCT | CTT | GGT | GAC | CGG | GAG | AAG | AGG |
| Gly | Ile | His | Pro | Ser | Gly | Val | Thr | Gly | Leu | Val | Pro | Ser | Leu | Gly | Asp | Arg | Glu | Lys | Arg |
| 365/41 | | | | | | | | | | 395/51 | | | | | | | | | |
| GAT | AAT | TTG | TGT | CCC | CAG | GGA | AAG | TAT | GCC | CAT | CCA | AAG | AAT | AAT | TCC | ATC | TGC | TGC | ACC |
| Asp | Asn | Leu | Cys | Pro | Gln | Gly | Lys | Tyr | Ala | His | Pro | Lys | Asn | Asn | Ser | Ile | Cys | Cys | Thr |
| 425/61 | | | | | | | | | | 455/71 | | | | | | | | | |
| AAG | TGC | CAC | AAA | GGA | ACC | TAC | TTG | GTG | AGT | GAC | TGT | CCA | AGC | CCA | GGG | CAG | GAA | ACA | GTC |
| Lys | Cys | His | Lys | Gly | Thr | Tyr | Leu | Val | Ser | Asp | Cys | Pro | Ser | Pro | Gly | Gln | Glu | Thr | Val |
| 485/81 | | | | | | | | | | 515/91 | | | | | | | | | |
| TGC | GAG | CTC | TCT | CAT | AAA | GGC | ACC | TTT | ACA | GCT | TCG | CAG | AAC | CAC | GTC | AGA | CAG | TGT | CTC |
| Cys | Glu | Leu | Ser | His | Lys | Gly | Thr | Phe | Thr | Ala | Ser | Gln | Asn | His | Val | Arg | Gln | Cys | Leu |
| 545/101 | | | | | | | | | | 575/111 | | | | | | | | | |
| AGT | TGC | AAG | ACA | TGT | CGG | AAA | GAA | ATG | TTC | CAG | GTG | GAG | ATT | TCT | CCT | TGC | AAA | GCT | GAC |
| Ser | Cys | Lys | Thr | Cys | Arg | Lys | Glu | Met | Phe | Gln | Val | Glu | Ile | Ser | Pro | Cys | Lys | Ala | Asp |
| 605/121 | | | | | | | | | | 635/131 | | | | | | | | | |
| ATG | GAC | ACC | GTG | TGT | GGC | TGC | AAG | AAG | AAC | CAA | TTC | CAG | CGC | TAC | CTG | AGT | GAG | ACG | CAT |
| Met | Asp | Thr | Val | Cys | Gly | Cys | Lys | Lys | Asn | Gln | Phe | Gln | Arg | Tyr | Leu | Ser | Glu | Thr | His |
| 665/141 | | | | | | | | | | 695/151 | | | | | | | | | |
| TTC | CAG | TGT | GTG | GAC | TGC | AGC | CCC | TGC | TTC | AAT | GGC | ACC | GTG | ACA | ATC | CCC | TGT | AAG | GAG |
| Phe | Gln | Cys | Val | Asp | Cys | Ser | Pro | Cys | Phe | Asn | Gly | Thr | Val | Thr | Ile | Pro | Cys | Lys | Glu |
| 725/161 | | | | | | | | | | 755/171 | | | | | | | | | |
| AAA | CAG | AAC | ACC | GTG | TGT | AAC | TGC | CAC | GCA | GGA | TTC | TTT | CTA | AGC | GGA | AAT | GAG | TGC | ACC |
| Lys | Gln | Asn | Thr | Val | Cys | Asn | Cys | His | Ala | Gly | Phe | Phe | Leu | Ser | Gly | Asn | Glu | Cys | Thr |
| 785/181 | | | | | | | | | | 815/191 | | | | | | | | | |
| CCT | TGC | AGC | CAC | TGC | AAG | AAA | AAT | CAG | GAA | TGT | ATG | AAG | CTG | TGC | CTA | CCT | CCA | GTT | GCA |
| Pro | Cys | Ser | His | Cys | Lys | Lys | Asn | Gln | Glu | Cys | Met | Lys | Leu | Cys | Leu | Pro | Pro | Val | Ala |
| 845/201 | | | | | | | | | | 875/211 | | | | | | | | | |
| AAT | GTC | ACA | AAC | CCC | CAG | GAC | TCA | GGT | ACT | GCC | GTG | CTG | TTG | CCT | CTG | GTT | ATC | TTC | CTA |
| Asn | Val | Thr | Asn | Pro | Gln | Asp | Ser | Gly | Thr | Ala | Val | Leu | Leu | Pro | Leu | Val | Ile | Phe | Leu |
| 905/221 | | | | | | | | | | 935/231 | | | | | | | | | |
| GGT | CTT | TGC | CTT | TTA | TTC | TTT | ATC | TGC | ATC | AGT | CTA | CTG | TGC | CGA | TAT | CCC | CAG | TGG | AGG |
| Gly | Leu | Cys | Leu | Leu | Phe | Phe | Ile | Cys | Ile | Ser | Leu | Leu | Cys | Arg | Tyr | Pro | Gln | Trp | Arg |
| 965/241 | | | | | | | | | | 995/251 | | | | | | | | | |
| CCC | AGG | GTC | TAC | TCC | ATC | ATT | TGT | AGG | GAT | TCA | GCT | CCT | GTC | AAA | GAG | GTG | GAG | GGT | GAA |
| Pro | Arg | Val | Tyr | Ser | Ile | Ile | Cys | Arg | Asp | Ser | Ala | Pro | Val | Lys | Glu | Val | Glu | Gly | Glu |
| 1025/261 | | | | | | | | | | 1055/271 | | | | | | | | | |
| GGA | ATT | GTT | ACT | AAG | CCC | CTA | ACT | CCA | GCC | TCT | ATC | CCA | GCC | TTC | AGC | CCC | AAC | CCC | GGC |
| Gly | Ile | Val | Thr | Lys | Pro | Leu | Thr | Pro | Ala | Ser | Ile | Pro | Ala | Phe | Ser | Pro | Asn | Pro | Gly |
| 1085/281 | | | | | | | | | | 1115/291 | | | | | | | | | |
| TTC | AAC | CCC | ACT | CTG | GGC | TTC | AGC | ACC | ACC | CCA | CGC | TTC | AGT | CAT | CCT | GTC | TCC | AGT | ACC |
| Phe | Asn | Pro | Thr | Leu | Gly | Phe | Ser | Thr | Thr | Pro | Arg | Phe | Ser | His | Pro | Val | Ser | Ser | Thr |
| 1145/301 | | | | | | | | | | 1175/311 | | | | | | | | | |
| CCC | ATC | AGC | CCC | GTC | TTC | GGT | CCT | AGT | AAC | TGG | CAC | AAC | TTC | GTG | CCA | CCT | GTA | AGA | GAG |
| Pro | Ile | Ser | Pro | Val | Phe | Gly | Pro | Ser | Asn | Trp | His | Asn | Phe | Val | Pro | Pro | Val | Arg | Glu |
| 1205/321 | | | | | | | | | | 1235/331 | | | | | | | | | |
| GTG | GTC | CCA | ACC | CAG | GGT | GCT | GAC | CCT | CTC | CTC | TAC | GGA | TCC | CTC | AAC | CCT | GTG | CCA | ATC |
| Val | Val | Pro | Thr | Gln | Gly | Ala | Asp | Pro | Leu | Leu | Tyr | Gly | Ser | Leu | Asn | Pro | Val | Pro | Ile |

FIG. 8B

```
1265/341                                    1295/351
CCC GCC CCT GTT CGG AAA TGG GAA GAC GTC GTC GCG GCC CAG CCA CAA CGG CTT GAC ACT
Pro Ala Pro Val Arg Lys Trp Glu Asp Val Val Ala Ala Gln Pro Gln Arg Leu Asp Thr
1325/361                                    1355/371
GCA GAC CCT GCG ATG CTG TAT GCT GTG GTG GAT GGC GTG CCT CCG ACA CGC TGG AAG GAG
Ala Asp Pro Ala Met Leu Tyr Ala Val Val Asp Gly Val Pro Pro Thr Arg Trp Lys Glu
1385/381                                    1415/391
TTC ATG CGG CTC CTG GGG CTG AGC GAG CAC GAG ATC GAG CGG CTG GAG CTG CAG AAC GGG
Phe Met Arg Leu Leu Gly Leu Ser Glu His Glu Ile Glu Arg Leu Glu Leu Gln Asn Gly
1445/401                                    1475/411
CGT TGC CTC CGC GAG GCT CAT TAC AGC ATG CTG GAA GCC TGG CGG CGC CGC ACA CCG CGA
Arg Cys Leu Arg Glu Ala His Tyr Ser Met Leu Glu Ala Trp Arg Arg Arg Thr Pro Arg
1505/421                                    1535/431
CAC GAG GCC ACG CTG GAC GTA GTG GGC CGC GTG CTT TGC GAC ATG AAC CTG CGT GGC TGC
His Glu Ala Thr Leu Asp Val Val Gly Arg Val Leu Cys Asp Met Asn Leu Arg Gly Cys
1565/441                                    1595/451
CTG GAG AAC ATC CGC GAG ACT CTA GAA AGC CCT GCC CAC TCG TCC ACG ACC CAC CTC CCG
Leu Glu Asn Ile Arg Glu Thr Leu Glu Ser Pro Ala His Ser Ser Thr Thr His Leu Pro
1625/461
CGA TAA
Arg Stop
            GGCCACACCC CCACCTCAGG AACGGGACTC GAAGGACCAT CCTGCTAGAT   1680
GCCCTGCTTC CCTGTGAACC TCCTCTTTGG TCCTCTAGGG GGCAGGCTCG ATCTGGCAGG   1740
CTCGATCTGG CAGCCACTTC CTTGGTGCTA CCGACTTGGT GTACATAGCT TTTCCCAGCT   1800
GCCGAGGACA GCCTGTGCCA GCCACTTGTG CATGGCAGGG AAGTGTGCCA TCTGCTCCCA   1860
GACAGCTGAG GGTGCCAAAA GCCAGGAGAG GTGATTGTGG AGAAAAAGCA CAATCTATCT   1920
GATACCCACT TGGGATGCAA GGACCCAAAC AAAGCTTCTC AGGGCCTCCT CAGTTGATTT   1980
CTGGGCCCTT TTCACAGTAG ATAAAACAGT CTTTGTATTG ATTATATCAC ACTAATGGAT   2040
GAACGGTTGA ACTCCCTAAG GTAGGGGCAA GCACAGAACA GTGGGGTCTC CAGCTGGAGC   2100
CCCCGACTCT TGTAAATACA CTAAAAATCT AAAAGTGAAA AAAAAAAAAA AAAAAAAAA    2160
AAAAAGGAA TTC
```

FIG. 9A huTNF-R

```
GAATTCTCTG GACTGAGGCT CCAGTTCTGG CCTTTGGGGT TCAAGATCAC TGGGACCAGG      60
CCGTGATCTC TATGCCCGAG TCTCAACCCT CAACTGTCAC CCCAAGGCAC TTGGGACGTC     120
CTGGACAGAC CGAGTCCCGG GAAGCCCCAG CACTGCCGCT GCCACACTGC CCTGAGCCCA     180
AATGGGGGAG TGAGAGGCCA TAGCTGTCTG GC
```

```
213/1                                      243/11
ATG GGC CTC TCC ACC GTG CCT GAC CTG CTG CTG CCA CTG GTG CTC CTG GAG CTG TTG GTG
Met Gly Leu Ser Thr Val Pro Asp Leu Leu Leu Pro Leu Val Leu Leu Glu Leu Leu Val
273/21                                     303/31
GGA ATA TAC CCC TCA GGG GTT ATT GGA CTG GTC CCT CAC CTA GGG GAC AGG GAG AAG AGA
Gly Ile Tyr Pro Ser Gly Val Ile Gly Leu Val Pro His Leu Gly Asp Arg Glu Lys Arg
333/41                                     363/51
GAT AGT GTG TGT CCC CAA GGA AAA TAT ATC CAC CCT CAA AAT AAT TCG ATT TGC TGT ACC
Asp Ser Val Cys Pro Gln Gly Lys Tyr Ile His Pro Gln Asn Asn Ser Ile Cys Cys Thr
393/61                                     423/71
AAG TGC CAC AAA GGA ACC TAC TTG TAC AAT GAC TGT CCA GGC CCG GGG CAG GAT ACG GAC
Lys Cys His Lys Gly Thr Tyr Leu Tyr Asn Asp Cys Pro Gly Pro Gly Gln Asp Thr Asp
453/81                                     483/91
TGC AGG GAG TGT GAG AGC GGC TCC TTC ACC GCT TCA GAA AAC CAC CTC AGA CAC TGC CTC
Cys Arg Glu Cys Glu Ser Gly Ser Phe Thr Ala Ser Glu Asn His Leu Arg His Cys Leu
513/101                                    543/111
AGC TGC TCC AAA TGC CGA AAG GAA ATG GGT CAG GTG GAG ATC TCT TCT TGC ACA GTG GAC
Ser Cys Ser Lys Cys Arg Lys Glu Met Gly Gln Val Glu Ile Ser Ser Cys Thr Val Asp
573/121                                    603/131
CGG GAC ACC GTG TGT GGC TGC AGG AAG AAC CAG TAC CGG CAT TAT TGG AGT GAA AAC CTT
Arg Asp Thr Val Cys Gly Cys Arg Lys Asn Gln Tyr Arg His Tyr Trp Ser Glu Asn Leu
633/141                                    663/151
TTC CAG TGC TTC AAT TGC AGC CTC TGC CTC AAT GGG ACC GTG CAC CTC TCC TGC CAG GAG
Phe Gln Cys Phe Asn Cys Ser Leu Cys Leu Asn Gly Thr Val His Leu Ser Cys Gln Glu
693/161                                    723/171
AAA CAG AAC ACC GTG TGC ACC TGC CAT GCA GGT TTC TTT CTA AGA GAA AAC GAG TGT GTC
Lys Gln Asn Thr Val Cys Thr Cys His Ala Gly Phe Phe Leu Arg Glu Asn Glu Cys Val
753/181                                    783/191
TCC TGT AGT AAC TGT AAG AAA AGC CTG GAG TGC ACG AAG TTG TGC CTA CCC CAG ATT GAG
Ser Cys Ser Asn Cys Lys Lys Ser Leu Glu Cys Thr Lys Leu Cys Leu Pro Gln Ile Glu
813/201                                    843/211
AAT GTT AAG GGC ACT GAG GAC TCA GGC ACC ACA GTG CTG TTG CCC CTG GTC ATT TTC TTT
Asn Val Lys Gly Thr Glu Asp Ser Gly Thr Thr Val Leu Leu Pro Leu Val Ile Phe Phe
873/221                                    903/231
GGT CTT TGC CTT TTA TCC CTC CTC TTC ATT GGT TTA ATG TAT CGC TAC CAA CGG TGG AAG
Gly Leu Cys Leu Leu Ser Leu Leu Phe Ile Gly Leu Met Tyr Arg Tyr Gln Arg Trp Lys
933/241                                    963/251
TCC AAG CTC TAC TCC ATT GTT TGT GGG AAA TCG ACA CCT GAA AAA GAG GGG GAG CTT GAA
Ser Lys Leu Tyr Ser Ile Val Cys Gly Lys Ser Thr Pro Glu Lys Glu Gly Glu Leu Glu
993/261                                    1023/271
GGA ACT ACT ACT AAG CCC CTG GCC CCA AAC CCA AGC TTC AGT CCC ACT CCA GGC TTC ACC
Gly Thr Thr Thr Lys Pro Leu Ala Pro Asn Pro Ser Phe Ser Pro Thr Pro Gly Phe Thr
1053/281                                   1083/291
CCC ACC CTG GGC TTC AGT CCC GTG CCC AGT TCC ACC TTC ACC TCC AGC TCC ACC TAT ACC
Pro Thr Leu Gly Phe Ser Pro Val Pro Ser Ser Thr Phe Thr Ser Ser Ser Thr Tyr Thr
1113/301                                   1143/311
CCC GGT GAC TGT CCC AAC TTT GCG GCT CCC CGC AGA GAG GTG GCA CCA CCC TAT CAG GGG
Pro Gly Asp Cys Pro Asn Phe Ala Ala Pro Arg Arg Glu Val Ala Pro Pro Tyr Gln Gly
1173/321                                   1203/331
GCT GAC CCC ATC CTT GCG ACA GCC CTC GCC TCC GAC CCC ATC CCC AAC CCC CTT CAG AAG
Ala Asp Pro Ile Leu Ala Thr Ala Leu Ala Ser Asp Pro Ile Pro Asn Pro Leu Gln Lys
```

FIG. 9B

```
1233/341                                    1263/351
TGG GAG GAC AGC GCC CAC AAG CCA CAG AGC CTA GAC ACT GAT GAC CCC GCG ACG CTG TAC
Trp Glu Asp Ser Ala His Lys Pro Gln Ser Leu Asp Thr Asp Asp Pro Ala Thr Leu Tyr
1293/361                                    1323/371
GCC GTG GTG GAG AAC GTG CCC CCG TTG CGC TGG AAG GAA TTC GTG CGG CGC CTA GGG CTG
Ala Val Val Glu Asn Val Pro Pro Leu Arg Trp Lys Glu Phe Val Arg Arg Leu Gly Leu
1353/381                                    1383/391
AGC GAC CAC GAG ATC GAT CGG CTG GAG CTG CAG AAC GGG CGC TGC CTG CGC GAG GCG CAA
Ser Asp His Glu Ile Asp Arg Leu Glu Leu Gln Asn Gly Arg Cys Leu Arg Glu Ala Gln
1413/401                                    1443/411
TAC AGC ATG CTG GCG ACC TGG AGG CGG CGC ACG CCG CGG CGC GAG GCC ACG CTG GAG CTG
Tyr Ser Met Leu Ala Thr Trp Arg Arg Arg Thr Pro Arg Arg Glu Ala Thr Leu Glu Leu
1473/421                                    1503/431
CTG GGA CGC GTG CTC CGC GAC ATG GAC CTG CTG GGC TGC CTG GAG GAC ATC GAG GAG GCG
Leu Gly Arg Val Leu Arg Asp Met Asp Leu Leu Gly Cys Leu Glu Asp Ile Glu Glu Ala
1533/441                                    1563/451
CTT TGC GGC CCC GCC GCC CTC CCG CCC GCG CCC AGT CTT CTC AGA TGA                1580
Leu Cys Gly Pro Ala Ala Leu Pro Pro Ala Pro Ser Leu Leu Arg Stop GGCTGCGCCC CTGCGGGCAG CTCTAAGGAC CGTCCTGCGA      1620
GATCGCCTTC CAACCCCACT TTTTTCTGGA AAGGAGGGGT CCTGCAGGGG CAAGCAGGAG   1680
CTAGCAGCCG CCTACTTGGT GCTAACCCCT CGATGTACAT AGCTTTCTC AGCTGCCTGC   1740
GCGCCGCCGA CAGTCAGCGC TGTGCGCGCG GAGAGAGGTG CGCCGTGGGC TCAAGAGCCT  1800
GAGTGGGTGG TTTGCGAGGA TGAGGGACGC TATGCCTCAT GCCCGTTTTG GGTGTCCTCA  1860
CCAGCAAGGC TGCTCGGGGG CCCCTGGTTC GTCCCTGAGC CTTTTTCACA GTGCATAAGC  1920
AGTTTTTTTT GTTTTTGTTT TGTTTTGTTT TGTTTTTAAA TCAATCATGT TACACTAATA  1980
GAAACTTGGC ACTCCTGTGC CCTCTGCCTG GACAAGCACA TAGCAAGCTG AACTGTCCTA  2040
AGGCAGGGGC GAGCACGGAA CAATGGGGCC TTCAGCTGGA GCTGTGGACT TTTGTACATA  2100
CACTAAAATT CTGAAGTTAA AAAAAAAAAA AAAAGGAATT C                      2141
```

TNF RECEPTORS, TNF BINDING PROTEINS AND DNAS CODING FOR THEM

This application is a continuation of U.S. patent application Ser. No. 08/383,676, filed Feb. 1, 1995, now U.S. Pat. No. 6,294,352, which is a continuation of U.S. Ser. No. 08/153,287, filed Nov. 17, 1993, abandoned, which is a continuation of U.S. Ser. No. 07/821,750, filed Jan. 2, 1992, abandoned, which is a divisional of U.S. Ser. No. 07/511,430, filed Apr. 20, 1990, abandoned, the contents of each of which are incorporated herein by reference. The application also claims priority to foreign patent applications P39 13 101.7, filed Apr. 21, 1989, in Germany; P39 20 282.8, filed Jun. 21, 1989, in Germany; and 90106624.1, filed Apr. 20, 1990, in Europe (EPO).

FIELD OF THE INVENTION

The invention is in the field of recombinant genetics. In particular, the invention relates to a TNF receptor and to a TNF binding protein produced by recombinant means.

BACKGROUND OF THE INVENTION

Tumour necrosis factor (TNF-α) was first found in the serum of mice and rabbits which had been infected with *Bacillus* Calmette-Guerin and which had been injected with endotoxin, and was recognized on the basis of its cytotoxic and antitumor properties (Carswell, E. A., et al., *Proc. Natl. Acad. Sci.* 25:3666-3670 (1975)). It is produced particularly by activated macrophages and monocytes.

Numerous types of cells which are targets of TNF have surface receptors with a high affinity for this polypeptide (Old, L. J., *Nature* 326:330-331 (1987)); it was assumed that lymphotoxin (TNF-β) binds to the same receptor (Aggarwal, B. B., et al., *Nature* 318:655-667 (1985); Gullberg, U., et al., *Eur. J. Haematol.* 39:241-251 (1987)). TNF-α is identical to a factor referred to as cachectin (Beutler, B., et al., *Nature* 316:552-554 (1985)) which suppresses lipoprotein lipase and results in hypertriglyceridaemia in chronically inflammatory and malignant diseases (Torti, F. M. et al., *Nature* 229:867-869 (1985); Mahoney, J. R., et al., *J. Immunol.* 134:1673-1675 (1985)). TNF-α would appear to be involved in growth regulation and in the differentiation and function of cells which are involved in inflammation, immune processes, and hematopoieses.

TNF can have a positive effect on the host organism by stimulating neutrophils (Shalaby, M. R., et al., *J. Immunol.* 135:2069-2073 (1985); Klebanoff, S. J., et al., *J. Immunol.* 136:4220-4225 (1986)) and monocytes and by inhibiting the replication of viruses (Mestan, J., et al., *Nature* 323:816-819 (1986); Wong, G. H. W., et al., *Nature* 323:819-822 (1986)). Moreover, TNF-α activates the immune defenses against parasites and acts directly and/or indirectly as a mediator in immune reactions, inflammatory processes, and other processes in the body, although the mechanisms by which it works have not yet been clarified in a number of cases. However, the administration of TNF-α (Cerami, A., et al., *Immunol. Today* 9:28-31 (1988)) can also be accompanied by harmful phenomena (Tracey, K. J., et al., *Science* 234: 470-474 (1986)) such as shock and tissue damage, which can be remedied by means of antibodies against TNF-α (Tracey, K. J., et al., *Nature* 330:662-666 (1987)).

A number of observations lead one to conclude that endogenously released TNF-α is involved in various pathological conditions. Thus, TNF-α appears to be a mediator of cachexia which can occur in chronically invasive, e.g., parasitic, diseases. TNF-α also appears to play a major part in the pathogenesis of shock caused by gram negative bacteria (endotoxic shock); it would also appear to be implicated in some if not all the effects of lipopolysaccharides (Beutler B., et al., *Ann. Rev. Biochem.* 57:505-18 (1988)). TNF has also been postulated to have a function in the tissue damage which occurs in inflammatory processes in the joints and other tissues, and in the lethality and morbidity of the graft-versus host reaction (GVHR, Transplant Rejection (Piguet, P. F., et al., *Immunobiol.* 175:27 (1987)). A correlation has also been reported between the concentration of TNF in the serum and the fatal outcome of meningococcal diseases (Waage, A., et al., *Lancet* 1:355-357 (1987)).

It has also been observed that the administration of TNF-α over a lengthy period causes a state of anorexia and malnutrition which has symptoms similar to those of cachexia, which accompany neoplastic and chronic infectious diseases (Oliff A., et al., *Cell* 555 63 (1987)).

It has been reported that a protein derived from the urine of fever patients has a TNF inhibiting activity; the effect of this protein is presumed to be due to a competitive mechanism at the level of the receptors (similar to the effect of the interleukin 1 inhibitor (Seckinger, P., et al., *J. Immunol.* 139:1546-1549 (1987); Seckinger P., et al., *J. Exp. Med.,* 1511-16 (1988)).

EP-A2 308 378 describes a TNF inhibiting protein obtained from human urine. Its activity was demonstrated in the urine of healthy and ill subjects and determined on the basis of its ability to inhibit the binding of TNF-α to its receptors on human HeLa cells and FS 11 fibroblasts and the cytotoxic effect of TNF-α on murine A9 cells. The protein was purified until it became substantially homogeneous and characterized by its N-terminus. This patent publication does indeed outline some theoretically possible methods of obtaining the DNA coding for the protein and the recombinant protein itself; however, there is no concrete information as to which of the theoretically possible solutions is successful.

SUMMARY OF THE INVENTION

The invention relates to DNA coding for a TNF receptor protein or a fragment thereof. In particular, the invention relates to DNA coding for the TNF receptor protein having the formula

```
ATG GGC CTC TCC ACC GTG CCT GAC CTG CTG CTG CCA CTG
GTG CTC CTG GAG CTG TTG GTG GGA ATA TAC CCC TCA GGG
GTT ATT GGA CTG GTC CCT CAC CTA GGG GAC AGG GAG AAG
AGA GAT AGT GTG TGT CCC CAA GGA AAA TAT ATC CAC CCT
CAA AAT AAT TCG ATT TGC TGT ACC AAG TGC CAC AAA GGA
ACC TAC TTG TAC AAT GAC TGT CCA GGC CCG GGG CAG GAT
ACG GAC TGC AGG GAG TGT GAG AGC GGC TCC TTC ACC GCT
TCA GAA AAC CAC CTC AGA CAC TGC CTC AGC TGC TCC AAA
TGC CGA AAG GAA ATG GGT CAG GTG GAG ATC TCT TCT TGC
ACA GTG GAC CGG GAC ACC GTG TGT GGC TGC AGG AAG AAC
CAG TAC CGG CAT TAT TGG AGT GAA AAC CTT TTC CAG TGC
```

-continued

```
TTC AAT TGC AGC CTC TGC CTC AAT GGG ACC GTG CAC CTC
TCC TGC CAG GAG AAA CAG AAC ACC GTG TGC ACC TGC CAT
GCA GGT TTC TTT CTA AGA GAA AAC GAG TGT GTC TCC TGT
AGT AAC TGT AAG AAA AGC CTG GAG TGC ACG AAG TTG TGC
CTA CCC CAG ATT GAG AAT GTT AAG GGC ACT GAG GAC TCA
GGC ACC ACA GTG CTG TTG CCC CTG GTC ATT TTC TTT GGT
CTT TGC CTT TTA TCC CTC CTC TTC ATT GGT TTA ATG TAT
CGC TAC CAA CGG TGG AAG TCC AAG CTC TAC TCC ATT GTT
TGT GGG AAA TCG ACA CCT GAA AAA GAG GGG GAG CTT GAA
GGA ACT ACT ACT AAG CCC CTG GCC CCA AAC CCA AGC TTC
AGT CCC ACT CCA GGC TTC ACC CCC ACC CTG GGC TTC AGT
C

-continued

```
asn val pro pro leu arg trp lys glu phe val arg arg leu gly leu ser asp his glu ile asp arg leu glu leu gln asn gly arg cys leu arg glu ala gln tyr ser met leu ala thr trp arg arg arg thr pro arg arg glu ala thr leu glu leu leu gly arg val leu arg asp met asp leu leu gly cys leu glu asp ile glu glu ala leu cys gly pro ala ala leu pro pro ala pro ser leu leu arg (SEQ ID NO: 2)
``` or a fragment thereof which binds to TNF.

The invention also relates to the TNF binding protein of the formula

```
asp ser val cys pro gln gly lys tyr ile his pro gln asn asn ser ile cys cys thr lys cys his lys gly thr tyr leu tyr asn asp cys pro gly pro gly gln asp thr asp cys arg glu cys glu ser gly ser phe thr ala ser glu asn his leu arg his cys leu ser cys ser lys cys arg lys glu met gly gln val glu ile ser ser cys thr val asp arg asp thr val cys gly cys arg lys asn gln tyr arg his tyr trp ser glu asn leu phe gln cys phe asn cys ser leu cys leu asn gly thr val his leu ser cys gln glu lys gln asn thr val cys thr cys his ala gly phe phe leu arg glu asn glu cys val ser cys ser asn cys lys lys ser leu glu cys thr lys leu cys leu pro gln ile glu asn (SEQ ID NO: 4)
``` or a functional derivative or fragment thereof having the ability to bind TNF.

The invention also relates to a process for preparing a recombinant TNF receptor protein, or a functional derivative thereof which is capable of binding to TNF, comprising cultivating a host cell of the invention and isolating the expressed recombinant TNF receptor protein.

The invention also relates to pharmaceutical compositions comprising a TNF receptor protein, or a functional derivative or fragment thereof, and a pharmaceutically acceptable carrier.

The invention also relates to a method for ameliorating the harmful effects of TNF in an animal, comprising administering to an animal in need of such treatment a therapeutically effective amount of a TNF receptor polypeptide, or fragment thereof which binds to TNF.

The invention also relates to a method for the detection of TNF in a biological sample, comprising contacting said sample with an effective amount of a TNF receptor polypeptide, or fragment thereof which binds to TNF, and detecting whether a complex is formed.

DESCRIPTION OF THE FIGURES

FIGS. 1A-1C depict the complete nucleotide sequence (SEQ ID NO: 21) of 1334 bases of the cDNA insert of λ-TNF-BP15 and pTNF-BP15.

FIGS. 6A-6E depict the full nucleotide sequence (SEQ ID NO: 23) of the 6414 bp plasmid pAD-CMV1.

FIGS. 8A-8B depict the complete nucleotide sequence (SEQ ID NO: 24) of raTNF-R8.

FIGS. 9A-9B depict the complete coding region (SEQ ID NO: 26) for human TNF-R in 1TNF-R2.

DETAILED DESCRIPTION OF THE INVENTION

Figure 2:
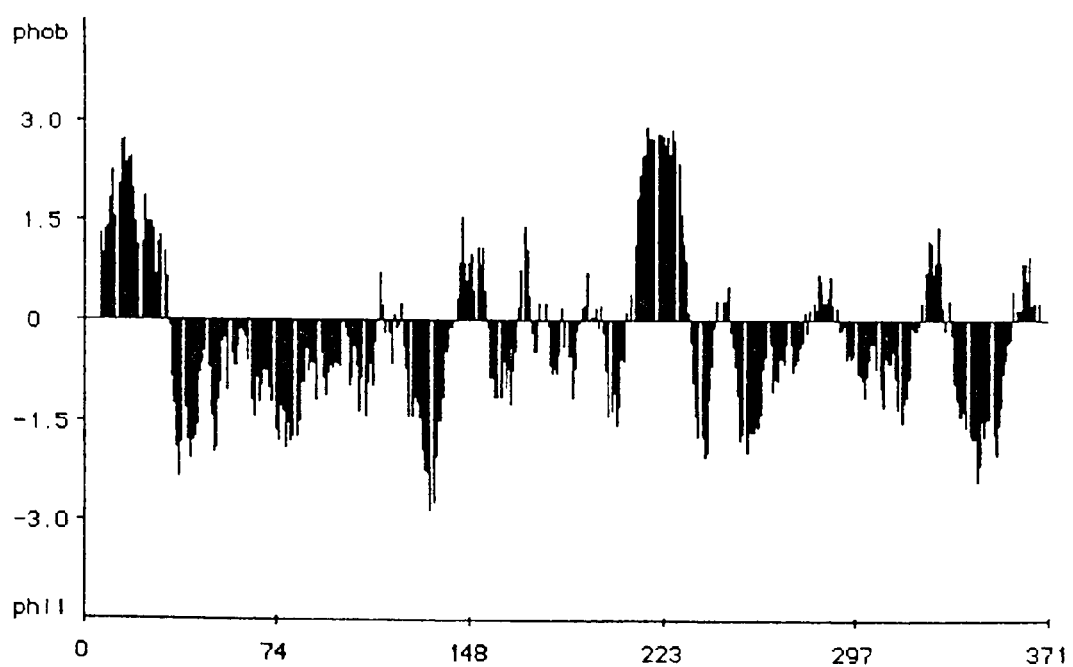
FIG. 2 depicts a hydrophobicity profile which was produced using the Mac Molly program.

In preliminary tests for the purposes of the present invention (see Examples 1-4), a protein was identified from the dialyzed urine of uraemia patients, and this protein inhibits the biological effects of TNF-α by interacting with TNF-α to prevent it from binding to its cell surface receptor (Olsson I., et al., Eur. J. Haematol. 41:414-420 (1988)). This protein was also found to have an affinity for TNF-β.

The presence of this protein (hereinafter referred to as TNF-BP) in concentrated dialyzed urine was detected by competition with the binding of radioactively labeled recombinant TNF-α to a subclone of HL-60 cells, by measuring the influence of dialyzed urine on the binding of $^{125}$I-TNF-α to the cells. The binding tests carried out showed a dosage dependent inhibition of TNF-α binding to the cells by concentrated dialyzed urine (the possible interpretation that the reduction in binding observed might be caused by any TNF-α present in the urine or by TNF-β competing for the binding, was ruled out by the discovery that the reduction in binding could not be remedied by the use of TNF-α and TNF-β antibodies).

Analogously, in preliminary tests for the purposes of the present invention, it was demonstrated that TNF-BP also shows an affinity for TNF-β, which is about 1/50 of its affinity for TNF-α.

Gel chromatography on Sephacryl 200 showed that a substance in the urine and serum of dialysis patients and in the serum of healthy subjects forms a complex with recombinant TNF-α with a molecular weight of about 75,000.

TNF-BP was concentrated 62 times from several samples of dialyzed urine from uraemia patients by partial purification using pressure ultrafiltration, ion exchange chromatography, and gel chromatography.

The preparations obtained were used to detect the biological activity of TNF-BP by inhibiting the growth-inhibiting effect of TNF-α on HL-60-10 cells. TNF-BP was found to have a dosage dependent effect on the biological activity of TNF-α. The binding characteristics of cells were also investigated by pretreatment with TNF-BP and an exclusive competition binding test. It was shown that pretreatment of the cells with TNF-BP does not affect the binding of TNF-α to the cells. This indicates that the effect of TNF-BP is not based on any binding to the cells and competition with TNF-α for the binding to the receptor.

The substantially homogeneous protein is obtained in highly purified form by concentrating urine from dialysis patients by ultrafiltration, dialyzing the concentrated urine, and concentrating it four-fold in a first purification step using DEAE sephacel chromatography. Further concentration was carried out by affinity chromatography using sepharose-bound TNF-α. The final purification was carried out using reverse phase chromatography (FPLC).

It was shown that the substantially highly purified protein inhibits the cytotoxic effect of TNF-α on WEHI 164 clone 13 cells (Olsson et al., *Eur. J. Haematol.* 42:270-275 (1989)).

The N-terminal amino acid sequence of the substantially highly purified protein was analyzed. It was found to be Asp-Ser-Val-Xaa-Pro-Gln-Gly-Lys-Tyr-Ile-His-Pro-Gln (main sequence; SEQ ID NO: 28); the following N-terminal sequence was detected in traces: Leu-(Val)-(Pro)-(His)-Leu-Gly-Xaa-Arg-Glu (subsidiary sequence; SEQ ID NO: 29). A comparison of the main sequence with the Nterminal sequence of the TNF-inhibiting protein disclosed in EP-A2 308 378 shows that the two proteins are identical.

The following amino acid composition was found, given in mols of amino acid per mol of protein and in mol % of amino acid, measured as the average of 24-hour and 48-hour hydrolysis:

|  | Mol of amino acid/ mol of protein | mol % amino acid |
| --- | --- | --- |
| Asp + Asn | 27.5 | 10.9 |
| Thr | 15.8 | 6.3 |
| Ser | 20.7 | 8.2 |
| Glu + Gln | 35.0 | 13.8 |
| Pro | 9.5 | 3.8 |
| Gly | 16.0 | 6.3 |
| Ala | 4.2 | 1.7 |
| Cys | 32.3 | 12.8 |
| Val | 10.8 | 4.3 |
| Met | 1.1 | 0.4 |
| Ile | 7.0 | 2.8 |
| Leu | 20.2 | 8.0 |
| Tyr | 6.1 | 2.4 |
| Phe | 8.1 | 3.2 |
| His | 11.1 | 4.4 |
| Lys | 15.7 | 6.2 |
| Arg | 11.8 | 4.7 |
| Total | 252.9 | 100 |

A content of glucosamine was detected by amino acid analysis. The results of an affinoblot carried out using Concanavalin A and wheatgerm lectin also showed that TNF-BP is a glycoprotein.

The substantially homogeneous protein was digested with trypsin and the amino acid sequences of 17 of the cleavage peptides obtained were determined. The C-terminus was also analyzed.

TNF-BP obviously has the function of a regulator of TNF activity with the ability to buffer the variations in concentration of free, biologically active TNF-α. TNF-BP should also affect the secretion of TNF by the kidneys because the complex formed with TNF, the molecular weight of which was measured at around 75,000 by gel permeation chromatography on Sephadex G 75, is obviously not retained by the glomerulus, unlike TNF. The TNF-BP was detected in the urine of dialysis patients as one of three main protein components which have an affinity for TNF and which are eluted together with TNF-BP from the TNF affinity chromatography column. However, the other two proteins obviously bind in a manner which does not affect the binding of TNF-α to its cell surface receptor.

The results obtained regarding the biological activity of TNF-BP, in particular the comparison of the binding constant with the binding constant described for the TNF receptor (Creasey, A. A., et al., *Proc. Natl. Acad. Sci.* 84:3293-3297 (1987)), provided a first indication that this protein might be the soluble part of a TNF receptor.

In view of its ability to inhibit the biological activity of TNF-α and TNF-β, the TNF binding protein is suitable for use in cases where a reduction in the TNF activity in the body is indicated. Functional derivatives or fragments of the TNF binding protein with the ability to inhibit the biological activity of TNF are also suitable for use in such cases.

Covalent modifications of the TNF binding proteins of the present invention are included within the scope of this invention. Variant TNF binding proteins may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'-N=C=N-R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the TNF binding proteins to water-insoluble support matrices or surfaces for use in the method for cleaving TNF binding protein-fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3' dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W. H. Freeman & Co., San Francisco, pp. 79-86 (1983)), acetylation of the N-terminal amine, and, in some instances, amidation of the C-terminal carboxyl groups.

Amino acid sequence variants of the TNF binding proteins can also be prepared by mutations in the DNA. Such variants include, for example, deletions from, or insertions or substitutions of, residues within the amino acid sequence shown in the Figures. Any combination of deletion, insertion, and substitution may also be made to arrive at the final construct, provided that the final construct possesses the desired activity (binding to TNF). Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the TNF binding proteins, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed TNF binding protein variants screened for the optimal combination of desired activity. Techniques for making substitution mutations at predetermined sites in DNA having a known sequence are well known, for example, site-specific mutagenesis.

Preparation of a TNF binding protein variant in accordance herewith is preferably achieved by site-specific mutagenesis of DNA that encodes an earlier prepared variant or a nonvariant version of the protein. Site-specific mutagenesis allows the production of TNF binding protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (*USA*) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bear the desired mutation. This heteroduplex vector is then used to transform appropriate cells such as JM101 cells, and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions may generally range from about 1 to 30 residues or 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete hormone receptor molecule sequence) may range generally from about 1 to 10 or 1 to 5 residues. An example of a terminal insertion includes a fusion of a signal sequence, whether heterologous or homologous to the host cell, to the N-terminus of the TNF binding protein to facilitate the secretion of mature TNF binding protein from recombinant hosts.

The third group of variants are those in which at least one amino acid residue in the TNF binding protein, and preferably, only one, has been removed and a different residue inserted in its place. Such substitutions preferably are made in accordance with the following Table 1 when it is desired to modulate finely the characteristics of a hormone receptor molecule.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the TNF binding protein. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the TNF binding protein-encoding nucleic acid, expression of the variant nucleic acid in recombinant cell culture, and, optionally, purification from the cell culture, for example, by immunoaffinity adsorption on a polyclonal anti-TNF binding protein column (to absorb the variant by binding it to at least one remaining immune epitope).

The activity of the cell lysate or purified TNF binding protein variant is then screened in a suitable screening assay for the desired characteristic. For example, a change in the binding affinity for TNF or immunological character of the TNF binding protein, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

TNF-BP (or the functional derivatives, variants, and active fragments thereof) may be used for the prophylactic and therapeutic treatment of the human or animal body in indications where TNF-α has a harmful effect. Such diseases include in particular inflammatory and infectious and parasitic diseases or states of shock in which endogenous TNF-α is released, as well as cachexia, GVHR, ARDS (Adult Respiratory Distress Symptom) and autoimmune diseases such as rheumatoid arthritis, etc. Also included are pathological conditions which may occur as side effects of treatment with TNF-α, particularly at high doses, such as severe hypotension or disorders of the central nervous system.

In view of its TNF binding properties, TNF-BP is also suitable as a diagnostic agent for determining TNF-α and/or TNF-β, e.g., as one of the components in radioimmunoassays or enzyme immunoassays, optionally together with antibodies against TNF.

In view of its properties, this protein is a pharmacologically useful active substance which cannot be obtained in sufficient quantities from natural sources using protein-chemical methods.

There was therefore a need to produce this protein (or related proteins with the ability to bind TNF) by recombinant methods in order that it could be made available in sufficient amounts for therapeutic use. The phrase "ability to bind TNF" within the scope of the present invention means the ability of a protein to bind to TNF-α in such a way that TNF-α is prevented from binding to the functional part of the receptor and the activity of TNF-α in humans or animals is inhibited or prevented altogether. This definition also includes the ability of a protein to bind to other proteins, e.g., to TNF-β, and inhibit their effect.

The aim of the present invention was to provide the DNA which codes for TNF-BP, in order to make it possible, on the basis of this DNA, to produce recombinant DNA molecules by means of which suitable host organisms can be transformed, with the intention of producing TNF-BP or functional derivatives and fragments thereof.

Within the scope of this objective, it was also necessary to establish whether TNF-BP is the soluble part of a TNF receptor. This assumption was confirmed, thus providing the basis for clarification of the receptor sequence.

Another objective within the scope of the present invention was to prepare the cDNA coding for a TNF receptor, for the purpose of producing recombinant human TNF receptor.

The presence of a specific receptor with a high affinity for TNF-α on various cell types was shown by a number of working groups. Recently, the isolation and preliminary characterization of a TNF-α receptor was reported for the first time (Stauber, G. B., et al., *J. Biol. Chem.* 263:19098-19104 (1988)). Since the binding of radioactively labeled TNF-α can be reversed by an excess of TNF-β (Aggarwal, B. B., et al., *Nature* 318:655-667 (1985)), it was proposed that TNF-α and TNF-β share a common receptor. On the other hand, since it was shown that certain cell types which respond to TNF-α are wholly or partly insensitive to TNF-β (Locksley, R. M., et al., *J. Imunol.* 139:1891-1895 (1987)), the existence of a common receptor was thrown into doubt again.

By contrast, recent results on the binding properties of TNF-β to receptors appear to confirm the theory of a common receptor (Stauber, G. B., et al., *J. Biol. Chem.* 264:3573-3576 (1989)), and this study proposes that there are differences between TNF-α and TNF-β in their interaction with the receptor or in addition with respect to the events which occur in the cell after the ligand-receptor interaction. Lately, there has been a report of another TNF-binding protein which is presumed to be the soluble form of a different TNF receptor (Engelmann et al., *J. Biol. Chem.* 265:1531-1536 (1990)). The availability of the DNA coding for a TNF receptor is the prerequisite for the production of recombinant receptor and consequently makes it much easier to carry out comparative investigations on different types of cell regarding their TNF-α and/or TNF-β receptors or the reactions triggered by the binding of TNF to the receptor in the cell. It also makes it possible to clarify the three-dimensional structure of the receptor and hence provide the prerequisite for a rational design for the development of agonists and antagonists for the TNF activity.

The efforts to solve the problem of the invention started from the finding that major difficulties are occasionally encountered when searching through cDNA libraries using hybridizing probes derived from amino acid sequences of short peptides, on account of the degeneration of the genetic code. In addition, this procedure is made more difficult when the researcher does not know in which tissue a particular protein, e.g., TNF BP, is synthesized. In this case, should the method fail, it is not always possible to tell with any certainty whether the cause of the failure was the choice of an unsuitable cDNA library or the insufficient specificity of the hybridization probes.

Therefore, the following procedure was used according to the invention in order to obtain the DNA coding for TNF-BP:

The cDNA library used was a library of the fibrosarcoma cell line HS913 T which had been induced with TNF-α and was present in λ gt11. In order to obtain λ DNA with TNF-BP sequences from this library, the high degree of sensitivity of the polymerase chain reaction (PCR; Saiki, R. X., *Science* 239:487-491 (1988)) was used. Using this method it is possible to obtain, from an entire cDNA library, an unknown DNA sequence flanked by oligonucleotides which have been designed on the basis of known amino acid partial sequences and used as primers. A longer DNA fragment of this kind can subsequently be used as a hybridization probe, e.g., in order to isolate cDNA clones, particularly the original cDNA clone.

On the basis of the N-terminal amino acid sequence (main sequence) and amino acid sequences of tryptic peptides obtained from highly purified TNF-BP, hybridization probes were prepared. Using these probes, a cDNA which constitutes part of the cDNA coding for TNF-BP was obtained by PCR from the cDNA library HS913T.

This cDNA has the following nucleotide sequence:

```
CAG GGG AAA TAT ATT CAC CCT CAA AAT AAT TCG ATT TGC

TGT ACC AAG TGC CAC AAA GGA ACC TAC TTG TAC AAT GAC

TGT CCA GGC CCG GGG CAG GAT ACG GAC TGC AGG GAG TGT
```

-continued
```
GAG AGC GGC TCC TTC ACA GCC TCA GAA AAC AAC AAG
```

(SEQ ID NO: 30).

This DNA is one of a number of possible variants which are suitable for hybridizing with TNF-BP DNAs or TNF-BP-RNAs (these variants include, for example, those DNA molecules which are obtained by PCR amplification with the aid of primers, wherein the nucleotide sequence does not coincide precisely with the desired sequence, possibly as a result of restriction sites provided for cloning purposes or because of amino acids which were not clearly identified in the amino acid sequence analysis). "TNF-BP-DNAs" and "TNF-BP RNAs" indicate nucleic acids which code for TNF-BP or related proteins with the ability to bind TNF or which contain a sequence coding for such a protein.

TNF-BP DNAs (or TNF-BP-RNAs) also include cDNAs derived from mRNAs which are formed by alternative splicing (or these mRNAs themselves). The phrase "alternative splicing" means the removal of introns, using splice acceptor and/or splice donor sites which are different from the same mRNA precursor. The mRNAs thus formed differ from one another by the total or partial presence or absence of certain exon sequences, and in some cases there may be a shift in the reading frame.

The cDNA (or variants thereof) initially obtained according to the invention, containing some of the sequence coding for TNF-BP, can thus be used as a hybridization probe in order to obtain cDNA clones containing TNF-BP DNAs from cDNA libraries. It may also be used as a hybridization probe for mRNA preparations, for isolating TNF-BP RNAs and for producing concentrated cDNA libraries therefrom, for example, to allow much simpler and more efficient screening. A further field of application is the isolation of the desired DNAs from genomic DNA libraries using these DNAs as hybridization probes.

The DNA defined hereinbefore (or a variant thereof) is capable of hybridizing with DNAs (or RNAs) which code for TNF-BP or contain the sequence which codes for TNF-BP. Using this DNA as a probe, it is also possible to obtain cDNAs which code for proteins, the processing of which yields TNF-BP. The term "processing" means the splitting off of partial sequences in vivo. This might mean, at the N-terminus the signal sequence and/or other sequences and possibly also at the C-terminus, the transmembrane and cytoplasmic region of the receptor. Using this hybridization signal it is therefore possible to search through suitable cDNA libraries to look for any cDNA which contains the entire sequence coding for a TNF receptor (if necessary, this operation may be carried out in several steps).

According to the invention, the cDNA of the sequence defined hereinbefore, which had been obtained by PCR from the cDNA library of the TNF-α induced fibrosarcoma cell line HS913 T (in λ gt11), was used to search through the cDNA library once more, the lambda DNA was excised from the hybridizing clones, subcloned, and sequenced. A 1334 base long cDNA insert was obtained which contains the sequence coding for TNF-BP.

Thus, first of all, DNAs were prepared, coding for a polypeptide capable of binding TNF, or for a polypeptide in which this TNF binding protein is a partial sequence. These DNAs also include DNAs of the kind which code for parts of these polypeptides.

The complete nucleotide sequence of the longest cDNA insert obtained is shown in FIGS. 1A-1C.

This nucleotide sequence has a continuous open reading frame beginning with base 213 up to the end of the 1334 bp long cDNA insert. Since there is a stop codon (TAG) in the same reading frame 4 codons before the potential translation start codon ATG (213-215), it was assumed that the start codon is actually the start of translation used in vivo.

A comparison of the amino acid sequence derived from the nucleotide sequence with the amino acid sequences determined from the amino terminal end of TNF-BP and tryptic peptides, shows a high degree of conformity. This means that the isolated cDNA contains the sequence coding for authentic TNF-BP.

Starting from the N-terminus, the first sequence which shows conformity with a tryptic cleavage peptide sequence is the sequence from fraction 12 (Leu-Val-Pro- . . . ), which had also been obtained as a subsidiary sequence in the analysis of the N-terminus of TNF-BP. This N-terminal leucine corresponds to the 30th amino acid in the cDNA sequence. Since the preceding section of 29 amino acids has a strongly hydrophobic nature and TNF-BP is a secreted protein, it can be concluded that these 29 amino acids constitute the signal peptide required for the secretion process, which is split off during secretion (designated S1-S29 in FIG. 1A). The amino acid sequence obtained as the main sequence in the N-terminal analysis of TNF-BP corresponds to the amino acids beginning with Asp-12 in the cDNA sequence. This aspartic acid group directly follows the basic dipeptide Lys-Arg. Since a very large number of proteins are cleaved proteolytically in vivo after this dipeptide, it can be assumed that TNF-BP with N-terminal Asp is not formed directly by the processing of a precursor in the secretion process, but that the N-terminal 11 amino acids are split off from the processed protein at a later time by extracellular proteases. The carboxy-terminal end of TNF-BP had been determined as Ile Glu-Asn (C-terminal analysis; tryptic peptide fraction 27: amino acids 159-172, tryptic peptide fraction 21: amino acids 165-172), Asn corresponding to position 172 in the cDNA sequence.

Potential N-glycosylation sites of general formula Asn-Xaa-Ser/Thr, in which Xaa may be any amino acid other than proline, are located at positions 25-27 (Asn-Asn-Ser), 116-118 (Asn-Cys-Ser), and 122-124 (Asn-Gly-Thr) of the TNF-BP cDNA sequence. The fact that Asn-25 is glycosylated is clear from the fact that Asn could not be identified in the sequencing of the corresponding tryptic cleavage peptide at this site.

Analysis of the nucleotide sequence or the amino acid sequence derived therefrom in conjunction with the protein-chemical investigations carried out shows that TNF-BP is a glycosylated polypeptide with 172 amino acids, which is converted by proteolytic cleaving after the 11th amino acid into a glycoprotein with 161 amino acids. The following Table shows the tryptic peptides sequenced and the corresponding amino acid sequences derived from the cDNA sequence:

| Fraction | Amino acids |
|---|---|
| 12 | 1-8 |
| 1 | 12-19 |
| 8 | 20-32 |
| 14/I | 36-48 |
| 20 | 36-53 |
| 11 | 54-67 |
| | (Amino acids 66-67 had not been correctly determined on the peptide) |
| 14/II | 79-91 |
| 26 | 133-146 |
| 5 | 147-158 |
| 27 | 159-172 |

The cDNA obtained is the prerequisite for the preparation of recombinant TNF-BP.

As already mentioned, the cDNA initially isolated according to the invention does not contain the stop codon which could have been expected from analysis of the C-terminus after the codon for Asn-172, but the open reading frame is continued. The region between Val-183 and Met-204 is strongly hydrophobic by nature. This hydrophobic region of 22 amino acids followed by a portion containing positively charged amino acids (Arg-206, Arg-209) has the typical features of a transmembrane domain which anchors proteins in the cell membrane. The protein fraction following in the C-terminus direction, on the other hand, is strongly hydrophilic.

The hydrophobicity profile is shown in FIG. 2 (the hydrophobicity plot was produced using the MacMolly program; Soft Gene Berlin); the window size for calculating the values was 11 amino acids. Hydrophobic regions correspond to positive values and hydrophilic regions to negative values on the ordinates. The abscissa shows the number of amino acids beginning with the start methionine S1).

The protein structure shows that the DNA coding for the soluble TNF-BP secreted is part of a DNA coding for a larger protein; this protein has the feature of a protein anchored in the cell membrane, contains TNF-BP in a manner typical of extracellular domains and has a substantial portion which is typical of cytoplasmatic domains. Soluble TNF-BP is obviously obtained from this membrane-bound form by proteolytic cleaving just outside the transmembrane domain.

The structure of the protein coded by the cDNA obtained in conjunction with the ability of TNF-BP to bind TNF confirms the assumption that TNF-BP is part of a cellular surface receptor for TNF the extracellular domains of which, responsible for the binding of TNF, can be cleaved proteolytically and retrieved in the form of the soluble TNF-BP. The possibility should not be ruled out that, with regard to the operating capacity of the receptor, this protein may possibly be associated with one or more other proteins.

For the purposes of the production of TNF-BP on a larger scale, it is advantageous not to start from the whole cDNA, since the need to cleave TNF-BP from that part of the protein which represents the membrane-bound part of the TNF receptor must be borne in mind. Rather, as mentioned hereinbefore, a translation stop codon is expediently inserted after the codon for Asn-172 by controlled mutagenesis in order to prevent protein synthesis going beyond the C-terminal end of TNF-BP. With the cDNA which is initially obtained according to the invention and which represents a partial sequence of the DNA coding for a TNF receptor, it is possible to obtain the complete receptor sequence by amplifying the missing 3'-end, e.g., by means of modified PCR (RACE="rapid amplification of cDNA ends"; Frohman, M. A., et al., *Proc. Natl. Acad. Sci.* 85:8998-9002 (1988)), with the aid of a primer constructed on the basis of a sequence located as far as possible in the direction of the 3'-end of the cDNA present. An alternative method is the conventional screening of the cDNA library with the available cDNA or parts thereof as a probe.

According to the invention, first of all, the rat TNF receptor cDNA was isolated and with a partial sequence therefrom the complete human TNF receptor cDNA was obtained and brought to expression.

The invention relates to a human TNF receptor and the DNA coding for it. This definition also includes DNAs which code for C- and/or N-terminally shortened, e.g., processed forms or for modified forms (e.g., by changes at proteolytic cleavage sites, glycosylation sites or specific domain regions) or for fragments, e.g., the various domains, of the TNF receptor. These DNAs may be used in conjunction with the control sequences needed for expression as a constituent of recombinant DNA molecules, to which the present invention also relates, for transforming prokaryotic or eukaryotic host organisms. On the one hand this creates the prerequisite for preparing the TNF receptor or modifications or fragments thereof in larger quantities by the recombinant method, in order to make it possible for example to clarify the three-dimensional structure of the receptor. On the other hand, these DNAs can be used to transform higher eukaryotic cells in order to allow a study of the mechanisms and dynamics of the TNF/receptor interaction, signal transmission or the relevance of the various receptor domains or sections thereof.

The present invention encompasses the expression of the desired TNF binding protein in either prokaryotic or eukaryotic cells. Preferred eukaryotic hosts include yeast (especially *Saccharomyces*), fungi (especially *Aspergillus*), mammalian cells (such as, for example, human or primate cells) either in vivo or in tissue culture.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-Kl, and their derivatives. For a mammalian host, several possible vector systems are available for the expression of the desired TNF binding protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired TNF binding protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* (London) 290: 304-310 (1981)); the yeast qa14 gene promoter (Johnston, S. A., et al., *Proc. Natl. Acad. Sci.* (*USA*) 79:6971-6975 (1982); Silver, P. A., et al., *Proc. Natl. Acad. Sci.* (*USA*) 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule-encoding DNA sequence) or a frame-shift mutation (if the AUG codon is not in the same reading frame as the desired TNF binding protein-encoding sequence).

The expression of the TNF binding proteins can also be accomplished in procaryotic cells. Preferred prokaryotic hosts include bacteria such as *E. coli, Bacillus, Streptomyces, Pseudomonas, Salmonella, Serratia*, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F, lambda, prototrophic; ATCC 27325), and other enterobacteria (such as *Salmonella typhimurium* or *Serratia marcescens*), and various *Pseudomonas* species. The prokaryotic host must be compatible with the replicon and control sequences in the expression plasmid.

To express the desired TNF binding protein in a prokaryotic cell (such as, for example, *E. coli, B. subtilis, Pseudomonas, Streptomyces*, etc.), it is necessary to operably link the desired receptor molecule-encoding sequence to a functional prokaryotic promoter. Such promoters may be either constitutive or, more preferably, regulatable (i.e., inducible or derepressible). Examples of constitutive promoters include the int promoter of bacteriophage λ and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the α-amylase (Ulmanen, I., et al., *J. Bacteriol.* 162: 176-182 (1985)), the σ-28-specific promoters of *B. subtilis* (Gilman, M. Z., et al., *Gene* 32:11-20 (1984)), the promoters of the bacteriophages of *Bacillus* (Gryczan, T. J., In: *The Molecular Biology of the Bacilli*, Academic Press, Inc., NY (1982)), and *Streptomyces* promoters (Ward, J. M., et al., *Mol. Gen. Genet.* 203:468-478 (1986)). Prokaryotic promoters are reviewed by Click, B. R., (*J. Ind. Microbiol.* 1:277-282 (1987)); Cenatiempo, Y. (*Biochimie* 68:505-516 (1986)); and Gottesman, S. (*Ann. Rev. Genet.* 18:415-442 (1984)).

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365-404 (1981)).

The desired TNF binding protein-encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP, and YRP, etc., or their derivatives. Such plasmids are well known in the art (Botstein, D., et al., *Miami Wntr. Symp.* 19:265-274 (1982); Broach, J. R., In: The Molecular Biology of the Yeast *Saccharomyces*: Life Cycle and Inheritance, Cold Spring Harbor Laboratory, Cold Spring Harbor, N.Y., pp. 445-470 (1981); Broach, J. R., *Cell* 28:203-204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper, or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Preferred prokaryotic vectors include plasmids such as those capable of replication in *E. coli*, such as, for example, pBR322, ColE1, pSC101, pACYC 184, and πVX. Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, and pT127, etc. Such plasmids are disclosed by Gryczan, T. (In: *The Molecular Biology of the Bacilli*, Academic Press, NY (1982), pp. 307-329). Suitable *Streptomyces* plasmids include pIJ101 (Kendall, K. J., et al., *J. Bacteriol.* 169:4177-4183 (1987)), and *Streptomyces* bacteriophages such as φC31 (Chater, K. F., et al., In: *Sixth International Symposium on Actinomycetales Biology*, Akademiai Kaido, Budapest, Hungary (1986), pp. 45-54). *Pseudomonas* plasmids are reviewed by John, J. F., et al. (*Rev. Infect. Dis.* 8:693-704 (1986)), and Izaki, K. (*Jpn. J. Bacteriol.* 33:729-742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation, or other conventional techniques. After the fusion, the cells are grown in media and screened for appropriate activities. Expression of the sequence results in the production of the TNF binding protein.

The TNF binding proteins of the invention may be isolated and purified from the above-described recombinant molecules in accordance with conventional methods, such as extraction, precipitation, chromatography, affinity chromatography, electrophoresis, or the like. The term "substantially pure" is intended to mean TNF binding proteins which are substantially one major band by SDS-polyacrylamide gel electrophoresis and which contain only minor amounts of other proteins which would normally contaminate a whole cell lysate containing native TNF receptor protein, as evidenced by the presence of other minor bands.

The recombinant TNF receptor (or fragments or functional derivatives thereof) can be used to investigate substances for their interaction with TNF or the TNF receptor or their influence on the signal transmission induced by TNF. Such screenings (using proteins/fragments/variants or suitably transformed higher eukaryotic cells) create the prerequisite for the identification of substances which substitute TNF, inhibit the binding thereof to the receptor or those which are capable of blocking or intensifying the mechanism of signal transmission initiated by TNF.

One possible method of discovering agonists and antagonists of TNF or the TNF receptor is in the establishment of high capacity screening. A suitable cell line, preferably one which does not express endogenous human TNF receptor, is transformed with a vector which contains the DNA coding for a functional TNF receptor and optionally modified from the natural sequence. The activity of agonists or antagonists can be investigated in screening of this kind by monitoring the response to the interaction of the substance with the receptor using a suitable reporter (altered enzyme activity, e.g., protein kinase C, or gene activation, e.g., manganese superoxide dismutase, NF-KB). Investigations into the mechanisms and dynamics of the TNF/receptor interaction, signal transmission, or the role of the receptor domains in this respect may also be carried out, for example, by combining DNA fractions coding for the extracellular domain of the TNF receptor (or parts thereof) with DNA fractions coding for various transmembrane domains and/or various cytoplasmatic domains and bringing them to expression in eukaryotic cells. The hybrid expression products which may be obtained in this way may be capable of giving conclusive information as to the relevance of the various receptor domains, on the basis of any changes in the properties for signal transduction, so that targeted screening is made easier.

The availability of the cDNA coding for the TNF receptor or fractions thereof is the prerequisite for obtaining the genomic DNA. Under stringent conditions, a DNA library is screened and the clones obtained are investigated to see whether they contain the regulatory sequence elements needed for gene expression in addition to the coding regions (e.g., checking for promoter function by fusion with coding regions of suitable reporter genes). Methods for screening DNA libraries under stringent conditions are taught, for example, in EP-A 0 174 143, incorporated by reference herein. Obtaining the genomic DNA sequence makes it possible to investigate the regulatory sequences situated in the area which does not code for the TNF receptor, particularly in the 5'-flanking region, for any possible interaction with known substances which modulate gene expression, e.g., transcription factors or steroids, or possibly discover new substances which might have a specific effect on the expression of this gene. The results of such investigations provide the basis for the targeted use of such substances for modulating TNF receptor expression and hence for directly influencing the ability of the cells to interact with TNF. As a result, the specific reaction with the ligands and the resulting effects can be suppressed.

The scope of the present invention also includes DNAs which code for subtypes of the TNF receptor or its soluble forms, which may possibly have properties different from those of the present TNF receptor. These are expression products which are formed by alternative splicing and have modified structures in certain areas, e.g., structures which can bring about a change in the affinity and specificity for the ligand (TNF-α/TNF-β) or a change in terms of the nature and efficiency of signal transmission.

With the aid of the cDNA coding for the TNF receptor it is possible to obtain nucleic acids which hybridize with the cDNA or fragments thereof under conditions of low stringency and code for a polypeptide capable of binding TNF or contain the sequence coding for such a polypeptide.

According to a further aspect the invention relates to recombinant TNF-BP, preferably in a secretable form, which constitutes the soluble part of the TNF receptor according to the invention, and the DNA coding for it. By introducing a DNA construct containing the sequence coding for TNF-BP with a sequence coding for a signal peptide under the control of a suitable promoter into suitable host organisms, especially eukaryotic and preferably higher eukaryotic cells, it is possible to produce TNF-BP which is secreted into the cell supernatant.

If a signal peptide is used with regard to the secretion of the protein, the DNA coding for the signal peptide is conveniently inserted before the codon for Asp-12 in order to obtain a uniform product. Theoretically, any signal peptide is suitable which guarantees secretion of the mature protein in the corresponding host organism. If necessary, the signal sequence can also be placed in front of the triplet coding for Leu-1; in this case, it may be necessary to separate the form of TNF-BP produced by splitting off the peptide which consists of 11 amino acids at the N-terminus, from the unprocessed or incompletely processed TNF-BP in an additional purification step.

Since the cDNA after the codon for Asn-172, which represents the C-terminus on the basis of C-terminal analysis, does not contain a stop codon, a translation stop codon is expediently introduced, with respect to the expression of TNF-BP, after the codon for Asn-172, by controlled mutagenesis.

The DNA coding for TNF-BP can be modified by mutation, transposition, deletion, addition, or truncation provided that DNAs modified in this way code for (poly)peptides capable of binding TNF. Such modifications may consist, for example, of changing one or more of the potential glycosylation sites which are not necessary for the biological activity, e.g., by replacing the Asn codon by a triplet which codes for a different amino acid. With a view to maintaining the biological activity, modifications which result in a change in the disulfide bridges (e.g., a reduction in their number) may also be carried out.

The DNA molecules referred to thus constitute the prerequisite for constructing recombinant DNA molecules, which are also an object of the invention. With recombinant DNA molecules of this kind in the form of expression vectors containing the DNA, optionally suitably modified, which codes for a protein with TNF-BP activity, preferably with a preceding signal sequence, and the control sequences needed for expression of the protein, it is possible to transform and cultivate suitable host organisms and obtain the protein.

Just like any modifications to the DNA sequence, host cells or organisms suitable for expression are selected particularly with regard to the biological activity of the protein in binding TNF. Furthermore, the criteria which are conventionally applied to the preparation of recombinant proteins such as compatibility with the chosen vector, processability, isolation of the protein, expression characteristics, safety, and cost aspects are involved in the decision as to the host organism. The choice of a suitable vector arises from the host intended for transformation. In principle, all vectors which replicate and express the DNAs (or modifications thereof) coding for TNF-BP according to the invention are suitable.

With respect to the biological activity of the protein, in the expression of the DNA coding for TNF-BP, particular account should be taken of any relevance of the criteria, found in the natural protein, of glycosylation and a high proportion of cysteine groups to the property of binding TNF. Conveniently, therefore, eukaryotes, particularly suitable expression systems of higher eukaryotes, are used for the expression.

Within the scope of the present invention, both transient and permanent expression of TNF-BP were demonstrated in eukaryotic cells.

The recombinant TNF-BP according to the invention and suitable modifications thereof which have the capacity to bind TNF can be used in the prophylactic and therapeutic treatment of humans and animals for indications in which a harmful effect of TNF-α occurs. Since TNF-BP has also been shown to have a TNF-β inhibiting activity, it (or the associated or modified polypeptides) can be used in suitable doses, possibly in a form modified to give a greater affinity for TNF-β, to inhibit the effect of TNF-β in the body.

The invention therefore also relates to pharmaceutical preparations containing a quantity of recombinant TNF-BP which effectively inhibits the biological activity of TNF-α and/or TNF-[β, or a related polypeptide capable of binding TNF.

Pharmaceutical preparations are particularly suitable for parenteral administration for those indications in which TNF displays a harmful effect, e.g., in the form of lyophilized preparations or solutions. These contain TNF-BP or a therapeutically active functional derivative thereof in a therapeutically active amount, optionally together with physiologically acceptable additives such as stabilizers, buffers, and preservatives, etc.

The dosage depends particularly on the indication and the specific form of administration, e.g., whether it is administered locally or systemically. The size of the individual doses will be determined on the basis of an individual assessment of the particular illness, taking into account such factors as the patient's general health, anamnesis, age, weight, and sex, etc. It is essential when determining the therapeutically effective dose to take into account the quantity of TNF secreted which is responsible for the disease as well as the quantity of endogenous TNF-BP. Basically, it can be assumed that, for effective treatment of a disease triggered by TNF, at least the same molar amount of TNF-BP is required as the quantity of TNF secreted, and possibly a multiple excess might be needed.

More specifically, the objective of the invention is achieved as follows:

The N-terminal amino acid sequence of the highly purified TNF-BP and the amino acid sequences of peptides obtained by tryptic digestion of the protein can be determined.

Moreover, the C-terminus was determined by carboxypeptidase P digestion, derivatization of the amino acids split off and chromatographic separation. From the peptide sequences obtained by tryptic digestion, with a view to their use in PCR for the preparation of oligonucleotides, regions were selected from the N-terminus on the one hand and from a tryptic peptide on the other hand such that the complexity of mixed oligonucleotides for hybridization with cDNA is kept to a minimum. A set of mixed oligonucleotides were prepared on the basis of these two regions, the set derived from the region located at the N-terminus being synthesized in accordance with mRNA, whilst the set derived from the tryptic peptide was synthesized in reverse, so as to be complementary to the mRNA. In order to facilitate the subsequent cloning of a segment amplified with PCR, the set of oligonucleotides derived from the tryptic peptide was given a BamHI restriction site. Then λ DNA was isolated from the TNF-α induced fibrosarcoma cDNA library and from this a TNF-BP sequence was amplified using PCR. The resulting fragment was cloned and sequenced; it comprises 158 nucleotides and contains the sequence coding for the tryptic peptide 20 between the two fragments of sequence originating from the primer oligonucleotides.

This DNA fragment was subsequently radioactively labeled and used as a probe for isolating cDNA clones from the fibrosarcoma library. The procedure involved first hybridizing plaques with the probe, separating phages from hybridizing plaques and obtaining λ DNA therefrom. Individual cDNA clones were subcloned and sequenced; two of the characterized clones contained the sequence coding for TNF-BP.

This sequence constitutes part of the sequence coding for a TNF receptor.

After shortening of the 5'-non-coding region and insertion of a stop codon after the codon for the C-terminal amino acid of the natural TNF-BP, the cDNA was inserted in a suitable expression plasmid, eukaryotic cells were transformed therewith, and the expression of TNF-BP was demonstrated using ELISA.

The still outstanding 3'-region of the TNF receptor was obtained by searching through a rat brain cDNA library from the rat glia tumour cell line C6 using a TNF-BP probe and isolating all the cDNA coding for the rat TNF receptor.

The fraction of this cDNA at the 3'-end, which was assumed to correspond to the missing 3'-region behind the EcoRI cutting site of the human TNF receptor, was used as a probe to search through the HS913T cDNA library once more. A clone was obtained which contains all the DNA coding for the TNF receptor.

After shortening of the 5'-non-coding region, the cDNA was inserted in an expression plasmid and the expression of human TNF receptor was demonstrated in eukaryotic cells by means of the binding of radioactively labeled TNF.

Northern blot analysis confirmed that the isolated cDNA corresponds substantially to all the TNF-R mRNA (the slight discrepancy arises from the absence of part of the 5'-non-coding region). From this it can be concluded that the expressed protein is the complete TNF receptor.

The invention is illustrated by means of the Examples which follow.

EXAMPLE 1

Preparation of highly purified TNF-BP a) Concentration of urine 200 liters of dialyzed urine from uraemia patients, stored in flasks containing EDTA (10 g/l), Tris (6 g/l), $NaN_3$ (1 g/l), and benzamidine hydrochloride (1 g/l) and kept in a refrigerator were concentrated by ultrafiltration using a highly permeable haemocapillary filter with an asymmetric hollow fibre membrane (FH 88H, Gambro) down to 4.2 liters with a protein content of 567 g. The concentrated urine was dialyzed against 10 mM/l Tris-HCl, pH 8. During this procedure, as in the following steps (except reverse phase chromatography), 1 mM/l of benzamidine hydrochloride was added in order to counteract proteolytic digestion. Unless otherwise stated, all the subsequent purification steps were carried out at 4° C.

b) Ion Exchange Chromatography

This step was carried out by charging DEAE Sephacel columns (2.5×40 cm) with samples of concentrated and dialyzed urine containing about 75 g of protein. Elution was carried out with 800 ml of a NaCl/10 mM Tris-HCl, pH 8 gradient, the NaCl concentration being 0 to 0.4 M. The fractions from seven columns containing the TNF-BP with a total protein content of 114 g were stored at −20° C.

c) Affinity Chromatography

In order to prepare the TNF Sepharose column, rTNF-α (15 mg) in 0.1 M $NaHCO_3$, 1 M NaCl, pH 9 (coupling buffer) was coupled to 1.5 g of cyanogen bromide-activated Sepharose 4B (Pharmacia). The Sepharose was swelled in 1 mM HCl and washed with coupling buffer. After the addition of rTNF-α the suspension was left to rotate for 2 hours at ambient temperature. The excess CNBr groups were blocked by rotation for one and a half hours with 1M ethanolamine, pH 8. The TNF Sepharose was washed a few times alternately in 1M NaCl, 0.1 M sodium acetate, pH 8 and 1 M NaCl, 0.1 M boric acid, pH 4 and then stored in phosphate-buffered saline solution with 1 mM benzamidine hydrochloride. The fractions obtained from step b) were adjusted to a concentration of 0.2 M NaCl, 10 mM Tris-HCl, pH 8. The TNF-Sepharose was packed into a column and washed with 0.2 M NaCl, 10 mM Tris-HCl, pH 8 and the TNF-BP-containing fractions, corresponding to about 30 g of protein, were applied at a throughflow rate of 10 ml/h and washed exhaustively with 0.2 M NaCl, 10 mM Tris-HCl, pH 8, until no further absorption could be detected in the eluate at 280 nm. Then TNF-BP was eluted with 0.2 M glycine/HCl, pH 2.5. TNF-BP-containing fractions from 4 separations were combined and lyophilized after the addition of polyethylene glycol (MW 6000) up to a final concentration of 10 mg/ml. The lyophilized sample was dissolved in distilled water and dialyzed against distilled water (The dialyzed sample (4 ml) was stored in deep-frozen state).

This purification step further concentrated the product by about 9000 times compared with the previous product. SDS-PAGE (carried out as described in preliminary test 2) of the TNF-BP containing fractions showed the elution of three main components with molecular weights of 28,000; 30,000; and 50,000.

d) Reverse Phase Chromatography

An aliquot (1 ml) of the fractions obtained from step c) with the addition of 0.1% trifluoroacetic acid was applied to a ProRPC HR 5/10 column (Pharmacia), connected to an FPLC system (Pharmacia). The column was equilibrated with 0.1% trifluoroacetic acid and charged at ambient temperature with a linear 15 ml gradient of 10 vol % to 50 vol % aceto-nitrile containing 0.1% trifluoroacetic acid; the through flow rate was 0.3 ml/min. Fractions of 0.5 ml were collected and the absorption at 280 nm was determined, as well as the activity of the TNF-α binding protein, using the competitive binding test as described in Example 5, using 0.01 µl of sample in each case. TNF-BP eluted as a single activity peak corresponding to a sharp UV absorption peak.

This last purification step brought an increase in specific activity of about 29 fold, whilst the total increase in activity compared with the starting material (concentrated dialysis urine) was about $1.1 \times 10^6$-fold. SDS-PAGE of the reduced and non-reduced samples, carried out as described in preliminary test 2, resulted in a diffuse band, indicating the presence of a single polypeptide with a molecular weight of about 30,000. The diffused appearance of the band may be due to the presence of one or more heterogeneous glycosylations and/or a second polypeptide present in a smaller amount. The assumption that it might be a polypeptide with the N-terminus found to be a secondary sequence in preliminary test 3d), which is longer than TNF-BP at the N-terminus, was confirmed by the sequence of the cDNA, according to which there is a fraction of 11 amino acids between the signal sequence and Asn (position 12), the sequence of which coincides with the N-terminal secondary sequence and which is obviously split off from the processed protein.

EXAMPLE 2

SDS Polyacrylamide Gel Electrophoresis (SDS-PAGE)

SDS-PAGE was carried out using the method of Laemmli (Laemmli, U.K., Nature 227:680-684 (1970)) on flat gels measuring 18 cm long, 16 cm wide, and 1.5 mm thick, with 10 pockets, by means of an LKB 2001 electrophoresis unit. The protein content of the samples from the purification steps c) and d) (preliminary test 1) was determined by Bio-Rad Protein Assay or calculated from the absorption at 280 nm, an absorption of 1.0 being recognized to be equivalent to a content of 1 mg TNF-BP/ml.

The samples containing about 25 µg of protein (from preliminary test 1c) or about 5 µg (from 1d) in reduced form (β-mercaptoethanol) and non-reduced form, were applied to a 3% collecting gel and a 5 to 20% linear polyacrylamide gradient gel. Electrophoresis was carried out at 25 mA/gel without cooling. The molecular weight markers used (Pharmacia) were phosphorylase B (MW 94,000), bovine serum albumin (MW 67,000), ovalbumin (MW 43,000), carboanhydrase (MW 30,000), soya bean trypsin inhibitor (MW 20,100), and α-lactalbumin (MW 14,400). The gels were stained with Coomassie Blue in 7% acetic acid/40% ethanol and decolorized in 7% acetic acid/25% ethanol.

The results of the SDS-PAGE showed TNF-BP to be a polypeptide chain with a molecular weight of about 30,000.

EXAMPLE 3 a) Preparation of Samples

15 µg of the protein purified according to preliminary test 1d) were desalinated using reverse phase HPLC and further purified. To do this a Bakerbond WP C18 column was used (Baker; 4.6×250 mm) and 0.1% trifluoroacetic acid in water (eluant A) or in acetonitrile (eluant B) as the mobile phase. The increase in the gradient was 20 to 68% eluant B in 24 minutes. Detection was carried out in parallel at 214 nm and 280 nm. The fraction containing TNF-BP was collected, dried, and dissolved in 75 µl of 70% formic acid and used directly for the amino acid sequence analysis.

b) Amino Acid Sequence Analysis

The automatic amino acid sequence analysis was carried out with an Applied Biosystems 477 A liquid phase sequenator by on-line determination of the phenylthiohydantoin derivatives released, using an Applied Biosystems Analyser, Model 120 A PTH. It gave the following N-terminal sequence as the main sequence (about 80% of the quantity of protein): Asp-Ser-Val-Xaa-Pro-Gln-Gly-Lys-Tyr-Ile-His-Pro-Gln (SEQ ID NO: 28). In addition, the following secondary sequence was detected: Leu-(Val)-(Pro)-(His)-Leu-Gly-Xaa-Arg-Glu (SEQ ID NO: 29). The amino acids shown in brackets could not be clearly identified.

EXAMPLE 4

SDS-Page

The sample was prepared as described in Example 3 with the difference that the quantity of sample was 10 µg. The sample was taken up in 50 µl of water and divided into 4 portions. One of the four aliquot parts was reduced in order to determine its purity by SDS-PAGE according to the method of Laemmli (Laemmli, U.K., Nature 227:680-684 (1970)) with DTT (dithiothreitol) and separated on minigels (Höfer, 55×80×0.75 mm, 15%); the molecular weight marker used was the one specified in Example 2. Staining was carried out using the Oakley method (Oakley, B. R., et al., Analyt. Biochem. 105:361-363 (1986)). The electropherogram showed a single band having a molecular weight of about 30,000.

EXAMPLE 5 a) Tryptic Peptide Mapping

About 60 µg of the protein purified in Example 1d) was desalinated by reverse phase HPLC and further purified thereby. A Bakerbond WP C18 column (Baker; 4.6×250 mm) was used, and 0.1% trifluoroacetic acid in water (eluant A) or in acetonitrile (eluant B) was used as the mobile phase. The increase in gradient amounted to 20 to 68% eluant B in 24 minutes. Detection was carried out in parallel at 214 nm and at 280 nm. The fraction containing TNF-BP (retention time about 13.0 min.) was collected, dried, and dissolved in 60 µl of 1% ammonium bicarbonate.

1% w/w, corresponding to 0.6 µg of trypsin (Boehringer Mannheim) was added to this solution and the reaction mixture was incubated for 6 hours at 37° C. Then a further 1% w/w of trypsin was added and incubation was continued overnight.

In order to reduce the disulfide bridges, the reaction mixture was then combined with 60 µl of 6 M urea and with 12 µl of 0.5 M dithiothreitol and left to stand for 2 hours at ambient temperature.

The tryptic cleavage peptides produced were separated by reverse phase HPLC, using a Delta Pak C18 column (Waters, 3.9×150 mm, 5 μm particle diameter, 100 A pore diameter) at 30° C. and 0.1% trifluoroacetic acid in water (eluant A) or in acetonitrile (eluant B) as the mobile phase. The gradient was increased from 0 to 55% W of eluant B in 55 minutes, then 55% B was maintained for 15 minutes. The flow rate was 1 ml/min. and detection was carried out in parallel at 214 nm (0.5 AUFS) and at 280 nm (0.05 AUFS).

b) Sequence Analysis of Tryptic Peptides

Some of the tryptic cleavage peptides of TNF-BP obtained in a) were subjected to automatic amino acid sequence analysis. The corresponding fractions from reverse phase HPLC were collected, dried, and dissolved in 75 μl of 70% formic acid. These solutions were used directly for sequencing in an Applied Biosystems 477 A Pulsed Liquid Phase Sequenator. Table 2 contains the results of the sequence analysis of the tryptic peptides (the amino acids shown in brackets could not be identified with certainty). The letters "Xaa" indicate that at this point the amino acid could not be identified. In fraction 8 the amino acid in position 6 could not be identified. The sequence Xaa-Asn-Ser for position 6-8 leads one to suppose that the amino acid 6 is present in glycosylated form.

In fraction 17 the amino acid in position 6 could not be identified either. The sequence Xaa-Asn-Ser (already occurring in fraction 8) for positions 6-8 leads one to suppose that amino acid 6 is present in glycosylated form. The first 13 amino acids of fraction 17 are substantially identical to fraction 8; fraction 17 should thus be a peptide formed by incomplete tryptic cleavage.

It is striking that fraction 21 is identical to positions 7 to 14 of fraction 27. Both in fraction 21 and in fraction 27 the sequence suddenly breaks off after the amino acid asparagine (position 8 or 14), even though no tryptic cleavage can be expected here. This indicates that the amino acid asparagine (position 8 in fraction 21 or position 14 in fraction 27) could be the C-terminal amino acid of TNF-BP.

It is noticeable that the sequence of fraction 12 which occurs only in small amounts, is substantially identical to the secondary sequence of the N-terminus found in preliminary test 10. The fact that the proteins of the main and subsidiary sequence could not be separated on an analytical reverse phase HPLC column (Example 3b) indicated that the protein with the subsidiary sequence was a form of TNF-BP extended at the N-terminus, which was largely converted by processing into the protein with the main sequence.

TABLE 2

Amino acid sequences of the analyzed tryptic peptides of TNF-BP

| Fraction | Amino Acid Sequence | SEQ ID NO: |
|---|---|---|
| 1 | Asp-Ser-Val-Cys-Pro-Gln-Gly-Lys | 31 |
| 2 | Xaa-Xaa-Leu-Ser-(Cys)-Ser-Lys | 32 |
| 3 | Asp-Thr-Val-(Cys)-Gly-(Cys)-Arg | 33 |
| 4 | Glu-Asn-Glu-(Cys)-Val-Ser-(Cys)-Ser-Asn-(Cys)-Lys | 34 |
| 5 | Glu-Asn-Glu-(Cys)-Val-Ser-(Cys)-(Ser)-Asn-(Cys)-Lys-(Lys) | 35 |
| 8 | Tyr-Ile-His-Pro-Gln-Xaa-Asn-Ser-Ile-Xaa-Xaa-Xaa-Lys | 36 |
| 11 | Glu-Cys-Glu-Ser-Gly-Ser-Phe-Thr-Ala-Ser-Glu-Asn-(Asn)-(Lys) | 37 |
| 12 | Leu-Val-Pro-His-Leu-Gly-Asp-Arg | 38 |
| 13 | Lys-Glu-Met-Gly-Gln-Val-Glu-Ile-Ser-Ser-(Cys)-Thr-Val-Asp-(Arg) | 39 |

TABLE 2-continued

Amino acid sequences of the analyzed tryptic peptides of TNF-BP

| Fraction | Amino Acid Sequence | SEQ ID NO: |
|---|---|---|
| 14/I | Gly-Thr-Tyr-Leu-Tyr-Asn-Asp-Cys-Pro-Gly-Pro-Gly-Gln | 40 |
| 14/II | (Glu)-Met-Gly-Gln-Val-(Glu)-(Ile)-(Ser)-Xaa-Xaa-Xaa-(Val)-(Asp) | 41 |
| 15 | Lys-Glu-Met-Gly-Gln-Val-Glu-Ile-Ser-Ser-(Cys)-Thr-Val-Asp-Arg-Asp-Thr-Val-(Cys)-Gly | 42 |
| 17 | Tyr-Ile-His-Pro-Gln-Xaa-Asn-Ser-Ile-(Cys)-(Cys)-Thr-Lys-(Cys)-His-Lys-Gly-Xaa-Tyr | 43 |
| 20 | Gly-Thr-Tyr-Leu-Tyr-Asn-Asp-Cys-Pro-Gly-Pro-Gly-Gln-Asp-Thr-Xaa-Xaa-Arg | 44 |
| 21 | Leu-(Cys)-Leu-Pro-Gln-Ile-Glu-Asn | 45 |
| 26 | Gln-Asn-Thr-Val-(Cys)-Thr-Xaa-(His)-Ala-Gly-Phe-(Phe)-Leu-(Arg) | 46 |
| 27 | Ser-Leu-Glu-(Cys)-Thr-Lys-Leu-(Cys)-Leu-Pro-Gln-Ile-Glu-Asn | 47 |

EXAMPLE 6

Analysis of the C-terminus

This analysis was carried out on the principle of the method described in Hsieng, S. L., et al., *J. Chromatography* 447:351-364 (1988).

About 60 μg of the protein purified in Example 2d was desalinated and thus further purified by reverse phase HPLC. A Bakerbond WP C18 column (Baker; 4.6×250 mm) was used and 0.1% trifluoroacetic acid in water (eluant A) or in acetonitrile (eluant B) was used as the mobile phase. The gradient was increased from 20 to 68% eluant 8 in 24 minutes. Detection was carried out in parallel at 214 nm and at 280 nm. The fraction containing TNF-BP (retention time about 13.0 min.) was collected, dried, and dissolved in 120 μl of 10 mM sodium acetate (adjusted to pH 4 with 1 N HCl).

To this solution were added 6 μl of Brij 35 (10 mg/ml in water) and 1.5 μl of carboxypeptidase P (0.1 mg/ml in water; Boehringer Mannheim, No. 810142). This corresponds to a weight ratio of enzyme to protein of 1 to 400 (Frohman, M. A., et al., *Proc. Natl. Acad. Sci.* 85:8998-9002 (1988)).

Immediately after the addition of the enzyme a sample of 20 μl of the reaction mixture was taken and the enzymatic reaction therein was stopped by acidifying with 2 μl of concentrated trifluoroacetic acid and by freezing at −20° C.

The reaction mixture was left to stand in a refrigerator (about 8° C.) and samples of 20 μl were taken after 10, 20, 60, and 120 minutes. The remainder of the reaction mixture was left at ambient temperature for another 120 minutes. Immediately after being taken, all the samples were acidified by the addition of 2 μl of concentrated trifluoroacetic acid and frozen at −20° C., thereby interrupting the enzymatic reaction.

Parallel to the sample mixture described, containing about 60 μg of TNF-BP, a reagent double blind control was set up under identical conditions but with no protein added.

After the last sample had been taken all the samples were dried for 30 minutes in a Speed Vac Concentrator, mixed with 10 μl of a solution of 2 parts of ethanol, 2 parts of water, and 1 part of triethylamine (="Redrying solution" of the Picotag amino acid analysis system of Waters) and briefly dried again. Then the samples were each mixed with 20 μl of the derivatization reagent (7:1:1:1=ethanol:water:triethylamine:phenylisothiocyanate; Picotag system) in order to derivatize the amino acids split off from the C-terminus, then left to stand for 20 minutes at ambient temperature, and then dried for 1 hour in a Speed Vac Concentrator.

In order to analyze the derivatized amino acids, the samples were dissolved in 100 µl of "Sample Diluent" (Picotag system of Waters). Of these solutions, 50 µl was analyzed by reverse phase HPLC (column, mobile phase, and gradient according to the original specifications of the Picotag system of Waters). The chromatograms of the samples and reagent double blind controls were compared with the chromatogram of a similarly derivatized mixture (100 pmol/amino acid) of standard amino acids (Beckman).

As can be seen from the quantitative results of the Picotag amino acid analysis (Table 3), asparagine is very likely the C-terminal amino acid of TNF-BP. Apart from asparagine, glutamic acid and a smaller amount of isoleucine were also detected after 240 minutes reaction. Quantities of other amino acids significantly above the reagent double blind value could not be found even after 240 minutes reaction. This result (Ile-Glu-Asn as the C-terminus) confirms the supposition made from the N-terminal sequencing of the tryptic peptides 21 and 27, to the effect that the amino acids identified at the C-terminus in these peptides (Ile-Glu-Asn; Example 5b) constitute the C-terminus of TNF-BP.

TABLE 3

Quantitative evaluation of the Picotag amino acid analysis after reaction of carboxypeptidase P with TNF-BP

| Reaction time | Integrator units for the amino acids | | |
|---|---|---|---|
| | Isoleucine | Glutamic Acid | Asparagine |
| 0 | — | — | — |
| 10 | — | — | — |
| 20 | — | — | 83.304 |
| 60 | — | — | 168.250 |
| 120 | — | — | 319.470 |
| 240 | 85.537 | 52.350 | 416.570 |

Methods used in Examples 7 to 20:

In the Examples which follow, standard molecular biological methods were used unless expressly stated otherwise, which can be found in the relevant textbooks or which correspond to the conditions recommended by the manufacturers. To simplify the description of the Examples which follow, frequently recurring methods or designations are abbreviated:

"Cutting" or "digestion" of DNA refers to the catalytic cleaving of the DNA using restriction endonucleases (restriction enzymes) at sites specific to them (restriction sites). Restriction endonucleases are commercially available and are used under the conditions recommended by the manufacturers (buffer, bovine serum albumin (BSA) as carrier protein, dithiothreitol (DTT) as antioxidant). Restriction endonucleases are designated by a capital letter, usually followed by small letters and normally a Roman numeral. The letters depend on the microorganism from which the restriction endonuclease in question was isolated (e.g., Sma I: *Serratia marcescens*). Usually, about 1 µg of DNA is cut with one or more units of the enzyme in about 20 µl of buffer solution. Normally, an incubation period of 1 hour at 37° C. is used, but this can be varied in accordance with the manufacturer's instructions for use. After cutting, the 5'-phosphate group is sometimes removed by incubation with alkaline phosphatase from calf intestine (CIP). This serves to prevent an undesirable reaction of the specific site in a subsequent ligase reaction (e.g., circularization of a linearized plasmid without the insertion of a second DNA fragment). Unless otherwise stated, DNA fragments are normally not dephosphorylated after cutting with restriction endonucleases. Reaction conditions for incubation with alkaline phosphatase can be found, for example, in the M13 Cloning and Sequencing Handbook (Amersham, PI/129/83/12). After the incubation, protein is removed by extraction with phenol and chloroform, and the DNA is precipitated from the aqueous phase by the addition of ethanol.

"Isolation" of a specific DNA fragment means the separation of the DNA fragments obtained by restriction digestion, e.g., on a 1% agarose gel. After electrophoresis and rendering the DNA visible in UV light by staining with ethidium bromide (EtBr), the desired fragment is located by means of molecular weight markers which had been applied, and is bound by further electrophoresis on DE 81 paper (Schleicher and Schüll). The DNA is washed by rinsing with low salt buffer (200 mM NaCl, 20 mM Tris, pH 7.5, 1 mM EDTA) and then is eluted with a high salt buffer (1 M NaCl, 20 mM Tris, pH 7.5, 1 mM EDTA). The DNA is precipitated by the addition of ethanol.

"Transformation" means the introduction of DNA into an organism so that the DNA can be replicated therein, either extrachromosomally or chromosomally integrated. Transformation of *E. coli* follows the method specified in the M13 Cloning and Sequencing Handbook (Amersham, PI/129/83/12).

"Sequencing" of a DNA means the determination of the nucleotide sequence. To do this, first of all, the DNA which is to be sequenced is cut with various restriction enzymes and the fragments are introduced into suitably cut M13 mp8, mp9, mp18, or mp19 double-stranded DNA, or the DNA is fragmented by ultrasound, the ends repaired, and the size-selected fragments introduced into Sma I cut, dephosphorylated M13 mp8 DNA (Shotgun method). After transformation of *E. coli* JM 101, single-stranded DNA is isolated from recombinant M13 phages in accordance with the M13 Cloning and Sequencing Handbook (Amersham, PI/129/83/12) and sequenced by the dideoxy method (Sanger et al., *Proc. Natl. Acad. Sci.* 74:5463-5467 (1977)). As an alternative to the use of the Klenow fragment of *E. coli* DNA polymerase I, it is possible to use T7-DNA polymerase ("Sequenase"; United States Biochemical Corporation). The sequence reactions are carried out in accordance with the manual "Sequenase: Step-by-Step Protocols for DNA Sequencing With Sequenase" (Version 2.0).

Another method of sequencing consists of cloning the DNA which is to be sequenced into a vector which carries, inter alia, a replication origin of a DNA single-strand phage (M13, f1) (e.g., Bluescribe or Bluescript M13; Stratagene). After transformation of *E. coli* JM101 with the recombinant molecule, the transformants can be infected with a helper phage, e.g., M13KO7 or R408; Promega). As a result, a mixture of helper phages and packaged, single-stranded recombinant vector is obtained. The sequencing template is worked up analogously to the M13 method. Double-stranded plasmid DNA is denatured by alkali treatment and directly sequenced in accordance with the above-mentioned sequencing handbook.

The sequences were evaluated using the computer programs originally developed by Staden (Staden, R., *Nucleic Acid Res.* 10:4731-4751 (1982)) and modified by Pieler (Pieler, C., Dissertation, Universität Wien (1987)). "Ligating" refers to the process of forming phosphodiester bonds between two ends of double-strand DNA fragments. Usually, between 0.02 and 0.2 µg of DNA fragments in 10 µl are ligated with about 5 units of T4 DNA ligase ("ligase") in a suitable buffer solution (Maniatis, T., et al., *Molecular Cloning: A Laboratory Manual*, Cold Spring Harbor Laboratory, p. 474 (1982)). "Excising" of DNA from transformants refers to the isolation of the plasmid DNA from bacteria by the alkaline SDS method, modified according to Birnboim and Doly, leaving out the lysozyme. From 1.5 to 50 ml of bacterial culture is used.

"Oligonucleotides" are short polydeoxynucleotides which are chemically synthesized. The Applied Biosystems Systems Synthesizer Model 381A is used for this. The oligonucleotides are synthesized in accordance with the Model 381A User Manual (Applied Biosystems). Sequence primers are used directly without any further purification. Other oligonucleotides are purified up to a chain length of 70 by the OPC method (OPC=Oligonucleotide purification column, Applied Biosystems, Product Bulletin, January 1988). Longer oligonucleotides are purified by polyacrylamide gel electrophoresis (6% acrylamide, 0.15% bisacrylamide, 6 M urea, and TBE buffer) and after elution from the gel, desalinated over a G-25 sepharose column.

EXAMPLE 7

Preparation of TNF-BP-specific hybridization probes

The oligonucleotides were selected, with a view to using them to amplify cDNA by PCR:
a) From the N-terminal amino acid sequence of the TNF-binding protein (main sequence, obtained from preliminary test 3 and Example 5, fraction 1)
Asp-Ser-Val-Cys-Pro-Gln-Gly-Lys-Tyr-Ile-His-Pro-Gln (SEQ ID NO: 48)

a heptapeptide region was selected which permits the lowest possible complexity of a mixed oligonucleotide for hybridizing to cDNA: these are amino acids 6 to 12. In order to reduce the complexity of the mixed oligonucleotide, four mixed oligonucleotides were prepared each having a complexity of 48. The oligonucleotides were prepared in the direction of the mRNA and are thus oriented towards the 3' end of the sequence and are identical to the non-coding strand of the TNF-BP gene:

|  | SEQ ID NO: |
|---|---|
| Gln-Gly-Lys-Tyr-Ile-His-Pro | 49 |
| TNF-BP #3/1 (EBI-1639):<br>5'-CAA GGT AAA TAT ATT CAT CC-3'<br>    G        G    C    C    C<br>                         A | 50<br>51<br>52 |
| TNF-BP #3/2 (EBI-1640):<br>5'-CAA GGC AAA TAT ATT CAT CC-3'<br>    G        G    C    C    C<br>                         A | 53<br>54<br>55 |
| TNF-BP #3/3 (EBI-1641):<br>5'-CAA GGA AAA TAT ATT CAT CC-3'<br>    G        G    C    C    C<br>                         A | 56<br>57<br>58 |
| TNF-BP #3/4 (EBI-1642):<br>5'-CAA GGG AAA TAT ATT CAT CC-3'<br>    G        G    C    C    C<br>                         A | 59<br>60<br>61 | b) From the amino acid sequence of a tryptic peptide (fraction 11 of the tryptic digestion) of the amino acid sequence
Glu-Cys-Glu-Ser-Gly-Ser-Phe-Thr-Ala-Ser-(Glu/Cys)-Asn-Asn-Lys (SEQ ID NOs: 62 and 63) (cf. Example 5)

a peptide region was selected and another set of mixed oligonucleotides was synthesized:

|  | SEQ ID NO: |
|---|---|
| Phe-Thr-Ala-Ser-Glu-Asn-Asn-Lys<br>                 Cys | 64<br>65 |
| TNF-BP #4/5 (EBI-1653):<br>3'-AAA TGA CGG AGA CTC TTG TTG TT CCTAGGG-5'<br>      G     G     T     T     T<br>                    T | 66<br>67<br>68 |
| TNF-BP #4/6 (EBI-1654):<br>3'-AAA TGA CGG TCA CTC TTG TTG TT CCTAGGG-5'<br>      G     G     T     T     T<br>                    T | 69<br>70<br>71 |
| TNF-BP #4/7 (EBI-1657):<br>3'-AAA TGA CGG AGA ACA TTG TTG TT CCTAGGG-5'<br>      G     G     T     T     T<br>                    T | 72<br>73<br>74 |
| TNF-BP #4/8 (EBI-1658):<br>3'-AAA TGA CGG TCA ACA TTG TTG TT CCTAGGG-5'<br>      G     G     T     T     T<br>                    T | 75<br>76<br>77 |

The oligonucleotides were synthesized complementarily to mRNA and are thus oriented towards the 5' end of the sequence. In order to allow efficient cloning of the amplified DNA fragment following PCR, a BamHI linker was also provided at the 5' end of the oligonucleotides. If, for example, oligonucleotides TNF-BP Nos. 4/5-8 together with TNF-BP Nos. 3/1-4 are used for PCR on the entire λ DNA of a library, any DNA fragment which results can be subsequently cut with BamHI. The partner oligonucleotides yield a straight end at the 5' terminus and consequently the fragment can be cloned into the SmaI-BamH1 sites of a suitable vector.

Each mixed oligonucleotide TNF-BP No. 4/5 to 8 is a mixture of 48 individual nucleotides and does not take into account a few codons, namely:

| Thr | ACG |
| Ala | GCG and GCT |
| Ser | TCG and TCC |
| As | AAT |

In the case of GCT, the possibility that the triplet CGG complementary to GCC (Ala) can be effective by forming a G-T bridge is taken into consideration, while in the case of TCG (Ser) and AAT (Asn), the same applies with regard to AGT and TTG, respectively.

ACG, GCG, and TCG are extremely rare codons (CG rule) and are therefore not taken into consideration.

EXAMPLE 8

Amplification of a Partial Sequence Coding for TNF-BP from a cDNA Library a) Isolation of λ-DNA of a cDNA library The cDNA library was prepared using the method described in EP-A10 293 567 for the human placental cDNA, with the difference that the starting material used was $10^9$ fibrosarcoma cells of the cell line HS 913 T, which had been grown by stimulation with human TNF-α (10 ng/ml). Instead of λ gt10, λ gt11 was used (cDNA synthesis: Amersham RPN 1256; EcoRI digested λ gt11 arms: Promega Biotech; in vitro packaging of the ligated DNA: Gigapack Plus, Stratagene).

5 ml of the phage supernatant of the amplified cDNA library of the human fibrosarcoma cell line HS913T in λ gt11 was mixed with 0.5 µg of RNase A and 0.5 µg of DNase I and incubated for 1 hour at 37° C. The mixture was centrifuged for 10 minutes at 5000×g, the supernatant was freed from protein by extraction with phenol and chloroform, and the DNA was precipitated from the aqueous phase by the addition of ethanol. The λ DNA was dissolved in TE buffer (10 mM Tris, pH 7.5, 1 mM EDTA).

b) PCR amplification of a TNF-BP sequence from a cDNA library

For the application of PCR (Saiki et al., *Science* 239:487 491 (1988)) to DNA from the HS913T cDNA library, 16 individual reactions were carried out, in each of which one of the 4 mixed oligonucleotides EBI-1639, EBI-1640, EBI-1641, and EBI-1642 was used as the first primer and one of the four mixed oligonucleotides EBI-1653, EBI-1654, EBI-1657, and EBI-1658 was used as the second primer. Each of these mixed oligonucleotides contains 48 different oligonucleotides of equal length.

Amplification by means of PCR took place in 50 µl reaction volume, containing 250 ng of λ DNA from the cDNA library, 50 mM KCl, 10 mM Tris, pH 8.3, 1.5 mM $MgCl_2$, 0.01% gelatine, 0.2 mM of each of the 4 deoxynucleoside triphosphates (dATP, dGTP, dCTP, and dTTP), 200 pmol of each of the first and second primers and 1.25 units of Taq polymerase (Perkin-Elmer Cetus). To prevent evaporation, the solution was coated with a few drops of mineral oil (0.1 ml); the PCR was carried out in a DNA Thermal Cycler (Perkin-Elmer Cetus) as follows: the samples were heated to 94° C. for 5 minutes in order to denature the DNA, and then subjected to 40 amplification cycles. One cycle consisted of 40 seconds incubation at 94° C., 2 minutes incubation at 55° C., and 3 minutes incubation at 72° C. At the end of the last cycle, the samples were incubated at 72° C. for a further 7 minutes to ensure that the last primer lengthening had been completed. After cooling to ambient temperature, the samples were freed from protein with phenol and chloroform, and the DNA was precipitated with ethanol.

5 µl of each of the 16 PCR samples were applied to an agarose gel and the length of the amplified DNA fragments was determined after electrophoretic separation. The most intense DNA band, a fragment 0.16 kb long, could be seen in the PCR samples which had been amplified with the oligonucleotide EBI-1653 as the first primer and one of the oligonucleotides EBI-1639, EBI-1640, EBI-1641, or EBI-1642 as the second primer. Since the sample amplified with the pair of primers EBI-1653 and EBI-1642 contained the largest amount of this 0.16 kb DNA fragment, this sample was selected for further processing.

EXAMPLE 9

Cloning and Sequencing of a DNA Fragment Obtained by PCR Amplification

The PCR product of primers EBI-1642 and EBI-1653 obtained was cut with BamHI and subsequently separated by electrophoresis in an agarose gel (1.5% NuSieve GTG agarose plus 1% Seakem GTG agarose; FMC Corporation) according to size. The main band, a DNA fragment 0.16 kb long, was electroeluted from the gel and precipitated with ethanol. This DNA fragment was ligated with BamHI/SmaI cut plasmid pUC18 (Pharmacia) and *E. coli* JMI01 was transformed with the ligation mixture. The plasmids prepared by the mini-preparation method were characterized by cutting with the restriction enzymes PvuII and EcoRI-BamHI and subsequent electrophoresis in agarose gels. The plasmid pUC18 contains two cutting sites for PvuII which flank the polycloning site in a 0.32 kb DNA fragment. Very short DNA inserts in the polycloning site of the plasmid can be made visible more easily in agarose gel after cutting with PvuII since the length is extended by 0.32 kb. By cutting with EcoRI and BamHI, the DNA fragment ligated into the plasmid vector cut with BamHI and SmaI, including some base pairs of the polylinker sequence, can be obtained. A clone with the desired insert has been designated pTNF-BP3B. The entire DNA insert of this clone was sequenced after subcloning of an EcoRI-BamHI fragment in M13 mp18 (Pharmacia) by the modified dideoxy method using sequenase (United States Biochemical Corporation).

Analysis of the PCR-amplified DNA gave the following sequence (only the non-coding strand is shown, and above it the derived amino acid sequence):

```
                  5                   10
Gln Gly Lys Tyr Ile His Pro Gln Asn Asn Ser Ile Cys
CAG GGG AAA TAT ATT CAC CCT CAA AAT AAT TCG ATT TGC 15                  20                  25
Cys Thr Lys Cys His Lys Gly Thr Tyr Leu Tyr Asn Asp
TGT ACC AAG TGC CAC AAA GGA ACC TAC TTG TAC AAT GAC 30                  35
Cys Pro Gly Pro Gly Gln Asp Thr Asp Cys Arg Glu Cys
TGT CCA GGC CCG GGG CAG GAT ACG GAC TGC AGG GAG TGT 40                  45                  50
Glu Ser Gly Ser Phe Thr Ala Ser Glu Asn Asn Lys
GAG AGC GGC TCC TTC ACA GCC TCA GAA AAC AAC AAG

GAT CC  (SEQ ID NOs: 78 and 79)
```

The first 20 and last 29 nucleotides (underlined script) correspond to the sequences of the primer oliqonucleotides EBI-1642 and the complement of EBI-1653, respectively. Amino acids 38 to 43 confirm the remaining sequence of the tryptic peptide 11. Furthermore, the DNA fragment produced by PCR contains the sequence of the peptide of fraction 20 of the tryptic digestion (amino acids 20 to 34, underlined). This shows that the clone pTNF-BP3B was derived from a cDNA which codes for TNF binding protein. pTNF-BP3B therefore constitutes a probe, e.g., for searching for TNF-BP cDNAs in cDNA libraries.

EXAMPLE 10 a. Isolation of TNF-BP cDNA Clones

About 720,000 phages of the HS913T cDNA library in λ gt11 were plated on *E. coli* Y1088 (ΔlacU169, pro::Tn5, tonA2, hsdR, supE, supF, metB, trpR, F-, λ-, (pMC9)) (about 60,000 phages per 14.5 cm petri dish, LB-agar: 10 g/l tryptone, 5 g/l of yeast extract, 5 g/l of NaCl, 1.5% agar, plating in top agarose: 10 g/l of tryptone, 8 g/l of NaCl, 0.8% agarose). Two nitrocellulose filter extracts were prepared from each plate. The filters were prewashed (16 hours at 65° C.) in:
50 mM Tris-HCl, pH 8.0
1 M NaCl
1 mM EDTA
0.1% SDS The filters were pre-hybridized for two hours at 65° C. in:
6×SSC (0.9M NaCl, 0.09 M trisodium citrate)
5× Denhardt's (0.1% Ficoll, 0.1% polyvinylpyrrolidone, 0.1% BSA=bovine serum albumin)
0.1% SDS Preparation of the radioactively labeled probe: pTNF-BP 3B was doubly cut with BamHI and EcoRI and the approximately 0.16 kb insert was isolated. 0.6 μg of the insert in 32 μl was denatured at 100° C. and primed with 60 pmol each of EBI-1642 and EBI-1653 by cooling to 80° C. over 10 minutes and rapid cooling in ice water. After the addition of:
10 μl α-$^{32}$P-dCTP (100 μCi, 3.7 MBq)
5 μl 10× priming buffer (0.1 M Tris-HCl, pH 8.0, 50 mM MgCl$_2$)
2 μl 1 mM dATP, dGTP, and dTTP
1 μl PolIK (Klenow fragment of *E. coli* DNA polymerase I, 5 units)

Incubation was carried out for 90 minutes at ambient temperature. After heat inactivation (10 minutes at 70° C.), the non-incorporated radioactivity was removed by chromatography on Biogel P6DG (Biorad) in TE buffer (10 mM Tris-HCl, pH 8, 1 mM EDTA). 65×10$^6$ cpm were incorporated. The hybridization of the filters was carried out in a total volume of 80 ml of 6×SSC/5× Denhardt's/0.1% SDS plus heat-denatured hybridizing probe for 16 hours at 65° C. The filters were washed twice for 30 minutes at ambient temperature in 6×SSC/0.01% SDS and once for 45 minutes at ambient temperature in 2×SSC/0.01% SDS and three times for 30 minutes at 65° C. in 2×SSC/0.01% SDS. The filters were air dried and then exposed to Amersham Hyperfilm for 16 hours using an intensifier screen at −70° C. In all, 30 hybridizing plaques were identified (λ-TNF-BP Nos. 1-30). The regions with the hybridizing plaques were pricked out as precisely as possible and the phages were eluted in 300 μl of SM buffer plus 30 μl of chloroform. By plaque purification (plating of about 200 phages per 9 cm petri dish on the second passage, or about 20 phages per 9 cm petri dish on the third passage, filter extracts doubled, preparation, hybridization, and washing as described in the first search) 25 hybridizing phages were finally separated (λ-TNF-BP #1-10, 12-24, 29, and 30).

b. Preparation of the Recombinant λ DNA from the Clones 1-TNF-BP Nos. 13, 15, 23, and 30

2×10$^6$ phages were plated on *E. coli* Y1088 in top agarose (10 g/l tryptone, 8 g/l NaCl 0.8% agarose) (14.5 cm petri dish) with LB agarose (1.5% agarose, 0.2% glucose, 10 mM MGSO$_4$, 10 g/l tryptone, 5 g/l yeast extract, 5 g/l NaCl) and incubated at 37° C. for 6 hours. After the plates had been cooled (30 minutes at 4° C.) they were coated with 10 ml of λ diluent (10 mM Tris-HCl, pH 8.0, 10 mM MgCl$_2$, 0.1 mM EDTA) and eluted for 16 hours at 4° C. The supernatant was transferred into 15 ml Corex test tubes and centrifuged for 10 minutes at 15,000 rpm and at 4° C. (Beckman J2-21 centrifuge, JA20 rotor). The supernatant was decanted into 10 ml polycarbonate test tubes and centrifuged at 50,000 rpm at 20° C. until ω$^2$t=3×10$^{10}$ (Beckman L8-70, 50 Ti rotor). The pellet was resuspended in 0.5 ml of λ diluent and transferred into Eppendorf test tubes (1.4 ml). After the addition of 5 μg of RNase A and 0.5 μg DNaseI and incubation at 37° C. for 30 minutes and the addition of 25 μl of 0.5 M EDTA, 12.5 μl of 1 M Tris-HCl, pH 8.0, and 6.5 μl of 20% SDS, incubation was continued at 70° C. for 30 minutes. The λ DNA was purified by phenol/chloroform extraction and precipitated with ethanol. Finally, the DNA was dissolved in 100 μl of TE buffer.

EXAMPLE 11

Subcloning and Sequencing of TNF-BP cDNA Clones 15 and 23

In order to characterize the cDNAs of the clones λ-TNF-BP15 and λ-TNF-BP23, which showed the strongest signals during hybridization, the cDNA inserts were cut out of the λ DNA with EcoRI, then after electrophoretic separation were eluted from an agarose gel and precipitated with ethanol. The DNA fragments of 1.3 kb (from λ-TNF-BP15) and 1.1 kb (from λ-TNF-BP23) were cut with EcoRI, ligated with T4 DNA ligase to the plasmid vector pT7/T3α-18 (Bethesda Research Laboratories), which was dephosphorylated with calf intestine alkaline phosphatase, and *E. coli* JM101 was transformed. From individual colonies of bacteria which showed no blue staining after selection on agarose plates with ampicillin and X-gal, plasmid DNA was prepared in a mini preparation process and the presence and orientation of the cDNA insert was determined by cutting with EcoRI and HindIII. Plasmids which contained the EcoRI insert of the phages λ-TNF-BP15 or λ-TNF-BP23, oriented in such a way that the end corresponding to the 5'-end of the mRNA was facing the T7 promotor, were designated pTNF-BP15 and pTNF-BP23, respectively. The EcoRI inserts of λ-TNF-BP15 and λ-TNF-BP23 were also ligated to the M13 mp19 vector which had been cut with EcoRI and dephosphorylated, and *E. coli* JM101 was transformed. From a few randomly selected M13 clones, single-stranded DNA was prepared and used as the basis for sequencing by the dideoxy method. On M13 clones which contained the cDNA inserts in the opposite orientation, both DNA strands were fully sequenced using the universal sequencing primer and specifically synthesized oligonucleotide primers which bind to the cDNA insert.

The complete nucleotide sequence of 1334 bases of the cDNA insert of λ-TNF-BP15, or pTNF-BP15, is shown in FIGS. 1A-1C. Bases 1-6 and 1328-1334 correspond to the EcoRI linkers which had been added to the cDNA during the preparation of the cDNA library. The nucleotide sequence of the cDNA insert of λ-TNF-BP23 corresponds to that of 1-TNF-BP15 (bases 22-1100), flanked by EcoRI linkers.

The clone λ-TNF-BP30 was also investigated; its sequence corresponds to λ-TNF-BP15, except that the sequence has a deletion of 74 bp (nucleotide 764 to 837).

EXAMPLE 12

Construction of the Expression Plasmid pAD-CMV1 and pAD-CMV2

From parts of the expression plasmids pCDM8 (Seed and Aruffo, *Proc. Natl. Acad. Sci.* 84:8573-8577 (1987); Seed, B. Nature 329:840-842 (1987)); Invitrogen), pSV2gptDHFR20 (EP-A10 321 842) and the plasmid Bluescript SK+ (Short, J. M., et al., *Nucl. Acids Res.* 11:5521-

5540 (1988); Stratagene) a new plasmid was constructed which has a multicloning site for the directed insertion of heterologous DNA sequences and which can be replicated in E. coli by means of ampicillin resistance with a high copy number. The intergenic region of M13 makes it possible to produce single-stranded plasmid DNA by superinfection of the transformed bacteria with a helper phage (e.g., R408 or M13K07) to facilitate sequencing and mutagenesis of the plasmid DNA. The T7 promotor which precedes the multi-cloning site makes it possible to prepare RNA transcripts in vitro. In mammalian cells, the expression of heterologous genes is driven by the cytomegalovirus (CMV) promotor/enhancer (Boshart, M., et al., *Cell* 41:521-530 (1985)). The SV40 replication origin makes it possible, in suitable cell lines (e.g., SV40 transformed cells such as COS-7, adenovirus transformed cell line 293 (ATCC CRL1573)), to carry out autonomous replication of the expression plasmid at high copy numbers and thus at high rates in transient expression. For preparing permanently transformed cell lines and subsequently amplifying the expression cassette by means of methotrexate, a modified hamster minigene (promotor with coding region and the first intron) for dihydrofolate reductase (DHFR) is used as the selection marker.

a) Preparation of the Vector and Promotor Sections by PCR

The plasmid Bluescript SK+ was linearized with HindIII and 5 ng of DNA was used in a 100 μl PCR mixture (reaction buffer: 50 mM KCl, 10 mM Tris-HCl, pH 8.3, 1.5 mM $MgCl_2$, 0.01% (w/v) gelatine, 0.2 mM of the four deoxynucleotide triphosphates (dATP, dGTP, dCTP, and dTTP), 2.5 units of Taq polymerase per 100 μl. The primers used were 50 pmol of the synthetic oligonucleotides EBI-1786 (5'-GGAATTCAGCCTGAATGGCGAATGGG-3'; SEQ ID NO: 80; binds just outside the M13 ori-region at Bluescript position 475, independently of the M13 ori-orientation) and EBI-1729 (5'-CCTCGAGCGTTGCTGGCGTTTTTCC-3'; SEQ ID NO: 81; binds to Bluescript at position 1195 in front of ori; corresponds to the start of the Bluescript sequence in pCDM8; 6 bases 5' yield XhoI). After 5 minutes denaturation at 94° C., PCR was carried out over 20 cycles (40 seconds at 94° C., 45 seconds at 55° C., 5 minutes at 72° C.; Perkin-Elmer Cetus Thermal Cycler). The oligonucleotides flank the intergenic region of M13 or the replication origin (ori) with the intermediate gene for β-lactamase. At the same time, at the end of the replication origin an XhoI cutting site is produced and at the other end an EcoRI cutting site is produced. The reaction mixture was freed from protein by extraction with phenol/chloroform and the DNA was precipitated with ethanol. The DNA obtained was cut with XhoI and EcoRI, and after electrophoresis in an agarose gel, a fragment of 2.3 kb was isolated.

5 ng of plasmid pCDM8 linearized with SacII was amplified by PCR with the oliqonucleotides EBI-1733 (5'-GGTC-GACATTGATTATTGACTAG-3'; SEQ ID NO: 82; binds to CMV promotor region (position 1542) of pCDM8, corresponding to position 1 in pAD-CMV; SalI site for cloning) and EBI-1734 (5'-GGAATTCCCTAGGAATACAGCGG-3'; SEQ ID NO: 83; binds to polyoma origin of 3'SV40 polyA region in pCDM8 (position 3590)) under identical conditions to those described for Bluescript SK+. The oligonucleotides bind at the beginning of the CMV promotor/enhancer sequence and produce a SalI cutting site (EBI-1733) or bind to the end of the SV40 poly-adenylation site and produce an EcoRI cutting site (EBI-1734). The PCR product was cut with SalI and EcoRI and a DNA fragment of 1.8 kb was isolated from an agarose gel.

Figure 3A:
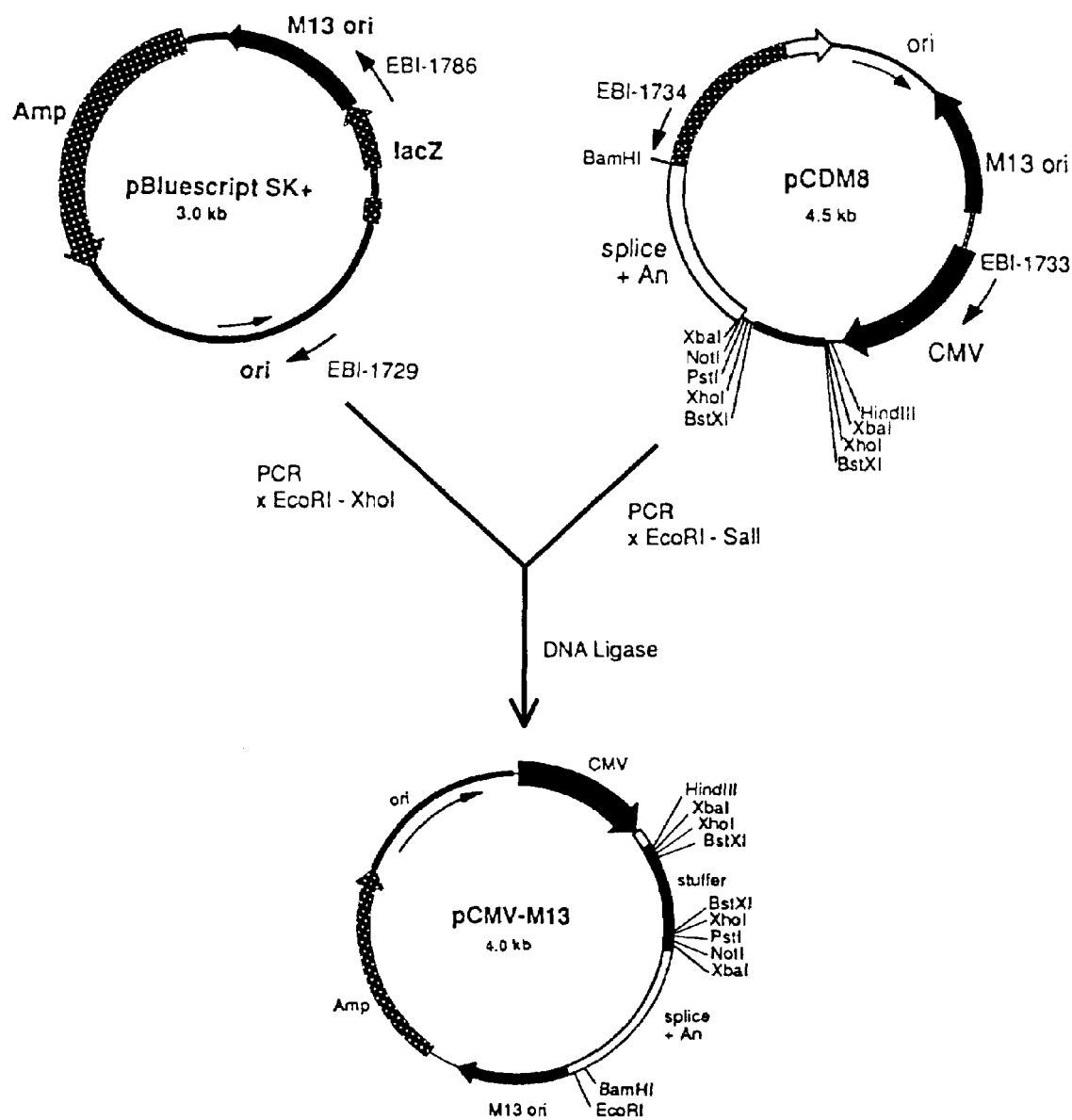
FIGS. 3A-3B depict the scheme used for the construction of plasmid pCMV-SV40.
Figure 3B:
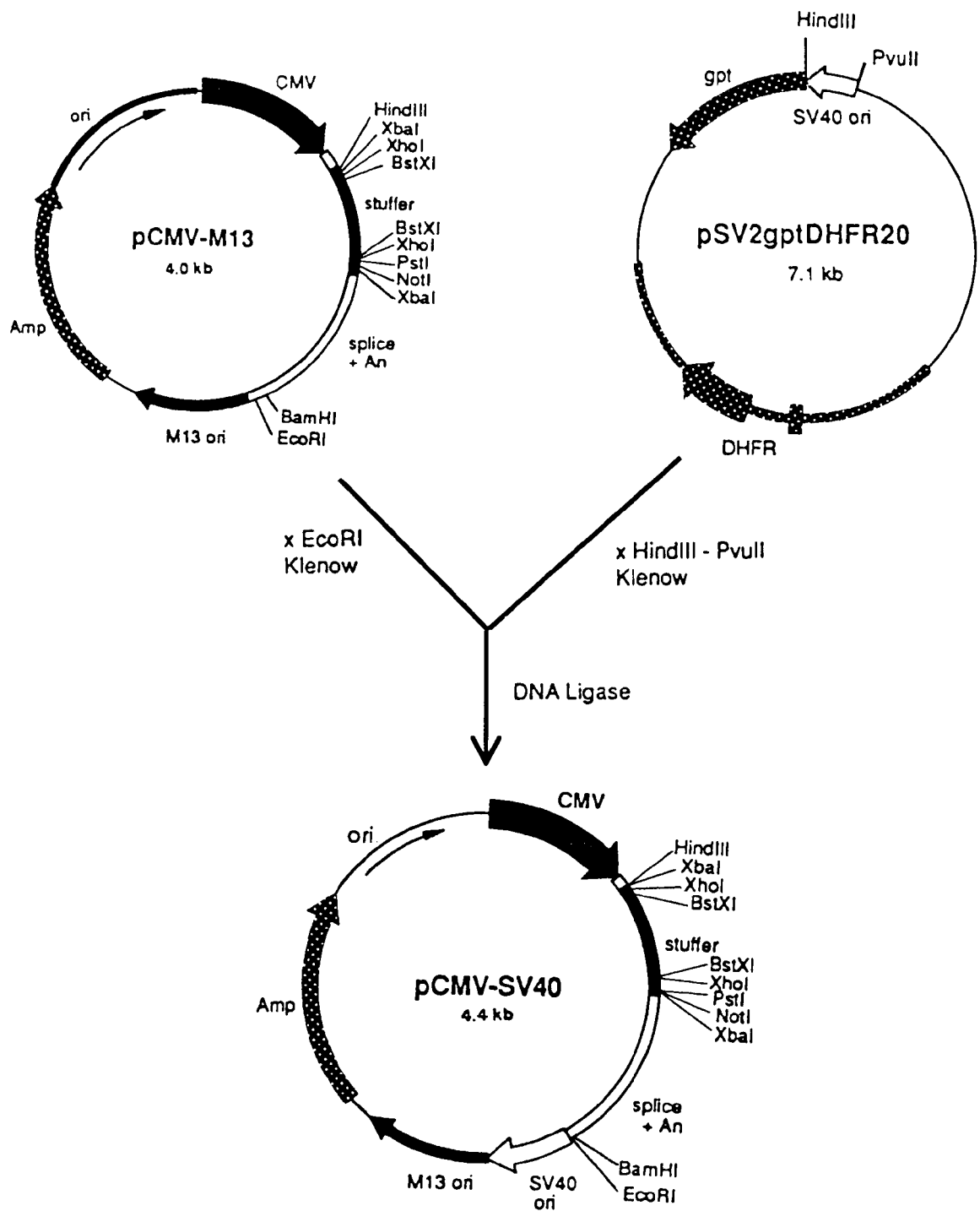

The two PCR products were ligated with T4 DNA ligase, E. coli HB101 was transformed with the resulting ligation product, and plasmid DNA was amplified and prepared using standard methods. The plasmid of the desired nature (see FIGS. 3A-3B) was designated pCMV-M13. The SV40 replication origin (SV40 ori) was isolated from the plasmid pSV2gptDHFR20 (EP-A10 321 842). To do this, this plasmid was double digested with HindIII and PvuII and the DNA ends were blunted by subsequent treatment with the large fragment of E. coli DNA polymerase (Klenow enzyme) in the presence of the four deoxynucleotide triphosphates. A 0.36 kb DNA fragment thus obtained was isolated from an agarose gel and ligated into pCMV-M13, which was linearized with EcoRI. A plasmid obtained after transformation of E. coli HB101, with the SV40 ori in the same orientation as the β-lactamase gene and the CMV promotor, was designated pCMV-SV40. The construction of this plasmid is shown in FIGS. 3A-3B.

b) Mutagenesis of the DHFR Gene

In order to prepare an expression plasmid with a versatile multicloning site, two restriction enzyme cutting sites were removed from the DHFR minigene by directed mutagenesis and three such sites were removed by deletion. To do this, a 1.7 kb BglII fragment from the plasmid pSV2gptDHFR20, containing the entire coding region of the hamster DHFR gene, was cloned into the BglII site of the plasmid pUC219 (IBI) and the plasmid pUCDHFR was obtained. E. coli JM109 (Stratagene) cells transformed with pUCDHFR were infected with an approximately 40-fold excess of the helper phage R408 (Stratagene) and shaken in LB medium for 16 hours at 37° C. Single-stranded plasmid DNA was isolated from the bacterial supernatant.

Controlled mutagenesis was carried out in two successive steps, using the in vitro mutagenesis system RPN1523 (Amersham). The EcoRI site located at the beginning of Exon 2 was destroyed by exchanging a base from GAATTC to GAGTTC. This base exchange does not result in any change in the coded amino acid sequence and furthermore corresponds to the nucleotide sequence in the natural murine DHFR gene (McGrogan, M., et al., *J. Biol. Chem.* 260:2307-2314 (1985); Mitchell, P. J., et al., *Mol. Cell. Biol.* 6:425-440 (1986)). An oligonucleotide (antisense orientation) of the sequence 5'-GTACTTGAACTCGTTCCTG-3' (SEQ ID NO: 84; EBI-1751) was used for the mutagenesis. A plasmid with the desired mutation was prepared as single strand DNA as described above and the PstI site located in the first intron was removed by mutagenesis with the oligonucleotide EBI-1857 (antisense orientation; 5'-GGCAAGGGCAG-CAGCCGG-3'; SEQ ID NO: 85) from CTGCAG into CTGCTG. The mutations were confirmed by sequencing and the resulting plasmid was designated pUCDHFR-Mut2.

The 1.7 kb BglII fragment was isolated from the plasmid pUCDHFR-Mut2 and ligated into plasmid pSV2gptDHFR20, double digested with BglII and BamHI. After transformation of E. coli, amplification, and DNA isolation, a plasmid of the desired nature was obtained, which was designated pSV2gptDHFR-Mut2. By cutting with BamHI, in the 3'-non-coding region of the DHFR gene, a 0.12 kb DNA fragment following the BglII site was removed, which also contains a KpnI cutting site. By linking the overhanging DNA ends formed with BglII and BamHI, the recognition sequences for these two enzymes were also destroyed.

The plasmid pCMV-SV40 was double digested with EcoRI and BamHI and the DNA ends were then blunted with Klenow enzyme. The DNA was purified by extraction with phenol/chloroform and ethanol precipitation, then dephosphorylated by incubation with alkaline phosphatase, and the 4.4 kb long vector DNA was isolated from an agarose gel.

Figure 4A:
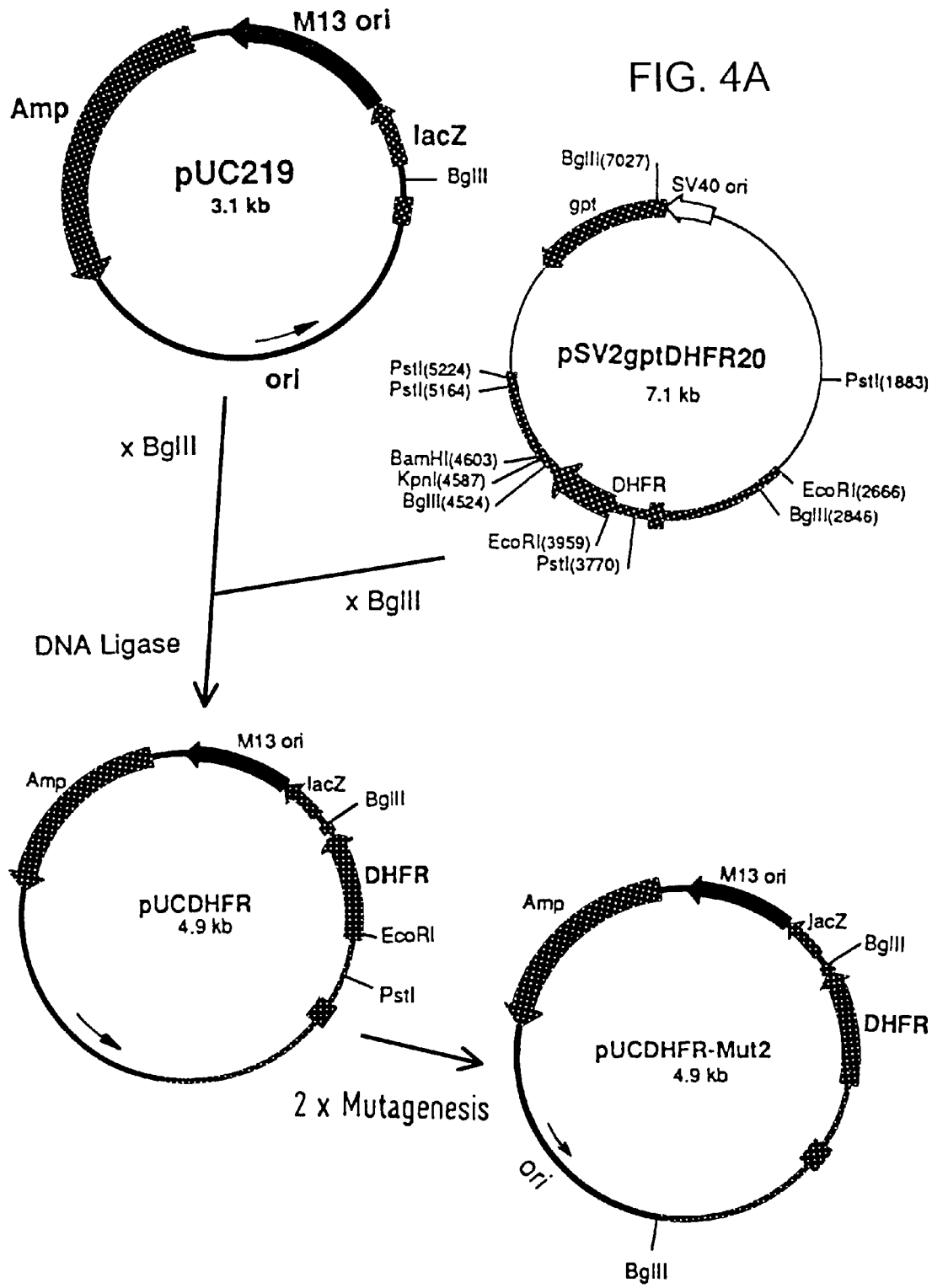
FIGS. 4A-4B depict the scheme used for the construction of plasmid pSV2gptDHFR Mut2.
Figure 4B:
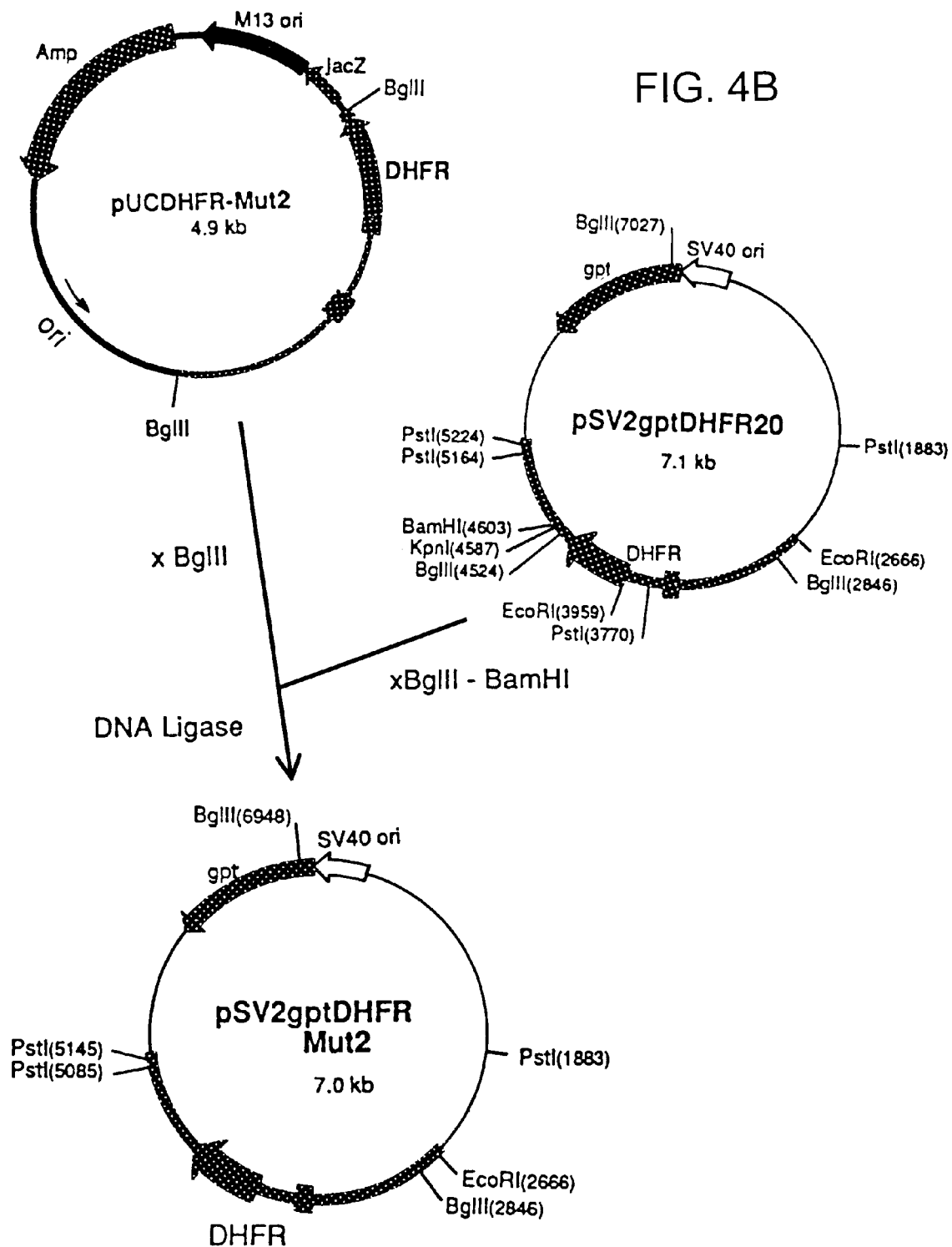

The plasmid pSV2gptDHFR-Mut2 (FIGS. 4A-4B) was double digested with EcoRI and PstI and the DNA ends were blunted by 20 minutes incubation at 11° C. with 5 units of T4 DNA polymerase (50 mM Tris-HCl, pH 8.0, 5 mM $MgCl_2$, 5 mM dithiothreitol, 0.1 mM of each of the four deoxynucleotide triphosphates, and 50 µg/ml of bovine serum albumin). The 2.4 kb long DNA fragment with the mutated DHFR gene was isolated from an agarose gel and ligated with the pCMV-SV40 prepared as described above. A plasmid obtained after transformation of *E. coli* and containing the DHFR gene in the same orientation as the CMV promotor was designated pCMV-SV40DHFR.

In the last step, the 0.4 kb stuffer fragment after the CMV promotor, which originated from the original plasmid pCDM8, was exchanged for a multicloning site. To do this, the plasmid pCMV-SV40DHFR was double digested with HindIII and XbaI and the vector part was isolated from an agarose gel. The multicloning site formed from the two oligonucleotides EBI-1823 (5'-AGCTTCTGCAGGTCGA-CATCGATGGATCCGGTACCTCGAGCGGC-CGCGAATTCT-3'; SEQ ID NO: 86) and EBI-1829 (5'-CTAGAGAATTCGCGGCCGCTCGAGGTACCGGATCC ATCGATGTCGACCTGCAGA-3'; SEQ ID NO: 87) contains (including the ends which are compatible for cloning in HindIII-XbaI) restriction cutting sites for the enzymes PstI, SalI, ClaI, BamHI, KpnI, XhoI, NotI, and EcoRI.

1 µg of each of the two oligonucleotides was incubated for 1 hour at 37° C. in 20 µl of reaction buffer (70 mM Tris-HCl, pH 7.6, 10 mM $MgCl_2$, 5 mM dithiothreitol, 0.1 mM ATP) with 5 units of T4 polynucleotide kinase in order to phosphorylate the 5' ends. The reaction was stopped by heating to 70° C. for 10 minutes and the complementary oligonucleotides were hybridized with one another by incubating the sample for a further 10 minutes at 56° C. and then slowly cooling it to ambient temperature. 4 µl of the hybridized oligonucleotides (100 ng) were ligated with about 100 ng of plasmid vector and *E. coli* HB101 was transformed. A plasmid which was capable of being linearized with the enzymes of the multicloning site (with the exception of NotI) was designed pAD CMV1. Of a number of clones tested, it was not possible to identify any one the plasmids which could be cut with NotI. Sequencing always showed the deletion of some bases within the NotI recognition sequence.

In the same way, the expression plasmid pAD-CMV2, which contains the restriction cutting sites within the multicloning site in the reverse order, was obtained with the oligonucleotide pair EBI-1820 (5'-AGCTCTAGAGAAT-TCGCGGCCGCTCGAGGTACCOGATC-CATCGATGTCGACCTGCAGAAGCTTG-3'; SEQ ID NO: 88) and EBI-1821 (5' CTAGCAAGCTTCTGCAG-GTCGACATCOATGGATCCGGTACCTC-GAGCGGCCGCGAATTCTCTAG-3'; SEQ ID NO: 89). The plasmid pAD-CMV2 was obtained which was capable of being linearized with all the restriction enzymes, including NotI.

The nucleotide sequence of the 6414 bp plasmid pAD-CMV1 (FIG. 5B) is shown in full in FIGS. 6A-6E.

The sections of the plasmid (specified in the numbering of the bases) correspond to the following sequences:

| | |
|---|---|
| 1-21 | EBI-1733, beginning of CMV enhancer-promotor (from CDM8) |
| 632-649 | T7 promotor |
| 658-713 | Multicloning site (HindIII to XbaI from EBI-1823, EBI-1829) |
| 714-1412 | SV40 intron and poly-adenylation site (from CDM8) |
| 1413-2310 | 5'-non-coding region and promotor of the hamster DHFR gene (from pSV2gptDHFR20) |
| 2311-2396 | Hamster DHFR: Exon I |
| 2516 | A to T mutation destroys PstI site in DHFR intron 1 |
| 2701-3178 | DHFR Exons 2-6 (coding region) |
| 2707 | A to G mutation destroys EcoRI site |
| 3272-3273 | Deletion between BglII and BamHI in DHFR 3' non-coding region |
| 3831 | End of DHFR gene (from pSV2gptDHFR20) |
| 3832-4169 | SV40 ori (from pSV2gptDHFR20) |
| 4170-4648 | M13 ori (from pBluescript SK+) |
| 4780-5640 | β-lactamase (coding region) |
| 6395-6414 | EBI-1729, end of the pBluescript vector sequence |

Figure 5A:
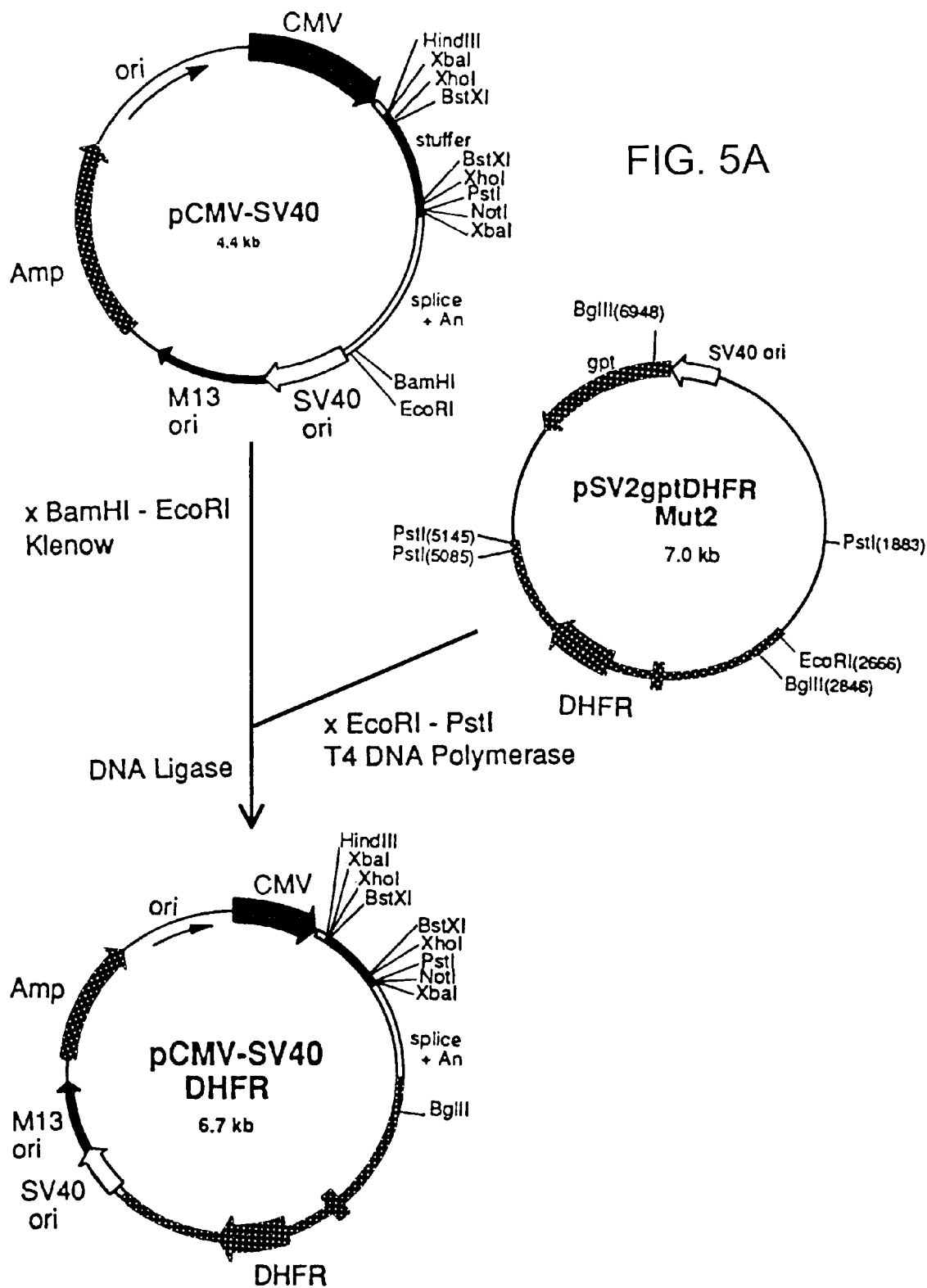
FIGS. 5A-5B depict the scheme used for the construction of plasmids pAD-CMV1 and pAD-CMV2.
Figure 5B:
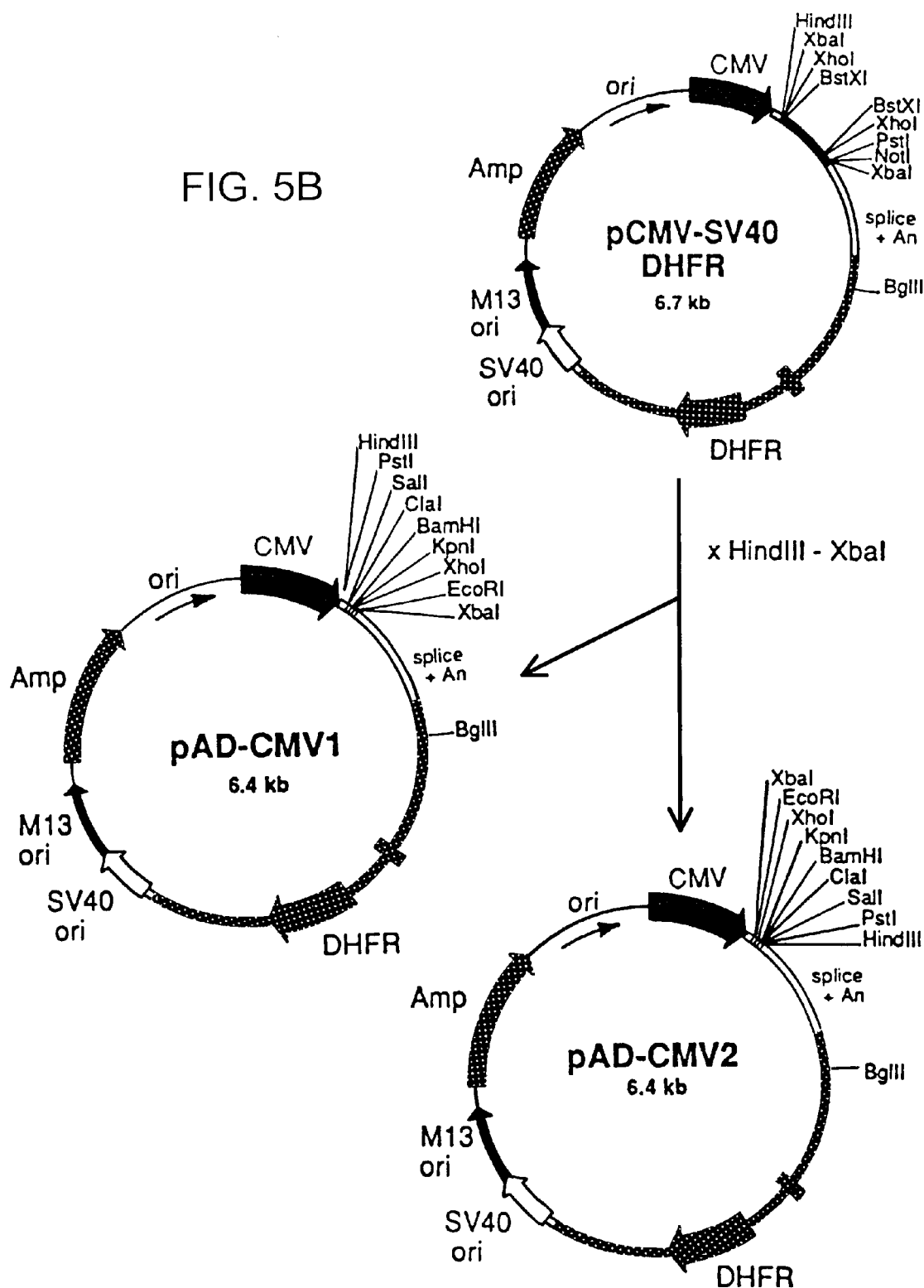

The preparation of the plasmids pAD-CMV1 and pAD-CMV2 is shown in FIGS. 5A-5B.

EXAMPLE 13

Construction of the Plasmid PADTNF-BP for the Expression of the Soluble form of TNF-BP In order to prepare the secreted form of TNF-BP by the direct method, a translation stop codon was inserted in the cDNA coding for part of the TNF receptor (see Example 11; hereinafter designated TNF-R cDNA) after the codon of the C-terminal amino acid of the natural TNF-BP (AAT, Asn-172; corresponding to position 201 in FIG. 9A). In this way the protein synthesis is broken off at this point, making it possible to secrete TNF-BP directly into the cell supernatant without having to undergo a subsequent reaction, which might possibly be rate determining of proteolytic cleaving of sections of the TNF receptor located in the C-terminal direction.

At the same time as the stop codon was inserted by PCR, the 5'-non-coding region of the TNF-R cDNA was shortened in order to remove the translation start codon of another open reading frame (bases 72-203 in FIG. 9A), which is located 5' from that of the TNF-R, and a BamHI or EcoRI cutting site is inserted at the 5' or 3'-end of the cDNA.

Figure 7A:
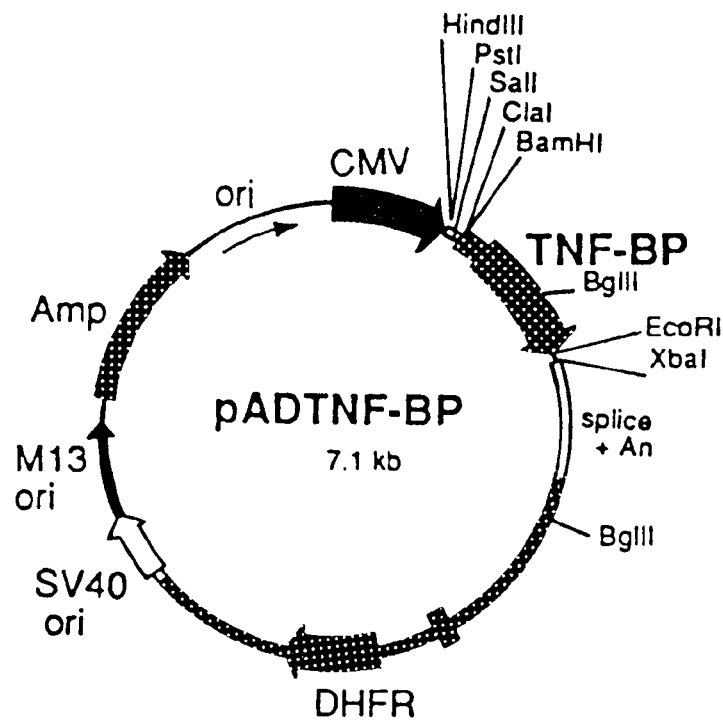
FIG. 7 depicts the structure of the plasmids designated pADTNF-BP, pADBTNF-BP, pADTNF-R, and pADBTNF-R.

100 ng of plasmid pTNF-BP15 linearized with XmnI (see Example 11) was amplified with 50 pmol of the oligonucleotides EBI-1986 (sense; 5'-CAGGATCCCAGTCTCAAC-CCTCAAC-3'; SEQ ID NO: 90) and EBI-1929 (antisense; 5'-GGGAATTCCTTATCAATTCT-CAATCTGGGGTAGGCACAACTTC-3'; SEQ ID NO: 91; insertion of two stop codons and an EcoRI site) in a 100 µl PCR mixture over 10 cycles. The cycle conditions were 40 minutes at 94° C., 45 seconds at 55° C., and 5 minutes at 72° C. After the last cycle, incubation was continued for a further 7 minutes at 72° C. and the reaction was stopped by extracting with phenol/chloroform. The DNA was precipitated with ethanol and then double digested with BamHI and EcoRI. The resulting 0.75 kb DNA fragment was isolated from an agarose gel and cloned into plasmid pT7/T3α-19 (BRL) double digested with BamHI and EcoRI. One of the plasmids obtained, which was found to have the desired sequence when the entire insert was sequenced, was designated pTNF-BP.

pTNF-BP was cut with BamHI and EcoRI and the 0.75 kb DNA insert was cloned into the expression plasmid pAD-CMV1 cut with BamHI and EcoRI. A plasmid obtained with the desired composition was designated pADTNF-BP (FIG. 7A).

EXAMPLE 14

Figure 7B:
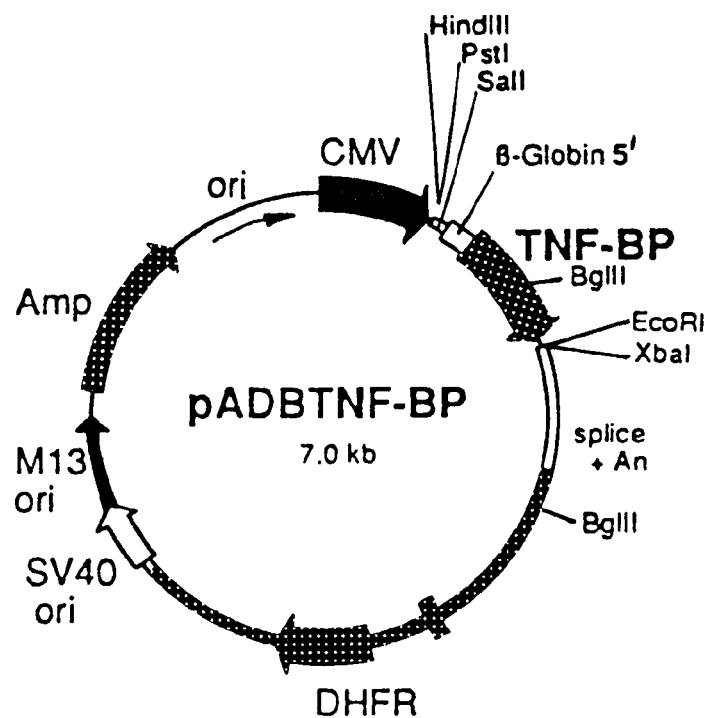

Construction of the Plasmid pADBTNF-BP for the Expression of the Soluble form of TNF-BP For another variant of an expression plasmid for the production of secreted TNF-BP, the 5'-non-coding region of TNF-R cDNA was exchanged for the 5'-non-coding region of human β-globin mRNA. The reason for this was the finding that the nucleotide sequence immediately before the translation start codon of the TNF-R sequence differs significantly from the concensus sequence found for efficient expression of eukaryotic genes (Kozak, 1987), whereas the 5'-non-coding region of the β-globin mRNA corresponds extremely well to this concensus sequence (Lawn et al., 1980). By means of the oligonucleotide EBI-2452 (5'-CACAGTCGACTTACATTTGCTTCTGACA-CAACTGTGTTCACTAGCAACCTCAAACA-GACACCATGGGCCTCTCCACCGTGC-3'; SEQ ID NO: 92), which contained after a SalI restriction cutting site the authentic 5'-non-coding sequence corresponding to the human β-globin mRNA sequence followed by 20 bases of the coding region of TNF-BP, the TNF-R sequence was modified by PCR. 100 ng of plasmid pTNF-BP linearized with EcoRI was amplified in 100 μl of reaction mixture with 50 pmol each of the oligonucleotides EBI-2452 and EBI-1922 (antisense; 5'-GAGGCTGCAATTGAAGC3'; SEQ ID NO: 93; binds to the huTNF-R sequence at position 656) for 20 cycles (40 seconds at 94° C., 45 seconds at 55° C., 90 seconds at 72° C.) After the PCR product was purified by extraction with phenol/chloroform and ethanol precipitation, the DNA was double digested with SalI and BglII and the resulting 0.51 kb DNA fragment was isolated from an agarose gel. The corresponding part of the TNF-R sequence was removed from the plasmid pTNF-BP by cutting with SalI and BglII, and the 3.1 kb long plasmid portion was isolated from an agarose gel and ligated with the 0.51 kb long PCR product. After transformation of E. coli, seven of the resulting plasmids were sequenced. One of these plasmids contained precisely the desired sequence. This plasmid was designated pBTNF-BP. The entire SalI-EcoRI insert of pBTNF-BP was cloned into the similarly cut expression plasmid pAD-CMVI and the resulting plasmid was designated pADBTNF-BP (FIG. 7B).

EXAMPLE 15

Isolation of Rat TNF-R cDNA Clones

First of all, rat brain cDNA was prepared analogously to the HS913T cDNA library (see Example 4) from the rat Glia tumour cells lines C6 (ATCC No. CCL107) in λ gt11.

600,000 phages of the rat brain cDNA library in λ gt11 were screened by hybridization as described in Example 6. The probe used was the purified EcoRI insert of pTNF-BP30 (cf. Example 6). About 100 ng of DNA was radioactively labeled with 1 μg of random hexamer primer instead of the specific oligonucleotides as described in Example 6, using [α-$^{32}$P]dCTP. 25×10$^6$ cpm were incorporated. Hybridization of the filters was carried out under the same conditions as in Example 6. The filters were washed twice for 30 minutes at ambient temperature in 2×SSC/0.1% SDS and three times for 30 minutes at 65° C. in 2×SSC/0.1 SDS and twice for 30 minutes at 65° C. in 0.5×SSC/0.5% SDS. The air dried filters were then exposed to Kodak XAR X-ray film for 16 hours using an intensifier film at −70° C. A total of 10 hybridizing plaques were identified and separated by plaque purification. After plaque purification had been carried out three times, three λ clones (λ-raTNF-R Nos. 3, 4, and 8) were finally separated out and the phage DNA was prepared as described.

The length of the cDNA insert was determined, after cutting the λ DNA with EcoRI and separation in an agarose gel, to be 2.2 kb for the clones raTNF-R3 and raTNF-R8 and 2.1 kb for the clone raTNF-R4. The EcoRI inserts of the clones λ-raTNF-R3 and λ-raTNF-R8 were cloned into similarly cut M13 mp19, and the DNA sequence was determined with universal sequencing primers and specifically synthesized oligonucleotide primers.

The complete nucleotide sequence of raTNF-R8 is shown in FIGS. 8A-8B. The first and last seven bases correspond to the EcoRI linkers which had been added during the preparation of the cDNA library.

EXAMPLE 16

Isolation of a Clone Containing the Complete cDNA Coding for the Human TNF Receptor The complete cDNA of the rat TNF-R made it easier to search for the missing 3' part of human TNF-R cDNA. The probe used for the hybridization was the 0.4 kb long PCR product of the primers EBI-2316 (5'-ATTCGTGCGGCGC-CTAG-3'; SEQ ID NO: 94; binds to TNF-R with the 2nd base of EcoRI, breaks off at the TNF-R cDNA) and EBI-2467 (5'-GTCGGTAGCACCAAGGA-3'; SEQ ID NO: 95; binds about 400 bases before poly-A to cDNA clone, corresponds to position 1775 in raTNF-R) with λ-raTNF-R8 as the starting material. This DNA fragment corresponds to the region of rat TNF-R cDNA which had been assumed to follow the internal EcoRI site in human TNF-R.

2.5×10$^6$ cpm of the raTNF-R probe were used to screen 600,000 plaques of the HS913T cDNA library. The hybridization conditions corresponded to those specified in Example 10. The filters were washed twice for 30 minutes at ambient temperature in 2×SSC/0.1% SDS and twice for 30 minutes at 65° C. in 2×SSC/0.1% SDS, air dried, and exposed to Kodak XAR X-ray film using an intensifier screen for a period of 3 days at −70° C. Six positive plaques were identified and purified to two further rounds of plaques and λ DNA was prepared (λ-TNF-R Nos. 2, 5, 6, 8, 11, and 12). After the λ DNA was cut with EcoRI, all the clones had a DNA band of about 0.8 kb long. λ-TNF-R2 and λ-TNF-R11 additionally contained an EcoRI fragment of 1.3 kb. The two EcoRI inserts from λ-TNF-R2 were subcloned into the EcoRI site of plasmid pUC218 (IBI) and then sequenced. The sequence of the 1.3 kb EcoRI fragment corresponded to that of cDNA clone pTNF-BP15, and the 0.8 kb EcoRI fragment corresponded to the 3' part of TNF-R mRNA, and contains, in front of the EcoRI linker sequence, a poly-A tail with 16 A residues. λ-TNF-R2 therefore contains the complete coding region for human TNF-R, shown in FIGS. 9A-9B.

EXAMPLE 17

Construction of the Plasmids PADTNF-R and PADBTNF-R for Expression of the Entire Human TNF Receptor First of all, as described in Example 13 for pTNF-BP or pADTNF-BP, a plasmid was constructed in which the 5'-non-coding region of pTNF-BP15 had been shortened, but, unlike the plasmids described in Example 13, the 3'-end of pTNF-BP15 was retained. For this purpose, under identical conditions to those described in Example 13, pTNF-BP15 was amplified by PCR using the oligonucleotide EBI-1986 and the M13-40 universal primer (5'-GTTTTC-CCAGTCACGAC-3'; SEQ ID NO: 96). The PCR product was double digested with BamHI and EcoRI and cloned into the plasmid pT7/T3α-19. One of the plasmids obtained was designated pTMF-BP15B.

pTNF-BP15B was cut with BamHI and EcoRI and the 1.26 kb DNA insert was cloned into expression plasmid pAD-CMV1 cut with BamHI and EcoRI. A plasmid of the desired composition thus obtained was designated pADTNF-BP15.

Figure 7C:
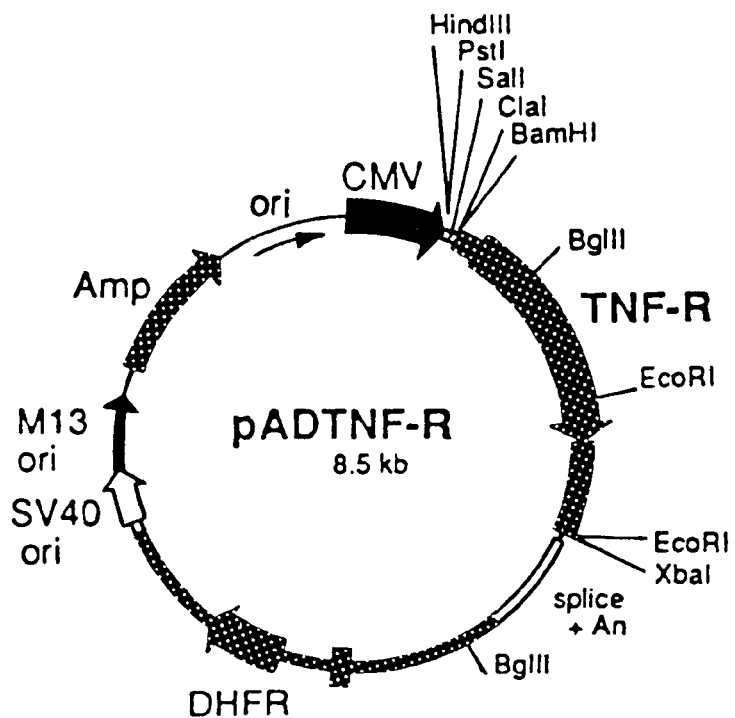

This plasmid was linearized with EcoRI and the 0.8 kb EcoRI fragment isolated from λTNF-R2 was cloned into the cutting site. After transformation of E. coli, a few randomly isolated plasmids were checked by cutting with various restriction enzymes for the correct orientation of the EcoRI fragment used. A plasmid designated pADTNF-R (FIG. 7C) was investigated further for correct orientation by sequencing the insert, starting from the 3'-end of the inserted cDNA, with the oligonucleotide EBI-2112 (5'GTCCAATTATGT-CACACC-3'; SEQ ID NO: 97), which binds to the plasmid pAD-CMV1 and its derivatives after the multicloning site.

Figure 7D:
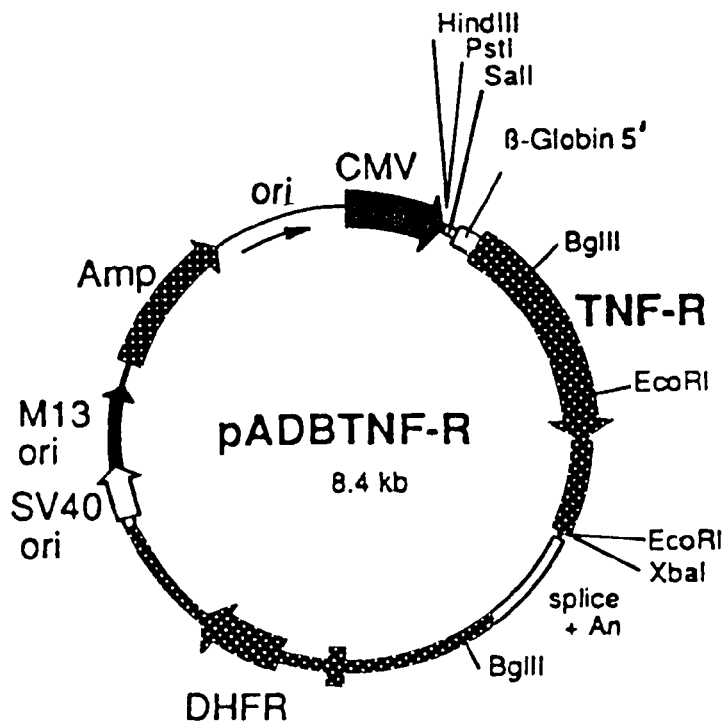

Another expression plasmid in which the 5'-non-coding region of the TNF R is exchanged for that of β-globin was constructed. Plasmid pADBTNF-BP was cut completely in order to remove the 1.1 kb BglII fragment, the DNA ends were then dephosphorylated with calf intestinal alkaline phosphatase, and the plasmid vector (5.9 kb) with the β-globin 5'-non-coding region of the β-globin gene and the 5' part of the TNF-R coding region was isolated from an agarose gel. Plasmid pADTNF-R was cut with BglII and the 2.5 kb DNA fragment containing the 3' section of the TNF-R cDNA, as far as the promotor region of the following DHFR gene, was isolated from an agarose gel, and cloned into the plasmid vector which had been prepared beforehand. A plasmid obtained after transformation of E. coli, having the BglII fragment inserted in the correct orientation, was designated pADBTNF-R (FIG. 7D).

EXAMPLE 18

Expression of Soluble TNF-BP in Eukaryotic Cell Lines a) ELISA test

In this Example TNF-BP was detected by the ELISA test as follows:

Each well of a 96 well microtitre plate was coated with 50 μl of 1:3000 diluted polyclonal rabbit serum (polyclonal rabbit antibodies; prepared by precipitation of antiserum with ammonium sulphate; final concentration 50% saturation) against natural TNF-BP for 18 hours at 4° C., washed once with 0.05% Tween 20 in PBS, and free binding sites were blocked with 150 to 200 μl of 0.5% bovine serum albumin, 0.05% Tween 20 in PBS (PBS/BSS/Tween) for one hour at ambient temperature. The wells were washed once with 0.05% Tween 20 in PBS and 50 μl of cell supernatant or known quantities of natural TNF-BP (see Tables 4 and 5) and 50 μl of a 1:10,000-fold dilution of a polyclonal mouse serum against TNF-BP was applied and incubated for two hours at ambient temperature. Then the wells were washed three times with 0.05% Tween 20 in PBS and 50 μl of rabbit anti-mouse Ig-peroxidase conjugate (Dako P161; 1:5000 in PBS/BSA/Tween) was added and incubation was continued for a further two hours at ambient temperature. The wells were washed three times with Tween/PBS and the staining reaction was carried out with orthophenylenediamine (3 mg/ml) and Naperborate (1 mg/ml) in 0.067 M potassium citrate, pH 5.0, 100 μl per well, for 20 minutes at ambient temperature away from the light. After the addition of 100 μl of 4N $H_2SO_4$, the color intensity at a wavelength of 492 nm was measured photometrically in a microfilm plate photometer.

b) Transient Expression of Soluble TNF-BP in Eukaryotic Cell Lines

About $10^6$ cells (COS-7) per 80 mm petri dish were mixed with 10% heat inactivated fetal calf serum in RPMI-1640 medium 24 hours before transfection and incubated at 37° C. in a 5% $CO_2$ atmosphere. The cells were separated from the petri dish using a rubber spatula, centrifuged for 5 minutes at 1200 rpm at ambient temperature (Heraeus minifuge, swing-out rotor 3360), washed once with 5 ml of serum-free medium, centrifuged for 5 minutes at 1200 rpm, suspended in 1 ml of medium mixed with 250 μg/ml of DEAE dextran and 10 μg of plasmid DNA (see Table 4), and purified by carrying out CsCl density gradient centrifugation twice. The cells were incubated for 40 minutes at 37° C., washed once with 5 ml of medium containing 10% calf serum, and suspended in 5 ml of medium with 100 μg/ml of chloroquin. The cells were incubated for one hour at 37° C., washed once with medium, and incubated with 10 ml of fresh medium at 37° C. After 72 hours, the cell supernatant was harvested and used to detect the secreted TNF-BP.

TABLE 4

| Cell line | COS-7 |
|---|---|
| without plasmid | <5 ng/ml |
| pADTNF-BP | 7.5 ng/ml |
| pADBTNF-BP | 146 ng/ml | c) Preparations of Cell Lines which Permanently Produce TNF-BP

The dihydrofolate reductase (DHFR)-deficient hamster ovarial cell line CHO DUKX BII (Urlaub and Chasin, 1980) was transfected with the plasmid pADBTNF-BP by calcium phosphate precipitation (Current Protocols in Molecular Biology, 1987) Four thickly grown cell culture flasks (25 $cm^2$, 5 ml of culture medium per flask) were transfected with 5 μg of DNA; after four hours incubation at $_{37}$° C. the medium was removed and replaced by 5 ml of selection medium (MEM alpha medium with 10% dialyzed fetal calf serum). After incubation overnight, the cells were detached using trypsin solution; the cells from each flask were divided between two 96-well tissue culture plates (100 μl per well in selection medium). Fresh medium was added at about weekly intervals. After about four weeks, cell clones could be observed in 79 wells. The supernatants were tested for TNF-BP activity by the ELISA test. 37 supernatants showed activity in ELISA. The results of the ELISA test of some positive clones are shown in Table 5.

TABLE 5

| Sample | Absorption at 492 nm |
|---|---|
| TNF-BP Standard | |
| 1 ng/ml | 0.390 |
| 10 ng/ml | 1.233 |

TABLE 5-continued

| Sample | Absorption at 492 nm |
|---|---|
| 100 ng/ml | 1.875 |
| Culture medium (negative control) | 0.085 |
| Clone | |
| A1G3 | 0.468 |
| A2F5 | 0.931 |
| A3A12 | 0.924 |
| A4B8 | 0.356 |
| A5A12 | 0.806 |
| A5B1O | 0.915 |
| A5C1 | 0.966 |

EXAMPLE 19

RNA Analysis (Northern Blot) of the Human TNF Receptor

1 µg of poly-A$^+$ RNA isolated from HS913T fibrosarcoma cells, placenta, and spleen was separated by electrophoresis in a 1.5% vertical agarose gel (10 mM Na phosphate buffer pH=7.0, 6.7% formaldehyde). The size marker used was a kilobase ladder radioactively labeled by a fill-in reaction with ($\alpha$-$^{32}$P)dCTP and Klenow enzyme (Bethesda Research Laboratories). The formaldehyde was removed from the gel by irrigation and the RNA was transferred in 20×SSC to a nylon membrane (Genescreen plus; NEN-DuPont). The RNA was covalently bonded on the membrane by UV irradiation (100 seconds). The membrane was prehybridized for 2 hours at 65° C. in Church buffer (Church and Gilbert, 1984) (0.5 M Na phosphate, pH 7.2, 7% SDS, 1 mM EDTA) and hybridized for 19 hours at 65° C. in fresh Church buffer with 3×10$^6$ cpm $^{32}$P-labeled DNA probe (EcoRI insert of pTNF-BP30). The filter was washed three times for 10 minutes at ambient temperature in washing buffer (40 mM Na phosphate, pH 7.2, 1% SDS) and then four times for 30 minutes at 65° C. in washing buffer, and exposed to Kodak XAR X-ray film for 18 hours using an intensifier screen at 70° C.

Figure 10:
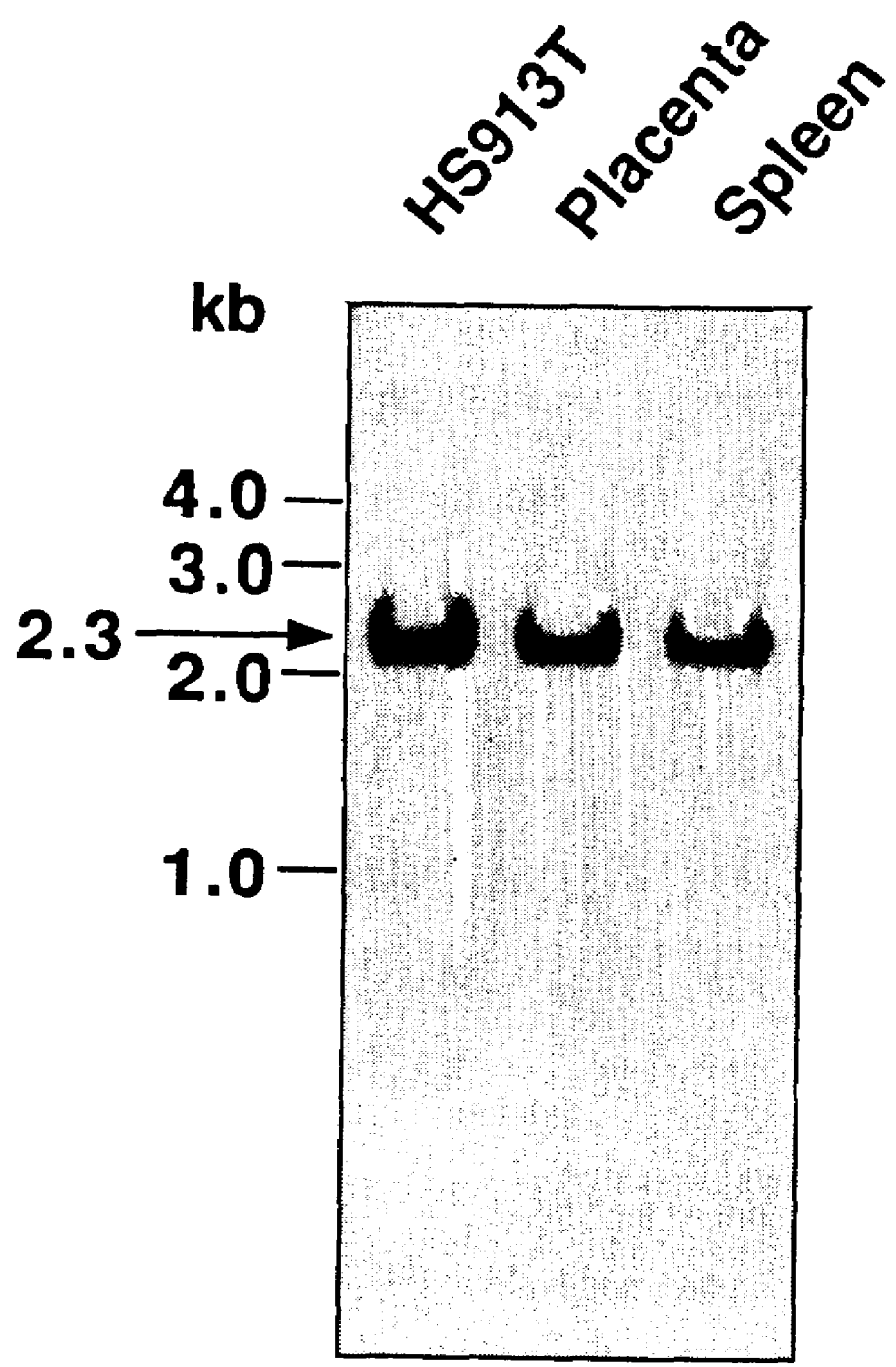
FIG. 10 depicts an autoradiogram showing a singular RNA band with a length of 2.3 kb for the human TNF receptor.

The autoradiogram (FIG. 10) shows a singular RNA band with a length of 2.3 kb for the human TNF receptor in the analyzed tissues or the cell line HS913T.

EXAMPLE 20

Expression of the TNF Receptor

For transient expression 5-10×10$^7$ COS-7 cells were incubated for 40 minutes with 10 µg of pADTNF-R plasmid DNA in a solution containing 250 1g/ml of DEAE dextran and 50 µg/ml of chloroquin. pADCMV-1-DNA was used as a control. After transfection, the cells were washed and then cultured for 48 hours. The expression of the TNF receptor was demonstrated by $^{125}$I-TNF binding. For the binding tests, the cells were washed, incubated for one hour at 4° C. with 10 mg of $^{125}$I]-TNF (specific radioactivity 38,000 cpm/ng) with or without a 200-fold excess of unlabeled TNF, and the radioactivity bound to the cells was measured in a gamma-counter. The specific binding in the control sample was 2062 cpm and in the samples transformed with TNF receptor DNA it was 6150 cpm; the values are expressed as the average bound cpm; the standard deviation determined from parallel tests was taken into account. The non-specific background in the presence of unlabeled TNF was subtracted from the values.

SEQUENCE LISTING

```
<160> NUMBER OF SEQ ID NOS: 97

<210> SEQ ID NO 1
<211> LENGTH: 1368
<212> TYPE: DNA
<213> ORGANISM: Homo sapiens
<220> FEATURE:
<221> NAME/KEY: CDS
<222> LOCATION: (1)..(1365)
<221> NAME/KEY: sig_peptide
<222> LOCATION: (1)..(87)
<221> NAME/KEY: misc_feature
<222> LOCATION: (88)..(120)
<223> OTHER INFORMATION: portion of TNF-BP pro protein cleaved by
      extracellular proteases following secretion
<221> NAME/KEY: misc_feature
<222> LOCATION: (606)..(633)
<223> OTHER INFORMATION: portion of TNF-BP pro protein cleaved by
      extracellular proteases following secretion

<400> SEQUENCE: 1 atg ggc ctc tcc acc gtg cct gac ctg ctg ctg cca ctg gtg ctc ctg        48
Met Gly Leu Ser Thr Val Pro Asp Leu Leu Leu Pro Leu Val Leu Leu
 1               5                   10                  15 gag ctg ttg gtg gga ata tac ccc tca ggg gtt att gga ctg gtc cct        96
Glu Leu Leu Val Gly Ile Tyr Pro Ser Gly Val Ile Gly Leu Val Pro
             20                  25                  30 cac cta ggg gac agg gag aag aga gat agt gtg tgt ccc caa gga aaa       144
His Leu Gly Asp Arg Glu Lys Arg Asp Ser Val Cys Pro Gln Gly Lys
         35                  40                  45
```

-continued

| | |
|---|---|
| tat atc cac cct caa aat aat tcg att tgc tgt acc aag tgc cac aaa<br>Tyr Ile His Pro Gln Asn Asn Ser Ile Cys Cys Thr Lys Cys His Lys<br>    50                          55                        60 | 192 |
| gga acc tac ttg tac aat gac tgt cca ggc ccg ggg cag gat acg gac<br>Gly Thr Tyr Leu Tyr Asn Asp Cys Pro Gly Pro Gly Gln Asp Thr Asp<br>65                       70                     75                     80 | 240 |
| tgc agg gag tgt gag agc ggc tcc ttc acc gct tca gaa aac cac ctc<br>Cys Arg Glu Cys Glu Ser Gly Ser Phe Thr Ala Ser Glu Asn His Leu<br>                    85                     90                     95 | 288 |
| aga cac tgc ctc agc tgc tcc aaa tgc cga aag gaa atg ggt cag gtg<br>Arg His Cys Leu Ser Cys Ser Lys Cys Arg Lys Glu Met Gly Gln Val<br>           100                    105                  110 | 336 |
| gag atc tct tct tgc aca gtg gac cgg gac acc gtg tgt ggc tgc agg<br>Glu Ile Ser Ser Cys Thr Val Asp Arg Asp Thr Val Cys Gly Cys Arg<br>        115                    120                  125 | 384 |
| aag aac cag tac cgg cat tat tgg agt gaa aac ctt ttc cag tgc ttc<br>Lys Asn Gln Tyr Arg His Tyr Trp Ser Glu Asn Leu Phe Gln Cys Phe<br>        130                    135                  140 | 432 |
| aat tgc agc ctc tgc ctc aat ggg acc gtg cac ctc tcc tgc cag gag<br>Asn Cys Ser Leu Cys Leu Asn Gly Thr Val His Leu Ser Cys Gln Glu<br>145                     150                  155                 160 | 480 |
| aaa cag aac acc gtg tgc acc tgc cat gca ggt ttc ttt cta aga gaa<br>Lys Gln Asn Thr Val Cys Thr Cys His Ala Gly Phe Phe Leu Arg Glu<br>                  165                  170                  175 | 528 |
| aac gag tgt gtc tcc tgt agt aac tgt aag aaa agc ctg gag tgc acg<br>Asn Glu Cys Val Ser Cys Ser Asn Cys Lys Lys Ser Leu Glu Cys Thr<br>                    180                    185                  190 | 576 |
| aag ttg tgc cta ccc cag att gag aat gtt aag ggc act gag gac tca<br>Lys Leu Cys Leu Pro Gln Ile Glu Asn Val Lys Gly Thr Glu Asp Ser<br>           195                    200                  205 | 624 |
| ggc acc aca gtg ctg ttg ccc ctg gtc att ttc ttt ggt ctt tgc ctt<br>Gly Thr Thr Val Leu Leu Pro Leu Val Ile Phe Phe Gly Leu Cys Leu<br>210                     215                  220 | 672 |
| tta tcc ctc ctc ttc att ggt tta atg tat cgc tac caa cgg tgg aag<br>Leu Ser Leu Leu Phe Ile Gly Leu Met Tyr Arg Tyr Gln Arg Trp Lys<br>225                     230                  235                 240 | 720 |
| tcc aag ctc tac tcc att gtt tgt ggg aaa tcg aca cct gaa aaa gag<br>Ser Lys Leu Tyr Ser Ile Val Cys Gly Lys Ser Thr Pro Glu Lys Glu<br>                  245                  250                  255 | 768 |
| ggg gag ctt gaa gga act act act aag ccc ctg gcc cca aac cca agc<br>Gly Glu Leu Glu Gly Thr Thr Thr Lys Pro Leu Ala Pro Asn Pro Ser<br>        260                    265                  270 | 816 |
| ttc agt ccc act cca ggc ttc acc ccc acc ctg ggc ttc agt ccc gtg<br>Phe Ser Pro Thr Pro Gly Phe Thr Pro Thr Leu Gly Phe Ser Pro Val<br>        275                    280                  285 | 864 |
| ccc agt tcc acc ttc acc tcc agc tcc acc tat acc ccc ggt gac tgt<br>Pro Ser Ser Thr Phe Thr Ser Ser Ser Thr Tyr Thr Pro Gly Asp Cys<br>        290                    295                  300 | 912 |
| ccc aac ttt gcg gct ccc cgc aga gag gtg gca cca ccc tat cag ggg<br>Pro Asn Phe Ala Ala Pro Arg Arg Glu Val Ala Pro Pro Tyr Gln Gly<br>305                     310                  315                 320 | 960 |
| gct gac ccc atc ctt gcg aca gcc ctc gcc tcc gac ccc atc ccc aac<br>Ala Asp Pro Ile Leu Ala Thr Ala Leu Ala Ser Asp Pro Ile Pro Asn<br>                  325                  330                  335 | 1008 |
| ccc ctt cag aag tgg gag gac agc gcc cac aag cca cag agc cta gac<br>Pro Leu Gln Lys Trp Glu Asp Ser Ala His Lys Pro Gln Ser Leu Asp<br>        340                    345                  350 | 1056 |
| act gat gac ccc gcg acg ctg tac gcc gtg gtg gag aac gtg ccc ccg<br>Thr Asp Asp Pro Ala Thr Leu Tyr Ala Val Val Glu Asn Val Pro Pro<br>        355                    360                  365 | 1104 |

-continued

```
ttg cgc tgg aag gaa ttc gtg cgg cgc cta ggg ctg agc gac cac gag      1152
Leu Arg Trp Lys Glu Phe Val Arg Arg Leu Gly Leu Ser Asp His Glu
370                 375                 380 atc gat cgg ctg gag ctg cag aac ggg cgc tgc ctg cgc gag gcg caa      1200
Ile Asp Arg Leu Glu Leu Gln Asn Gly Arg Cys Leu Arg Glu Ala Gln
385                 390                 395                 400 tac agc atg ctg gcg acc tgg agg cgg cgc acg ccg cgg cgc gag gcc      1248
Tyr Ser Met Leu Ala Thr Trp Arg Arg Arg Thr Pro Arg Arg Glu Ala
                405                 410                 415 acg ctg gag ctg ctg gga cgc gtg ctc cgc gac atg gac ctg ctg ggc      1296
Thr Leu Glu Leu Leu Gly Arg Val Leu Arg Asp Met Asp Leu Leu Gly
    420                 425                 430 tgc ctg gag gac atc gag gag gcg ctt tgc ggc ccc gcc gcc ctc ccg      1344
Cys Leu Glu Asp Ile Glu Glu Ala Leu Cys Gly Pro Ala Ala Leu Pro
435                 440                 445 ccc gcc ccc agt ctt ctc aga tga                                       1368
Pro Ala Pro Ser Leu Leu Arg
450                 455
```

<210> SEQ ID NO 2
<211> LENGTH: 455
<212> TYPE: PRT
<213> ORGANISM: Homo sapiens

<400> SEQUENCE: 2

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
```

```
                    245                 250                 255
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 3
<211> LENGTH: 483
<212> TYPE: DNA
<213> ORGANISM: Homo sapiens
<220> FEATURE:
<221> NAME/KEY: CDS
<222> LOCATION: (1)..(483)

<400> SEQUENCE: 3 gat agt gtg tgt ccc caa gga aaa tat atc cac cct caa aat aat tcg        48
Asp Ser Val Cys Pro Gln Gly Lys Tyr Ile His Pro Gln Asn Asn Ser
 1               5                  10                  15 att tgc tgt acc aag tgc cac aaa gga acc tac ttg tac aat gac tgt        96
Ile Cys Cys Thr Lys Cys His Lys Gly Thr Tyr Leu Tyr Asn Asp Cys
             20                  25                  30 cca ggc ccg ggg cag gat acg gac tgc agg gag tgt gag agc ggc tcc       144
Pro Gly Pro Gly Gln Asp Thr Asp Cys Arg Glu Cys Glu Ser Gly Ser
         35                  40                  45 ttc acc gct tca gaa aac cac ctc aga cac tgc ctc agc tgc tcc aaa       192
Phe Thr Ala Ser Glu Asn His Leu Arg His Cys Leu Ser Cys Ser Lys
     50                  55                  60 tgc cga aag gaa atg ggt cag gtg gag atc tct tct tgc aca gtg gac       240
Cys Arg Lys Glu Met Gly Gln Val Glu Ile Ser Ser Cys Thr Val Asp
 65                  70                  75                  80 cgg gac acc gtg tgt ggc tgc agg aag aac cag tac cgg cat tat tgg       288
Arg Asp Thr Val Cys Gly Cys Arg Lys Asn Gln Tyr Arg His Tyr Trp
                 85                  90                  95 agt gaa aac ctt ttc cag tgc ttc aat tgc agc ctc tgc ctc aat ggg       336
Ser Glu Asn Leu Phe Gln Cys Phe Asn Cys Ser Leu Cys Leu Asn Gly
            100                 105                 110
```

-continued

```
acc gtg cac ctc tcc tgc cag gag aaa cag aac acc gtg tgc acc tgc         384
Thr Val His Leu Ser Cys Gln Glu Lys Gln Asn Thr Val Cys Thr Cys
        115                 120                 125 cat gca ggt ttc ttt cta aga gaa aac gag tgt gtc tcc tgt agt aac         432
His Ala Gly Phe Phe Leu Arg Glu Asn Glu Cys Val Ser Cys Ser Asn
    130                 135                 140 tgt aag aaa agc ctg gag tgc acg aag ttg tgc cta ccc cag att gag         480
Cys Lys Lys Ser Leu Glu Cys Thr Lys Leu Cys Leu Pro Gln Ile Glu
145                 150                 155                 160 aat                                                                      483
Asn
```

<210> SEQ ID NO 4
<211> LENGTH: 161
<212> TYPE: PRT
<213> ORGANISM: Homo sapiens

<400> SEQUENCE: 4

```
Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn
```

<210> SEQ ID NO 5
<211> LENGTH: 486
<212> TYPE: DNA
<213> ORGANISM: Artificial Sequence
<220> FEATURE:
<223> OTHER INFORMATION: Description of Artificial Sequence: recombinant TNF-BP sequence
<221> NAME/KEY: CDS
<222> LOCATION: (1)..(486)

<400> SEQUENCE: 5

```
atg gat agt gtg tgt ccc caa gga aaa tat atc cac cct caa aat aat          48
Met Asp Ser Val Cys Pro Gln Gly Lys Tyr Ile His Pro Gln Asn Asn
 1               5                  10                  15 tcg att tgc tgt acc aag tgc cac aaa gga acc tac ttg tac aat gac          96
Ser Ile Cys Cys Thr Lys Cys His Lys Gly Thr Tyr Leu Tyr Asn Asp
            20                  25                  30 tgt cca ggc ccg ggg cag gat acg gac tgc agg gag tgt gag agc ggc         144
Cys Pro Gly Pro Gly Gln Asp Thr Asp Cys Arg Glu Cys Glu Ser Gly
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |

```
tcc ttc acc gct tca gaa aac cac ctc aga cac tgc ctc agc tgc tcc      192
Ser Phe Thr Ala Ser Glu Asn His Leu Arg His Cys Leu Ser Cys Ser
 50                  55                  60 aaa tgc cga aag gaa atg ggt cag gtg gag atc tct tct tgc aca gtg      240
Lys Cys Arg Lys Glu Met Gly Gln Val Glu Ile Ser Ser Cys Thr Val
 65                  70                  75                  80 gac cgg gac acc gtg tgt ggc tgc agg aag aac cag tac cgg cat tat      288
Asp Arg Asp Thr Val Cys Gly Cys Arg Lys Asn Gln Tyr Arg His Tyr
                 85                  90                  95 tgg agt gaa aac ctt ttc cag tgc ttc aat tgc agc ctc tgc ctc aat      336
Trp Ser Glu Asn Leu Phe Gln Cys Phe Asn Cys Ser Leu Cys Leu Asn
            100                 105                 110 ggg acc gtg cac ctc tcc tgc cag gag aaa cag aac acc gtg tgc acc      384
Gly Thr Val His Leu Ser Cys Gln Glu Lys Gln Asn Thr Val Cys Thr
        115                 120                 125 tgc cat gca ggt ttc ttt cta aga gaa aac gag tgt gtc tcc tgt agt      432
Cys His Ala Gly Phe Phe Leu Arg Glu Asn Glu Cys Val Ser Cys Ser
130                 135                 140 aac tgt aag aaa agc ctg gag tgc acg aag ttg tgc cta ccc cag att      480
Asn Cys Lys Lys Ser Leu Glu Cys Thr Lys Leu Cys Leu Pro Gln Ile
145                 150                 155                 160 gag aat                                                              486
Glu Asn
```

<210> SEQ ID NO 6
<211> LENGTH: 162
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 6

```
Met Asp Ser Val Cys Pro Gln Gly Lys Tyr Ile His Pro Gln Asn Asn
 1               5                  10                  15

Ser Ile Cys Cys Thr Lys Cys His Lys Gly Thr Tyr Leu Tyr Asn Asp
            20                  25                  30

Cys Pro Gly Pro Gly Gln Asp Thr Asp Cys Arg Glu Cys Glu Ser Gly
        35                  40                  45

Ser Phe Thr Ala Ser Glu Asn His Leu Arg His Cys Leu Ser Cys Ser
 50                  55                  60

Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                 85                  90                  95

Trp Ser Glu Asn Leu Phe Gln Cys Phe Asn Cys Ser Leu Cys Leu Asn
            100                 105                 110

Gly Thr Val His Leu Ser Cys Gln Glu Lys Gln Asn Thr Val Cys Thr
        115                 120                 125

Cys His Ala Gly Phe Phe Leu Arg Glu Asn Glu Cys Val Ser Cys Ser
130                 135                 140

Asn Cys Lys Lys Ser Leu Glu Cys Thr Lys Leu Cys Leu Pro Gln Ile
145                 150                 155                 160

Glu Asn
```

<210> SEQ ID NO 7
<211> LENGTH: 633

-continued

```
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(633)

<400> SEQUENCE: 7 atg ggc ctc tcc acc gtg cct gac ctg ctg ctg cca ctg gtg ctc ctg      48
Met Gly Leu Ser Thr Val Pro Asp Leu Leu Leu Pro Leu Val Leu Leu
 1               5                  10                  15 gag ctg ttg gtg gga ata tac ccc tca ggg gtt att gga ctg gtc cct      96
Glu Leu Leu Val Gly Ile Tyr Pro Ser Gly Val Ile Gly Leu Val Pro
            20                  25                  30 cac cta ggg gac agg gag aag aga gat agt gtg tgt ccc caa gga aaa     144
His Leu Gly Asp Arg Glu Lys Arg Asp Ser Val Cys Pro Gln Gly Lys
        35                  40                  45 tat atc cac cct caa aat aat tcg att tgc tgt acc aag tgc cac aaa     192
Tyr Ile His Pro Gln Asn Asn Ser Ile Cys Cys Thr Lys Cys His Lys
    50                  55                  60 gga acc tac ttg tac aat gac tgt cca ggc ccg ggg cag gat acg gac     240
Gly Thr Tyr Leu Tyr Asn Asp Cys Pro Gly Pro Gly Gln Asp Thr Asp
65                  70                  75                  80 tgc agg gag tgt gag agc ggc tcc ttc acc gct tca gaa aac cac ctc     288
Cys Arg Glu Cys Glu Ser Gly Ser Phe Thr Ala Ser Glu Asn His Leu
                85                  90                  95 aga cac tgc ctc agc tgc tcc aaa tgc cga aag gaa atg ggt cag gtg     336
Arg His Cys Leu Ser Cys Ser Lys Cys Arg Lys Glu Met Gly Gln Val
            100                 105                 110 gag atc tct tct tgc aca gtg gac cgg gac acc gtg tgt ggc tgc agg     384
Glu Ile Ser Ser Cys Thr Val Asp Arg Asp Thr Val Cys Gly Cys Arg
        115                 120                 125 aag aac cag tac cgg cat tat tgg agt gaa aac ctt ttc cag tgc ttc     432
Lys Asn Gln Tyr Arg His Tyr Trp Ser Glu Asn Leu Phe Gln Cys Phe
    130                 135                 140 aat tgc agc ctc tgc ctc aat ggg acc gtg cac ctc tcc tgc cag gag     480
Asn Cys Ser Leu Cys Leu Asn Gly Thr Val His Leu Ser Cys Gln Glu
145                 150                 155                 160 aaa cag aac acc gtg tgc acc tgc cat gca ggt ttc ttt cta aga gaa     528
Lys Gln Asn Thr Val Cys Thr Cys His Ala Gly Phe Phe Leu Arg Glu
                165                 170                 175 aac gag tgt gtc tcc tgt agt aac tgt aag aaa agc ctg gag tgc acg     576
Asn Glu Cys Val Ser Cys Ser Asn Cys Lys Lys Ser Leu Glu Cys Thr
            180                 185                 190 aag ttg tgc cta ccc cag att gag aat gtt aag ggc act gag gac tca     624
Lys Leu Cys Leu Pro Gln Ile Glu Asn Val Lys Gly Thr Glu Asp Ser
        195                 200                 205 ggc acc aca                                                          633
Gly Thr Thr
    210

<210> SEQ ID NO 8
<211> LENGTH: 211
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 8

Met Gly Leu Ser Thr Val Pro Asp Leu Leu Leu Pro Leu Val Leu Leu
 1               5                  10                  15
```

-continued

```
Glu Leu Leu Val Gly Ile Tyr Pro Ser Gly Val Ile Gly Leu Val Pro
             20                   25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr
    210
```

<210> SEQ ID NO 9
<211> LENGTH: 549
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(549)

<400> SEQUENCE: 9

```
atg ctg gtc cct cac cta ggg gac agg gag aag aga gat agt gtg tgt      48
Met Leu Val Pro His Leu Gly Asp Arg Glu Lys Arg Asp Ser Val Cys
 1               5                  10                  15 ccc caa gga aaa tat atc cac cct caa aat aat tcg att tgc tgt acc      96
Pro Gln Gly Lys Tyr Ile His Pro Gln Asn Asn Ser Ile Cys Cys Thr
             20                  25                  30 aag tgc cac aaa gga acc tac ttg tac aat gac tgt cca ggc ccg ggg     144
Lys Cys His Lys Gly Thr Tyr Leu Tyr Asn Asp Cys Pro Gly Pro Gly
         35                  40                  45 cag gat acg gac tgc agg gag tgt gag agc ggc tcc ttc acc gct tca     192
Gln Asp Thr Asp Cys Arg Glu Cys Glu Ser Gly Ser Phe Thr Ala Ser
     50                  55                  60 gaa aac cac ctc aga cac tgc ctc agc tgc tcc aaa tgc cga aag gaa     240
Glu Asn His Leu Arg His Cys Leu Ser Cys Ser Lys Cys Arg Lys Glu
 65                  70                  75                  80 atg ggt cag gtg gag atc tct tct tgc aca gtg gac cgg gac acc gtg     288
Met Gly Gln Val Glu Ile Ser Ser Cys Thr Val Asp Arg Asp Thr Val
                 85                  90                  95 tgt ggc tgc agg aag aac cag tac cgg cat tat tgg agt gaa aac ctt     336
Cys Gly Cys Arg Lys Asn Gln Tyr Arg His Tyr Trp Ser Glu Asn Leu
```

```
ttc cag tgc ttc aat tgc agc ctc tgc ctc aat ggg acc gtg cac ctc      384
Phe Gln Cys Phe Asn Cys Ser Leu Cys Leu Asn Gly Thr Val His Leu
        115                 120                 125 tcc tgc cag gag aaa cag aac acc gtg tgc acc tgc cat gca ggt ttc      432
Ser Cys Gln Glu Lys Gln Asn Thr Val Cys Thr Cys His Ala Gly Phe
130                 135                 140 ttt cta aga gaa aac gag tgt gtc tcc tgt agt aac tgt aag aaa agc      480
Phe Leu Arg Glu Asn Glu Cys Val Ser Cys Ser Asn Cys Lys Lys Ser
145                 150                 155                 160 ctg gag tgc acg aag ttg tgc cta ccc cag att gag aat gtt aag ggc      528
Leu Glu Cys Thr Lys Leu Cys Leu Pro Gln Ile Glu Asn Val Lys Gly
                165                 170                 175 act gag gac tca ggc acc aca                                          549
Thr Glu Asp Ser Gly Thr Thr
                180

<210> SEQ ID NO 10
<211> LENGTH: 183
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 10

Met Leu Val Pro His Leu Gly Asp Arg Glu Lys Arg Asp Ser Val Cys
  1               5                  10                  15

Pro Gln Gly Lys Tyr Ile His Pro Gln Asn Asn Ser Ile Cys Cys Thr
                 20                  25                  30

Lys Cys His Lys Gly Thr Tyr Leu Tyr Asn Asp Cys Pro Gly Pro Gly
             35                  40                  45

Gln Asp Thr Asp Cys Arg Glu Cys Glu Ser Gly Ser Phe Thr Ala Ser
         50                  55                  60

Glu Asn His Leu Arg His Cys Leu Ser Cys Ser Lys Cys Arg Lys Glu
 65                  70                  75                  80

Met Gly Gln Val Glu Ile Ser Ser Cys Thr Val Asp Arg Asp Thr Val
                 85                  90                  95

Cys Gly Cys Arg Lys Asn Gln Tyr Arg His Tyr Trp Ser Glu Asn Leu
            100                 105                 110

Phe Gln Cys Phe Asn Cys Ser Leu Cys Leu Asn Gly Thr Val His Leu
        115                 120                 125

Ser Cys Gln Glu Lys Gln Asn Thr Val Cys Thr Cys His Ala Gly Phe
130                 135                 140

Phe Leu Arg Glu Asn Glu Cys Val Ser Cys Ser Asn Cys Lys Lys Ser
145                 150                 155                 160

Leu Glu Cys Thr Lys Leu Cys Leu Pro Gln Ile Glu Asn Val Lys Gly
                165                 170                 175

Thr Glu Asp Ser Gly Thr Thr
                180

<210> SEQ ID NO 11
<211> LENGTH: 600
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(600)
```

-continued

```
<400> SEQUENCE: 11 atg ggc ctc tcc acc gtg cct gac ctg ctg ctg cca ctg gtg ctc ctg      48
Met Gly Leu Ser Thr Val Pro Asp Leu Leu Leu Pro Leu Val Leu Leu
1               5                   10                  15 gag ctg ttg gtg gga ata tac ccc tca ggg gtt att gga gat agt gtg      96
Glu Leu Leu Val Gly Ile Tyr Pro Ser Gly Val Ile Gly Asp Ser Val
                20                  25                  30 tgt ccc caa gga aaa tat atc cac cct caa aat aat tcg att tgc tgt     144
Cys Pro Gln Gly Lys Tyr Ile His Pro Gln Asn Asn Ser Ile Cys Cys
            35                  40                  45 acc aag tgc cac aaa gga acc tac ttg tac aat gac tgt cca ggc ccg     192
Thr Lys Cys His Lys Gly Thr Tyr Leu Tyr Asn Asp Cys Pro Gly Pro
        50                  55                  60 ggg cag gat acg gac tgc agg gag tgt gag agc ggc tcc ttc acc gct     240
Gly Gln Asp Thr Asp Cys Arg Glu Cys Glu Ser Gly Ser Phe Thr Ala
65                  70                  75                  80 tca gaa aac cac ctc aga cac tgc ctc agc tgc tcc aaa tgc cga aag     288
Ser Glu Asn His Leu Arg His Cys Leu Ser Cys Ser Lys Cys Arg Lys
                85                  90                  95 gaa atg ggt cag gtg gag atc tct tct tgc aca gtg gac cgg gac acc     336
Glu Met Gly Gln Val Glu Ile Ser Ser Cys Thr Val Asp Arg Asp Thr
            100                 105                 110 gtg tgt ggc tgc agg aag aac cag tac cgg cat tat tgg agt gaa aac     384
Val Cys Gly Cys Arg Lys Asn Gln Tyr Arg His Tyr Trp Ser Glu Asn
        115                 120                 125 ctt ttc cag tgc ttc aat tgc agc ctc tgc ctc aat ggg acc gtg cac     432
Leu Phe Gln Cys Phe Asn Cys Ser Leu Cys Leu Asn Gly Thr Val His
130                 135                 140 ctc tcc tgc cag gag aaa cag aac acc gtg tgc acc tgc cat gca ggt     480
Leu Ser Cys Gln Glu Lys Gln Asn Thr Val Cys Thr Cys His Ala Gly
145                 150                 155                 160 ttc ttt cta aga gaa aac gag tgt gtc tcc tgt agt aac tgt aag aaa     528
Phe Phe Leu Arg Glu Asn Glu Cys Val Ser Cys Ser Asn Cys Lys Lys
                165                 170                 175 agc ctg gag tgc acg aag ttg tgc cta ccc cag att gag aat gtt aag     576
Ser Leu Glu Cys Thr Lys Leu Cys Leu Pro Gln Ile Glu Asn Val Lys
            180                 185                 190 ggc act gag gac tca ggc acc aca                                     600
Gly Thr Glu Asp Ser Gly Thr Thr
        195                 200

<210> SEQ ID NO 12
<211> LENGTH: 200
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 12

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Asp Ser Val
                20                  25                  30

Cys Pro Gln Gly Lys Tyr Ile His Pro Gln Asn Asn Ser Ile Cys Cys
            35                  40                  45

Thr Lys Cys His Lys Gly Thr Tyr Leu Tyr Asn Asp Cys Pro Gly Pro
        50                  55                  60

Gly Gln Asp Thr Asp Cys Arg Glu Cys Glu Ser Gly Ser Phe Thr Ala
```

```
                65                  70                  75                  80
           Ser Glu Asn His Leu Arg His Cys Leu Ser Cys Ser Lys Cys Arg Lys
                           85                  90                  95

Glu Met Gly Gln Val Glu Ile Ser Ser Cys Thr Val Asp Arg Asp Thr
                       100                 105                 110

Val Cys Gly Cys Arg Lys Asn Gln Tyr Arg His Tyr Trp Ser Glu Asn
                       115                 120                 125

Leu Phe Gln Cys Phe Asn Cys Ser Leu Cys Leu Asn Gly Thr Val His
                   130                 135                 140

Leu Ser Cys Gln Glu Lys Gln Asn Thr Val Cys Thr Cys His Ala Gly
           145                 150                 155                 160

Phe Phe Leu Arg Glu Asn Glu Cys Val Ser Cys Ser Asn Cys Lys Lys
                           165                 170                 175

Ser Leu Glu Cys Thr Lys Leu Cys Leu Pro Gln Ile Glu Asn Val Lys
                       180                 185                 190

Gly Thr Glu Asp Ser Gly Thr Thr
                       195                 200

<210> SEQ ID NO 13
<211> LENGTH: 603
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(603)

<400> SEQUENCE: 13 atg ggc ctc tcc acc gtg cct gac ctg ctg ctg cca ctg gtg ctc ctg        48
Met Gly Leu Ser Thr Val Pro Asp Leu Leu Leu Pro Leu Val Leu Leu
  1               5                  10                  15 gag ctg ttg gtg gga ata tac ccc tca ggg gtt att gga ctg gtc cct        96
Glu Leu Leu Val Gly Ile Tyr Pro Ser Gly Val Ile Gly Leu Val Pro
                 20                  25                  30 cac cta ggg gac agg gag aag aga gat agt gtg tgt ccc caa gga aaa       144
His Leu Gly Asp Arg Glu Lys Arg Asp Ser Val Cys Pro Gln Gly Lys
             35                  40                  45 tat atc cac cct caa aat aat tcg att tgc tgt acc aag tgc cac aaa       192
Tyr Ile His Pro Gln Asn Asn Ser Ile Cys Cys Thr Lys Cys His Lys
         50                  55                  60 gga acc tac ttg tac aat gac tgt cca ggc ccg ggg cag gat acg gac       240
Gly Thr Tyr Leu Tyr Asn Asp Cys Pro Gly Pro Gly Gln Asp Thr Asp
 65                  70                  75                  80 tgc agg gag tgt gag agc ggc tcc ttc acc gct tca gaa aac cac ctc       288
Cys Arg Glu Cys Glu Ser Gly Ser Phe Thr Ala Ser Glu Asn His Leu
                 85                  90                  95 aga cac tgc ctc agc tgc tcc aaa tgc cga aag gaa atg ggt cag gtg       336
Arg His Cys Leu Ser Cys Ser Lys Cys Arg Lys Glu Met Gly Gln Val
            100                 105                 110 gag atc tct tct tgc aca gtg gac cgg gac acc gtg tgt ggc tgc agg       384
Glu Ile Ser Ser Cys Thr Val Asp Arg Asp Thr Val Cys Gly Cys Arg
        115                 120                 125 aag aac cag tac cgg cat tat tgg agt gaa aac ctt ttc cag tgc ttc       432
Lys Asn Gln Tyr Arg His Tyr Trp Ser Glu Asn Leu Phe Gln Cys Phe
    130                 135                 140 aat tgc agc ctc tgc ctc aat ggg acc gtg cac ctc tcc tgc cag gag       480
Asn Cys Ser Leu Cys Leu Asn Gly Thr Val His Leu Ser Cys Gln Glu
145                 150                 155                 160
```

```
aaa cag aac acc gtg tgc acc tgc cat gca ggt ttc ttt cta aga gaa    528
Lys Gln Asn Thr Val Cys Thr Cys His Ala Gly Phe Phe Leu Arg Glu
            165                 170                 175 aac gag tgt gtc tcc tgt agt aac tgt aag aaa agc ctg gag tgc acg    576
Asn Glu Cys Val Ser Cys Ser Asn Cys Lys Lys Ser Leu Glu Cys Thr
        180                 185                 190 aag ttg tgc cta ccc cag att gag aat                                603
Lys Leu Cys Leu Pro Gln Ile Glu Asn
    195                 200

<210> SEQ ID NO 14
<211> LENGTH: 201
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 14

Met Gly Leu Ser Thr Val Pro Asp Leu Leu Pro Leu Val Leu Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn
        195                 200

<210> SEQ ID NO 15
<211> LENGTH: 519
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(519)

<400> SEQUENCE: 15 atg ctg gtc cct cac cta ggg gac agg gag aag aga gat agt gtg tgt     48
Met Leu Val Pro His Leu Gly Asp Arg Glu Lys Arg Asp Ser Val Cys
 1               5                  10                  15
```

```
ccc caa gga aaa tat atc cac cct caa aat aat tcg att tgc tgt acc       96
Pro Gln Gly Lys Tyr Ile His Pro Gln Asn Asn Ser Ile Cys Cys Thr
             20                  25                  30 aag tgc cac aaa gga acc tac ttg tac aat gac tgt cca ggc ccg ggg      144
Lys Cys His Lys Gly Thr Tyr Leu Tyr Asn Asp Cys Pro Gly Pro Gly
         35                  40                  45 cag gat acg gac tgc agg gag tgt gag agc ggc tcc ttc acc gct tca      192
Gln Asp Thr Asp Cys Arg Glu Cys Glu Ser Gly Ser Phe Thr Ala Ser
 50                  55                  60 gaa aac cac ctc aga cac tgc ctc agc tgc tcc aaa tgc cga aag gaa      240
Glu Asn His Leu Arg His Cys Leu Ser Cys Ser Lys Cys Arg Lys Glu
 65                  70                  75                  80 atg ggt cag gtg gag atc tct tct tgc aca gtg gac cgg gac acc gtg      288
Met Gly Gln Val Glu Ile Ser Ser Cys Thr Val Asp Arg Asp Thr Val
                 85                  90                  95 tgt ggc tgc agg aag aac cag tac cgg cat tat tgg agt gaa aac ctt      336
Cys Gly Cys Arg Lys Asn Gln Tyr Arg His Tyr Trp Ser Glu Asn Leu
                100                 105                 110 ttc cag tgc ttc aat tgc agc ctc tgc ctc aat ggg acc gtg cac ctc      384
Phe Gln Cys Phe Asn Cys Ser Leu Cys Leu Asn Gly Thr Val His Leu
            115                 120                 125 tcc tgc cag gag aaa cag aac acc gtg tgc acc tgc cat gca ggt ttc      432
Ser Cys Gln Glu Lys Gln Asn Thr Val Cys Thr Cys His Ala Gly Phe
        130                 135                 140 ttt cta aga gaa aac gag tgt gtc tcc tgt agt aac tgt aag aaa agc      480
Phe Leu Arg Glu Asn Glu Cys Val Ser Cys Ser Asn Cys Lys Lys Ser
145                 150                 155                 160 ctg gag tgc acg aag ttg tgc cta ccc cag att gag aat                  519
Leu Glu Cys Thr Lys Leu Cys Leu Pro Gln Ile Glu Asn
                165                 170

<210> SEQ ID NO 16
<211> LENGTH: 173
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 16

Met Leu Val Pro His Leu Gly Asp Arg Glu Lys Arg Asp Ser Val Cys
 1               5                  10                  15

Pro Gln Gly Lys Tyr Ile His Pro Gln Asn Asn Ser Ile Cys Cys Thr
             20                  25                  30

Lys Cys His Lys Gly Thr Tyr Leu Tyr Asn Asp Cys Pro Gly Pro Gly
         35                  40                  45

Gln Asp Thr Asp Cys Arg Glu Cys Glu Ser Gly Ser Phe Thr Ala Ser
    50                  55                  60

Glu Asn His Leu Arg His Cys Leu Ser Cys Ser Lys Cys Arg Lys Glu
 65                  70                  75                  80

Met Gly Gln Val Glu Ile Ser Ser Cys Thr Val Asp Arg Asp Thr Val
                 85                  90                  95

Cys Gly Cys Arg Lys Asn Gln Tyr Arg His Tyr Trp Ser Glu Asn Leu
                100                 105                 110

Phe Gln Cys Phe Asn Cys Ser Leu Cys Leu Asn Gly Thr Val His Leu
            115                 120                 125

Ser Cys Gln Glu Lys Gln Asn Thr Val Cys Thr Cys His Ala Gly Phe
        130                 135                 140

Phe Leu Arg Glu Asn Glu Cys Val Ser Cys Ser Asn Cys Lys Lys Ser
```

```
                    145                 150                 155                 160
    Leu Glu Cys Thr Lys Leu Cys Leu Pro Gln Ile Glu Asn
                        165                 170

<210> SEQ ID NO 17
<211> LENGTH: 570
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(570)

<400> SEQUENCE: 17 atg ggc ctc tcc acc gtg cct gac ctg ctg ctg cca ctg gtg ctc ctg        48
Met Gly Leu Ser Thr Val Pro Asp Leu Leu Leu Pro Leu Val Leu Leu
  1               5                  10                  15 gag ctg ttg gtg gga ata tac ccc tca ggg gtt att gga gat agt gtg        96
Glu Leu Leu Val Gly Ile Tyr Pro Ser Gly Val Ile Gly Asp Ser Val
             20                  25                  30 tgt ccc caa gga aaa tat atc cac cct caa aat aat tcg att tgc tgt       144
Cys Pro Gln Gly Lys Tyr Ile His Pro Gln Asn Asn Ser Ile Cys Cys
         35                  40                  45 acc aag tgc cac aaa gga acc tac ttg tac aat gac tgt cca ggc ccg       192
Thr Lys Cys His Lys Gly Thr Tyr Leu Tyr Asn Asp Cys Pro Gly Pro
     50                  55                  60 ggg cag gat acg gac tgc agg gag tgt gag agc ggc tcc ttc acc gct       240
Gly Gln Asp Thr Asp Cys Arg Glu Cys Glu Ser Gly Ser Phe Thr Ala
 65                  70                  75                  80 tca gaa aac cac ctc aga cac tgc ctc agc tgc tcc aaa tgc cga aag       288
Ser Glu Asn His Leu Arg His Cys Leu Ser Cys Ser Lys Cys Arg Lys
                 85                  90                  95 gaa atg ggt cag gtg gag atc tct tct tgc aca gtg gac cgg gac acc       336
Glu Met Gly Gln Val Glu Ile Ser Ser Cys Thr Val Asp Arg Asp Thr
            100                 105                 110 gtg tgt ggc tgc agg aag aac cag tac cgg cat tat tgg agt gaa aac       384
Val Cys Gly Cys Arg Lys Asn Gln Tyr Arg His Tyr Trp Ser Glu Asn
        115                 120                 125 ctt ttc cag tgc ttc aat tgc agc ctc tgc ctc aat ggg acc gtg cac       432
Leu Phe Gln Cys Phe Asn Cys Ser Leu Cys Leu Asn Gly Thr Val His
    130                 135                 140 ctc tcc tgc cag gag aaa cag aac acc gtg tgc acc tgc cat gca ggt       480
Leu Ser Cys Gln Glu Lys Gln Asn Thr Val Cys Thr Cys His Ala Gly
145                 150                 155                 160 ttc ttt cta aga gaa aac gag tgt gtc tcc tgt agt aac tgt aag aaa       528
Phe Phe Leu Arg Glu Asn Glu Cys Val Ser Cys Ser Asn Cys Lys Lys
                165                 170                 175 agc ctg gag tgc acg aag ttg tgc cta ccc cag att gag aat                570
Ser Leu Glu Cys Thr Lys Leu Cys Leu Pro Gln Ile Glu Asn
            180                 185                 190

<210> SEQ ID NO 18
<211> LENGTH: 190
<212> TYPE: PRT
<213> ORGANISM: Artificial Sequence
<220> FEATURE:
<223> OTHER INFORMATION: Description of Artificial Sequence: recombinant
      TNF-BP sequence

<400> SEQUENCE: 18

Met Gly Leu Ser Thr Val Pro Asp Leu Leu Leu Pro Leu Val Leu Leu
  1               5                  10                  15
```

```
Glu Leu Leu Val Gly Ile Tyr Pro Ser Gly Val Ile Gly Asp Ser Val
             20                  25                  30

Cys Pro Gln Gly Lys Tyr Ile His Pro Gln Asn Asn Ser Ile Cys Cys
         35                  40                  45

Thr Lys Cys His Lys Gly Thr Tyr Leu Tyr Asn Asp Cys Pro Gly Pro
     50                  55                  60

Gly Gln Asp Thr Asp Cys Arg Glu Cys Glu Ser Gly Ser Phe Thr Ala
 65                  70                  75                  80

Ser Glu Asn His Leu Arg His Cys Leu Ser Cys Ser Lys Cys Arg Lys
                 85                  90                  95

Glu Met Gly Gln Val Glu Ile Ser Ser Cys Thr Val Asp Arg Asp Thr
            100                 105                 110

Val Cys Gly Cys Arg Lys Asn Gln Tyr Arg His Tyr Trp Ser Glu Asn
        115                 120                 125

Leu Phe Gln Cys Phe Asn Cys Ser Leu Cys Leu Asn Gly Thr Val His
    130                 135                 140

Leu Ser Cys Gln Glu Lys Gln Asn Thr Val Cys Thr Cys His Ala Gly
145                 150                 155                 160

Phe Phe Leu Arg Glu Asn Glu Cys Val Ser Cys Ser Asn Cys Lys Lys
                165                 170                 175

Ser Leu Glu Cys Thr Lys Leu Cys Leu Pro Gln Ile Glu Asn
            180                 185                 190

<210> SEQ ID NO 19
<211> LENGTH: 516
<212> TYPE: DNA
<213> ORGANISM: Artificial Sequence
<220> FEATURE:
<223> OTHER INFORMATION: Description of Artificial Sequence: recombinant
      TNF-BP sequence
<221> NAME/KEY: CDS
<222> LOCATION: (1)..(516)

<400> SEQUENCE: 19 atg gat agt gtg tgt ccc caa gga aaa tat atc cac cct caa aat aat      48
Met Asp Ser Val Cys Pro Gln Gly Lys Tyr Ile His Pro Gln Asn Asn
 1               5                  10                  15 tcg att tgc tgt acc aag tgc cac aaa gga acc tac ttg tac aat gac      96
Ser Ile Cys Cys Thr Lys Cys His Lys Gly Thr Tyr Leu Tyr Asn Asp
             20                  25                  30 tgt cca ggc ccg ggg cag gat acg gac tgc agg gag tgt gag agc ggc     144
Cys Pro Gly Pro Gly Gln Asp Thr Asp Cys Arg Glu Cys Glu Ser Gly
         35                  40                  45 tcc ttc acc gct tca gaa aac cac ctc aga cac tgc ctc agc tgc tcc     192
Ser Phe Thr Ala Ser Glu Asn His Leu Arg His Cys Leu Ser Cys Ser
     50                  55                  60 aaa tgc cga aag gaa atg ggt cag gtg gag atc tct tct tgc aca gtg     240
Lys Cys Arg Lys Glu Met Gly Gln Val Glu Ile Ser Ser Cys Thr Val
 65                  70                  75                  80 gac cgg gac acc gtg tgt ggc tgc agg aag aac cag tac cgg cat tat     288
Asp Arg Asp Thr Val Cys Gly Cys Arg Lys Asn Gln Tyr Arg His Tyr
                 85                  90                  95 tgg agt gaa aac ctt ttc cag tgc ttc aat tgc agc ctc tgc ctc aat     336
Trp Ser Glu Asn Leu Phe Gln Cys Phe Asn Cys Ser Leu Cys Leu Asn
            100                 105                 110 ggg acc gtg cac ctc tcc tgc cag gag aaa cag aac acc gtg tgc acc     384
Gly Thr Val His Leu Ser Cys Gln Glu Lys Gln Asn Thr Val Cys Thr
        115                 120                 125
```

```
tgc cat gca ggt ttc ttt cta aga gaa aac gag tgt gtc tcc tgt agt      432
Cys His Ala Gly Phe Phe Leu Arg Glu Asn Glu Cys Val Ser Cys Ser
    130                 135                 140 aac tgt aag aaa agc ctg gag tgc acg aag ttg tgc cta ccc cag att      480
Asn Cys Lys Lys Ser Leu Glu Cys Thr Lys Leu Cys Leu Pro Gln Ile
145                 150                 155                 160 gag aat gtt aag ggc act gag gac tca ggc acc aca                      516
Glu Asn Val Lys Gly Thr Glu Asp Ser Gly Thr Thr
                165                 170
```

<210> SEQ ID NO 20
<211> LENGTH: 172
<212> TYPE: PRT
<213> ORGANISM: Artificial Sequence
<220> FEATURE:
<223> OTHER INFORMATION: Description of Artificial Sequence: recombinant TNF-BP sequence

<400> SEQUENCE: 20

```
Met Asp Ser Val Cys Pro Gln Gly Lys Tyr Ile His Pro Gln Asn Asn
 1               5                  10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
            35                  40                  45

Ser Phe Thr Ala Ser Glu Asn His Leu Arg His Cys Leu Ser Cys Ser
        50                  55                  60

Lys Cys Arg Lys Glu Met Gly Gln Val Glu Ile Ser Ser Cys Thr Val
65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Asn Cys Ser Leu Cys Leu Asn
                100                 105                 110

Gly Thr Val His Leu Ser Cys Gln Glu Lys Gln Asn Thr Val Cys Thr
            115                 120                 125

Cys His Ala Gly Phe Phe Leu Arg Glu Asn Glu Cys Val Ser Cys Ser
    130                 135                 140

Asn Cys Lys Lys Ser Leu Glu Cys Thr Lys Leu Cys Leu Pro Gln Ile
145                 150                 155                 160

Glu Asn Val Lys Gly Thr Glu Asp Ser Gly Thr Thr
                165                 170
```

<210> SEQ ID NO 21
<211> LENGTH: 1334
<212> TYPE: DNA
<213> ORGANISM: Artificial Sequence
<220> FEATURE:
<223> OTHER INFORMATION: Description of Artificial Sequence: cDNA insert of lambdaTNF-BP15 and pTNF-BP15 vectors
<221> NAME/KEY: CDS
<222> LOCATION: (213)..(1325)

<400> SEQUENCE: 21

```
gaattctctg gactgaggct ccagttctgg cctttggggt tcaagatcac tgggaccagg     60
ccgtgatctc tatgcccgag tctcaaccct caactgtcac cccaaggcac ttggacgtc    120 ctggacagac cgagtcccgg gaagcccag cactgccgct gccacactgc cctgagccca    180
aatgggcgag tgagaggcca tagctgtctg gc atg ggc ctc tcc acc gtg cct     233
                                   Met Gly Leu Ser Thr Val Pro
                                    1               5
```

```
gac ctg ctg ctg cca ctg gtg ttc ctg gag ctg ttg gtg gga ata tac    281
Asp Leu Leu Leu Pro Leu Val Phe Leu Glu Leu Leu Val Gly Ile Tyr
         10              15              20 ccc tca ggg gtt att gga ctg gtc cct cac cta ggg gac agg gag aag    329
Pro Ser Gly Val Ile Gly Leu Val Pro His Leu Gly Asp Arg Glu Lys
     25              30              35 aga gat agt gtg tgt ccc caa gga aaa tat atc cac cct caa aat aat    377
Arg Asp Ser Val Cys Pro Gln Gly Lys Tyr Ile His Pro Gln Asn Asn
40              45              50              55 tcg att tgc tgt acc aag tgc cac aaa gga acc tac ttg tac aat gac    425
Ser Ile Cys Cys Thr Lys Cys His Lys Gly Thr Tyr Leu Tyr Asn Asp
             60              65              70 tgt cca ggc ccg ggg cag gat acg gac tgc agg gag tgt gag agc ggc    473
Cys Pro Gly Pro Gly Gln Asp Thr Asp Cys Arg Glu Cys Glu Ser Gly
         75              80              85 tcc ttc acc gct tca gaa aac cac ctc aga cac tgc ctc agc tgc tcc    521
Ser Phe Thr Ala Ser Glu Asn His Leu Arg His Cys Leu Ser Cys Ser
     90              95             100 aaa tgc cga aag gaa atc ggt cag gtg gag atc tct tct tgc aca gtg    569
Lys Cys Arg Lys Glu Ile Gly Gln Val Glu Ile Ser Ser Cys Thr Val
105             110             115 gac cgg gac acc gtg tgt ggc tgc agg aag aac cag tac cgg cat tat    617
Asp Arg Asp Thr Val Cys Gly Cys Arg Lys Asn Gln Tyr Arg His Tyr
120             125             130             135 tgg agt gaa aac ctt ttc cag tgc ttc aat tgc agc ctc tgc ctc aat    665
Trp Ser Glu Asn Leu Phe Gln Cys Phe Asn Cys Ser Leu Cys Leu Asn
                140             145             150 ggg acc gtg cac ctc tcc tgc cag gag aaa cag aac acc gtg tgc acc    713
Gly Thr Val His Leu Ser Cys Gln Glu Lys Gln Asn Thr Val Cys Thr
             155             160             165 tgc cat gca ggt ttc ttt cta aga gaa aac gag tgt gtc tcc tgt agt    761
Cys His Ala Gly Phe Phe Leu Arg Glu Asn Glu Cys Val Ser Cys Ser
         170             175             180 aac tgt aag aaa agc ctg gag tgc agg aag ttg tgc cta ccc cag att    809
Asn Cys Lys Lys Ser Leu Glu Cys Arg Lys Leu Cys Leu Pro Gln Ile
     185             190             195 gag aat gtt aag ggc act gag gac tca ggc acc aca gtg ctg ttg ccc    857
Glu Asn Val Lys Gly Thr Glu Asp Ser Gly Thr Thr Val Leu Leu Pro
200             205             210             215 ctg gtc att ttc ttt ggt ctt tgc ctt tta tcc ctc ctc ttc att ggt    905
Leu Val Ile Phe Phe Gly Leu Cys Leu Leu Ser Leu Leu Phe Ile Gly
                220             225             230 tta atg tat cgc tac caa cgg tgg aag tcc aag ctc tac tcc att gtt    953
Leu Met Tyr Arg Tyr Gln Arg Trp Lys Ser Lys Leu Tyr Ser Ile Val
             235             240             245 tgt ggg aaa tcg aca cct gaa aaa gag ggg gag ctt gaa gga act act   1001
Cys Gly Lys Ser Thr Pro Glu Lys Glu Gly Glu Leu Glu Gly Thr Thr
         250             255             260 act aag ccc ctg gcc cca aac cca agc ttc agt ccc act cca ggc ttc   1049
Thr Lys Pro Leu Ala Pro Asn Pro Ser Phe Ser Pro Thr Pro Gly Phe
     265             270             275 acc ccc acc ctg ggc ttc agt ccc gtg ccc agt tcc acc ttc acc tcc   1097
Thr Pro Thr Leu Gly Phe Ser Pro Val Pro Ser Ser Thr Phe Thr Ser
280             285             290             295 agc tcc acc tat acc ccc ggt gac tgt ccc aac ttt gcg gct ccc cgc   1145
Ser Ser Thr Tyr Thr Pro Gly Asp Cys Pro Asn Phe Ala Ala Pro Arg
                300             305             310 aga gag gtg gca cca ccc tat cag ggg gct gac ccc atc ctt gcg aca   1193
Arg Glu Val Ala Pro Pro Tyr Gln Gly Ala Asp Pro Ile Leu Ala Thr
             315             320             325
```

```
gcc ctc gcc tcc gac ccc atc ccc aac ccc ctt cag aag tgg gag gac    1241
Ala Leu Ala Ser Asp Pro Ile Pro Asn Pro Leu Gln Lys Trp Glu Asp
        330                 335                 340 agc gcc cac aag cca cag agc cta gac act gat gac ccc gcg acg ctg    1289
Ser Ala His Lys Pro Gln Ser Leu Asp Thr Asp Asp Pro Ala Thr Leu
345                 350                 355 tac gcc gtg gtg gag aac gtg ccc ccg ttg cgc tgg aaggaattc          1334
Tyr Ala Val Val Glu Asn Val Pro Pro Leu Arg Trp
360                 365                 370

<210> SEQ ID NO 22
<211> LENGTH: 371
<212> TYPE: PRT
<213> ORGANISM: Artificial Sequence
<220> FEATURE:
<223> OTHER INFORMATION: Description of Artificial Sequence: cDNA insert
      of lambdaTNF-BP15 and pTNF-BP15 vectors

<400> SEQUENCE: 22

Met Gly Leu Ser Thr Val Pro Asp Leu Leu Leu Pro Leu Val Phe Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
 65                 70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Ile Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Arg
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
```

```
                    290              295              300
Pro Asn Phe Ala Ala Pro Arg Arg Glu Val Ala Pro Pro Tyr Gln Gly
305                  310                  315                  320

Ala Asp Pro Ile Leu Ala Thr Ala Leu Ala Ser Asp Pro Ile Pro Asn
                325                  330                  335

Pro Leu Gln Lys Trp Glu Asp Ser Ala His Lys Pro Gln Ser Leu Asp
            340                  345                  350

Thr Asp Asp Pro Ala Thr Leu Tyr Ala Val Val Glu Asn Val Pro Pro
        355                  360                  365

Leu Arg Trp
    370

<210> SEQ ID NO 23
<211> LENGTH: 6414
<212> TYPE: DNA
<213> ORGANISM: Artificial Sequence
<220> FEATURE:
<223> OTHER INFORMATION: Description of Artificial Sequence: pADCMV1
      vector
<221> NAME/KEY: unsure
<222> LOCATION: (344)
<223> OTHER INFORMATION: "n" can be a, g, c, or t
<221> NAME/KEY: unsure
<222> LOCATION: (4157)
<223> OTHER INFORMATION: "n" can be a, g, c, or t
<221> NAME/KEY: unsure
<222> LOCATION: (5135)
<223> OTHER INFORMATION: "n" can be a, g, c, or t
<221> NAME/KEY: unsure
<222> LOCATION: (6255)
<223> OTHER INFORMATION: "n" can be a, g, c, or t

<400> SEQUENCE: 23
tcgacattga ttattgacta gttattaata gtaatcaatt acggggtcat tagttcatag      60
cccatatatg gagttccgcg ttacataact tacggtaaat ggcccgcctc gctgaccgcc    120
caacgacccc cgcccattga cgtcaataat gacgtatgtt cccatagtaa cgccaatagg    180
gactttccat tgacgtcaat gggtggagta tttacggtaa actgcccact tggcagtaca    240
tcaagtgtat catatgccaa gtacgccccc tattgacgtc aatgacggta aatggcccgc    300
ctggcattat gcccagtaca tgaccttatg gactttcct actnggcagt acatctacgt    360
attagtcatc gctattacca tggtgatgcg gttttggcag tacatcaatg ggcgtggata    420
gcggtttgac tcacggggat ttccaagtct ccaccccatt gacgtcaatg ggagtttgtt    480
ttggcaccaa aatcaacggg actttccaaa atgtcgtaac aactccgccc cattgacgca    540
aatgggcggt aggcgtgtac ggtgggaggt ctatataagc agagctctct ggctaactag    600
agaacccact gcttaactgg cttatcgaaa ttaatacgac tcactatagg gagacccaag    660
cttctgcagg tcgacatcga tggatccggt acctcgagcg cgaattctct agaggatctt    720
tgtgaaggaa ccttacttct gtggtgtgac ataattggac aaactaccta cagagattta    780
aagctctaag gtaaatataa aattttttaag tgtataatgt gttaaactac tgattctaat    840
tgtttgtgta tttagattc caacctatgg aactgatgaa tgggagcagt ggtggaatgc    900
ctttaatgag gaaaacctgt tttgctcaga agaaatgcca tctagtgatg atgaggctac    960
tgctgactct caacattcta ctcctccaaa aaagaagaga aaggtagaag accccaagga   1020
ctttccttca gaattgctaa gttttttgag tcatgctgtg tttagtaata gaactcttgc   1080
ttgctttgct atttacacca caaggaaaaa agctgcactg ctatacaaga aaattatgga   1140
aaaatatttg atgtatagtg ccttgactag agatcataat cagccatacc acatttgtag   1200
```

```
aggtttttact tgctttaaaa aacctcccac acctccccct gaacctgaaa cataaaatga   1260
atgcaattgt tgttgttaac ttgtttattg cagcttataa tggttacaaa taaagcaata   1320
gcatcacaaa tttcacaaat aaagcatttt tttcactgca ttctagttgt ggtttgtcca   1380
aactcatcaa tgtatcttat catgtctgga tcaattctga gaaactagcc ttaaagacag   1440
acagctttgt tctagtcagc caggcaagca tatgtaaata aagttcctca gggaactgag   1500
gttaaaagat gtatcctgga cctgccagac ctggccattc acgtaaacag aagattccgc   1560
ctcaagttcc ggttaacaac aggaggcaac gagatctcaa atctattact tctaatcggg   1620
taattaaaac ctttcaacta aaacacggac ccacggatgt cacccacttt tccttccccg   1680
gctccgccct tctcagtact ccccaccatt aggctcgcta ctccacctcc acttccgggc   1740
gcgacaccca cgtgccctct cccacccgac gctaaccccg ccctgcccg tctgaccccg    1800 cccaccacct ggccccgccc cgttgaggac agaagaaacc ccgggcagcc gcagccaagg   1860
cggacgggta gacgctgggg gcgctgagga gtcgtcctct accttctctg ctggctcggt   1920
gggggacgcg gtggatctca ggcttccgga agactggaag aaccggctca gaaccgcttg   1980
tctccgcggg gcttgggcgg cggaagaatg gccgctagac gcggacttgg tgcgaggcat   2040
cgcaggatgc agaagagcaa gcccgccggg agcgcgcggc tgtactaccc cgcgcctgga   2100
gcggccacgc cggactgggc ggggccggcc tggtggaggc ggagtctgac ctcgtggagg   2160
cggggcctct gatgttcaaa taggatgcta ggcttgttga ggcgtggcct ccgattcaca   2220
agtgggaagc agcgccgggc gactgcaatt tcgcgccaaa cttgggggaa gcacagcgta   2280
caggctgcct agtgatcgc tgctgctgtc atggttcgac cgctgaactg catcgtcgcc    2340
gtgtcccaga atatgggcat cggcaagaac ggagaccttc cctggccaat gctcaggtac   2400
tggctggatt gggttaggga accgaggcg gttcgctgaa tcgggtcgag cacttggcgg    2460
agacgcgcgg gccaactact tagggacagt catgaggggt aggcccgccg gctgctgccc   2520
ttgcccatgc ccgcggtgat ccccatgctg tgccagcctt tgcccagagg cgctctagct   2580
gggagcaaag tccggtcact gggcagcacc acccccgga cttgcatggg tagccgctga    2640
gatggagcct gagcacacgt gacagggtcc ctgttaacgc agtgtttctc taactttcag   2700
gaacgagttc aagtacttcc aaagaatgac caccacctcc tcagtggaag gtaaacagaa   2760
cctggtgatt atgggccgga aaacctggtt ctccattcct gagaagaatc gacctttaaa   2820
ggacagaatt aatatagttc tcagtagaga gctcaaggaa ccaccacaag gagctcattt   2880
tcttgccaaa agtctggacc atgccttaaa acttattgaa caaccagagt tagcagataa   2940
agtggacatg gtttggatag ttggaggcag ttccgtttac aaggaagcca tgaatcagcc   3000
aggccatctc agactctttg tgacaaggat catgcaggaa tttgaaagtg acacgttctt   3060
cccagaaatt gatttggaga aatataaact tctcccagag tacccagggg tcctttctga   3120
agtccaggag gaaaaaggca tcaagtataa atttgaagtc tatgagaaga aggctaaca    3180 gaaagatact tgctgattga cttcaagttc tactgctttc ctcctaaaat tatgcatttt   3240
tacaagacca tgggacttgt gttggctttta gatcctgtgc atcctgggca actgttgtac   3300
tctaagccac tccccaaagt catgcccag ccctgtata attctaaaca attagaatta    3360
ttttcatttt cattagtcta accaggttat attaaatata ctttaagaaa caccatttgc   3420
cataaagttc tcaatgcccc tcccatgcag cctcaagtgg ctcccagca gatgcatagg    3480 gtagtgtgtg tacaagagac cccaaagaca tagagcccct gagagcatga gctgatatgg   3540
```

```
gggctcatag agataggagc tagatgaata agtacaaagg gcagaaatgg gttttaacca    3600
gcagagctag aactcagact ttaaagaaaa ttagatcaaa gtagagactg aattattctg    3660
cacatcagac tctgagcaga gttctgttca ctcagacaga aaatgggtaa attgagagct    3720
ggctccattg tgctccttag agatgggagc aggtggagga ttatataagg tctggaacat    3780
ttaacttctc cgtttctcat cttcagtgag attccaaggg atactacaat tctgtggaat    3840
gtgtgtcagt tagggtgtgg aaagtcccca ggctccccag caggcagaag tatgcaaagc    3900
atgcatctca attagtcagc aaccaggtgt ggaaagtccc caggctcccc agcaggcaga    3960
agtatgcaaa gcatgcatct caattagtca gcaaccatag tcccgcccct aactccgccc    4020
atcccgcccc taactccgcc cagttccgcc cattctccgc cccatggctg actaattttt    4080
tttatttatg cagaggccga ggcgcctctg agctattcca gaagtagtga ggaggctttt    4140
ttggaggcct aggcttntgc aaaaaagcta attcagcctg aatggcgaat gggacgcgcc    4200
ctgtagcggc gcattaagcg cggcgggtgt ggtggttacg cgcagcgtga ccgctacact    4260
tgccagcgcc ctagcgcccg ctcctttcgc tttcttccct tcctttctcg ccacgttcgc    4320
cggctttccc cgtcaagctc taaatcgggg ctccctttta gggttccgat ttagtgcttt    4380
acggcacctc gaccccaaaa acttgattag ggtgatggtt cacgtagtgg gccatcgccc    4440
tgatagacgt ttttcgccc tttgacgttg gagtccacgt tctttaatag tggactcttg    4500
ttccaaactg gaacaacact caaccctatc tcggtctatt cttttgattt ataagggatt    4560
ttgccgattt cggcctattg gttaaaaaat gagctgattt aacaaaaatt taacgcgaat    4620
tttaacaaaa tattaacgtt tacaatttca ggtggcactt ttcggggaaa tgtgcgcgga    4680
acccctattt gtttattttt ctaaatacat tcaaatatgt atccgctcat gagacaataa    4740
ccctgataaa tgcttcaata atattgaaaa aggaagagta tgagtattca acatttccgt    4800
gtcgccctta ttcccttttt tgcggcattt tgccttcctg ttttttgctca cccagaaacg    4860
ctggtgaaag taaaagatgc tgaagatcag ttgggtgcac gagtgggtta catcgaactg    4920
gatctcaaca gcggtaagat ccttgagagt tttcgccccg aagaacgttt tccaatgatg    4980
agcacttttta aagttctgct atgtggcgcg gtattatccc gtattgacgc cgggcaagag    5040
caactcggtc gccgcataca ctattctcag aatgacttgg ttgagtactc accagtcaca    5100
gaaaagcatc ttacggatgg catgacagta agagnattat gcagtgctgc cataaccatg    5160
agtgataaca ctgcggccaa cttacttctg acaacgatcg gaggaccgaa ggagctaacc    5220
gcttttttgc acaacatggg ggatcatgta actcgccttg atcgttggga accggagctg    5280
aatgaagcca taccaaacga cgagcgtgac accacgatgc ctgtagcaat ggcaacaacg    5340
ttgcgcaaac tattaactgg cgaactactt actctagctt cccggcaaca attaatagac    5400
tggatggagg cggataaagt tgcaggacca cttctgcgct cggcccttcc ggctggctgg    5460
tttattgctg ataaatctgg agccggtgag cgtgggtctc gcggtatcat tgcagcactg    5520
gggccagatg gtaagccctc ccgtatcgta gttatctaca cgacggggag tcaggcaact    5580
atggatgaac gaaatagaca gatcgctgag ataggtgcct cactgattaa gcattggtaa    5640
ctgtcagacc aagtttactc atatatactt tagattgatt taaaacttca tttttaattt    5700
aaaaggatct aggtgaagat cctttttgat aatctcatga ccaaaatccc ttaacgtgag    5760
ttttcgttcc actgagcgtc agaccccgta gaaaagatca aggatcttc ttgagatcct    5820
ttttttctgc gcgtaatctg ctgcttgcaa acaaaaaaac caccgctacc agcggtggtt    5880
tgtttgccgg atcaagagct accaactctt tttccgaagg taactggctt cagcagagcg    5940
```

-continued

```
cagataccaa atactgtcct tctagtgtag ccgtagttag gccaccactt caagaactct    6000
gtagcaccgc ctacatacct cgctctgcta atcctgttac cagtggctgc tgccagtggc    6060
gataagtcgt gtcttaccgg gttggactca agacgatagt taccggataa ggcgcagcgg    6120
tcgggctgaa cggggggttc gtgcacacag cccagcttgg agcgaacgac ctacaccgaa    6180
ctgagatacc tacagcgtga gcattgagaa agcgccacgc ttcccgaagg gagaaaggcg    6240
gacaggtatc cggtnagcgg cagggtcgga acaggagagc gcacgaggga gcttccaggg    6300
ggaaacgcct ggtatcttta tagtcctgtc gggtttcgcc acctctgact tgagcgtcga    6360
tttttgtgat gctcgtcagg ggggcggagc ctatggaaaa acgccagcaa cgcc          6414
```

<210> SEQ ID NO 24
<211> LENGTH: 2173
<212> TYPE: DNA
<213> ORGANISM: Artificial Sequence
<220> FEATURE:
<223> OTHER INFORMATION: Description of Artificial Sequence: raTNF-R8
<221> NAME/KEY: CDS
<222> LOCATION: (245)..(1627)

<400> SEQUENCE: 24

```
gaattccttt tctccgagtt ttctgaactc tggctcatga tcgggcttac tggatacgag     60
aatcctggag gaccgtaccc tgatttccat ctacctctga ctttgagcct ttctaacccg    120
gggctcacgc tgccaacacc cgggccacct ggtccgatcg tcttacttca ttcaccagcg    180
ttgccaattg ctgccctgtc cccagcccca atggggagt gagagaggcc actgccggcc     240 ggac atg ggt ctc ccc atc gtg cct ggc ctg ctg ctg tca ctg gtg ctc    289
     Met Gly Leu Pro Ile Val Pro Gly Leu Leu Leu Ser Leu Val Leu
       1               5                  10                  15 ctg gct ctg ctg atg ggg ata cac cca tca ggg gtc acc gga ctg gtt    337
Leu Ala Leu Leu Met Gly Ile His Pro Ser Gly Val Thr Gly Leu Val
                20                  25                  30 cct tct ctt ggt gac cgg gag aag agg gat aat ttg tgt ccc cag gga    385
Pro Ser Leu Gly Asp Arg Glu Lys Arg Asp Asn Leu Cys Pro Gln Gly
            35                  40                  45 aag tat gcc cat cca aag aat aat tcc atc tgc tgc acc aag tgc cac    433
Lys Tyr Ala His Pro Lys Asn Asn Ser Ile Cys Cys Thr Lys Cys His
        50                  55                  60 aaa gga acc tac ttg gtg agt gac tgt cca agc cca ggg cag gaa aca    481
Lys Gly Thr Tyr Leu Val Ser Asp Cys Pro Ser Pro Gly Gln Glu Thr
    65                  70                  75 gtc tgc gag ctc tct cat aaa ggc acc ttt aca gct tcg cag aac cac    529
Val Cys Glu Leu Ser His Lys Gly Thr Phe Thr Ala Ser Gln Asn His
80                  85                  90                  95 gtc aga cag tgt ctc agt tgc aag aca tgt cgg aaa gaa atg ttc cag    577
Val Arg Gln Cys Leu Ser Cys Lys Thr Cys Arg Lys Glu Met Phe Gln
                100                 105                 110 gtg gag att tct cct tgc aaa gct gac atg gac acc gtg tgt ggc tgc    625
Val Glu Ile Ser Pro Cys Lys Ala Asp Met Asp Thr Val Cys Gly Cys
            115                 120                 125 aag aag aac caa ttc cag cgc tac ctg agt gag acg cat ttc cag tgt    673
Lys Lys Asn Gln Phe Gln Arg Tyr Leu Ser Glu Thr His Phe Gln Cys
        130                 135                 140 gtg gac tgc agc ccc tgc ttc aat ggc acc gtg aca atc ccc tgt aag    721
Val Asp Cys Ser Pro Cys Phe Asn Gly Thr Val Thr Ile Pro Cys Lys
    145                 150                 155 gag aaa cag aac acc gtg tgt aac tgc cac gca gga ttc ttt cta agc    769
Glu Lys Gln Asn Thr Val Cys Asn Cys His Ala Gly Phe Phe Leu Ser
```

```
                160                 165                 170                 175
gga aat gag tgc acc cct tgc agc cac tgc aag aaa aat cag gaa tgt         817
Gly Asn Glu Cys Thr Pro Cys Ser His Cys Lys Lys Asn Gln Glu Cys
                    180                 185                 190 atg aag ctg tgc cta cct cca gtt gca aat gtc aca aac ccc cag gac         865
Met Lys Leu Cys Leu Pro Pro Val Ala Asn Val Thr Asn Pro Gln Asp
            195                 200                 205 tca ggt act gcc gtg ctg ttg cct ctg gtt atc ttc cta ggt ctt tgc         913
Ser Gly Thr Ala Val Leu Leu Pro Leu Val Ile Phe Leu Gly Leu Cys
        210                 215                 220 ctt tta ttc ttt atc tgc atc agt cta ctg tgc cga tat ccc cag tgg         961
Leu Leu Phe Phe Ile Cys Ile Ser Leu Leu Cys Arg Tyr Pro Gln Trp
    225                 230                 235 agg ccc agg gtc tac tcc atc att tgt agg gat tca gct cct gtc aaa        1009
Arg Pro Arg Val Tyr Ser Ile Ile Cys Arg Asp Ser Ala Pro Val Lys
240                 245                 250                 255 gag gtg gag ggt gaa gga att gtt act aag ccc cta act cca gcc tct        1057
Glu Val Glu Gly Glu Gly Ile Val Thr Lys Pro Leu Thr Pro Ala Ser
                260                 265                 270 atc cca gcc ttc agc ccc aac ccc ggc ttc aac ccc act ctg ggc ttc        1105
Ile Pro Ala Phe Ser Pro Asn Pro Gly Phe Asn Pro Thr Leu Gly Phe
            275                 280                 285 agc acc acc cca cgc ttc agt cat cct gtc tcc agt acc ccc atc agc        1153
Ser Thr Thr Pro Arg Phe Ser His Pro Val Ser Ser Thr Pro Ile Ser
        290                 295                 300 ccc gtc ttc ggt cct agt aac tgg cac aac ttc gtg cca cct gta aga        1201
Pro Val Phe Gly Pro Ser Asn Trp His Asn Phe Val Pro Pro Val Arg
    305                 310                 315 gag gtg gtc cca acc cag ggt gct gac cct ctc ctc tac gga tcc ctc        1249
Glu Val Val Pro Thr Gln Gly Ala Asp Pro Leu Leu Tyr Gly Ser Leu
320                 325                 330                 335 aac cct gtg cca atc ccc gcc cct gtt cgg aaa tgg gaa gac gtc gtc        1297
Asn Pro Val Pro Ile Pro Ala Pro Val Arg Lys Trp Glu Asp Val Val
                340                 345                 350 gcg gcc cag cca caa cgg ctt gac act gca gac cct gcg atg ctg tat        1345
Ala Ala Gln Pro Gln Arg Leu Asp Thr Ala Asp Pro Ala Met Leu Tyr
            355                 360                 365 gct gtg gtg gat ggc gtg cct ccg aca cgc tgg aag gag ttc atg cgg        1393
Ala Val Val Asp Gly Val Pro Pro Thr Arg Trp Lys Glu Phe Met Arg
        370                 375                 380 ctc ctg ggg ctg agc gag cac gag atc gag cgg ttg gag ctg cag aac        1441
Leu Leu Gly Leu Ser Glu His Glu Ile Glu Arg Leu Glu Leu Gln Asn
    385                 390                 395 ggg cgt tgc ctc cgc gag gct cat tac agc atg ctg gaa gcc tgg cgg        1489
Gly Arg Cys Leu Arg Glu Ala His Tyr Ser Met Leu Glu Ala Trp Arg
400                 405                 410                 415 cgc cgc aca ccg cga cac gag gcc acg ctg gac gta gtg ggc cgc gtg        1537
Arg Arg Thr Pro Arg His Glu Ala Thr Leu Asp Val Val Gly Arg Val
                420                 425                 430 ctt tgc gac atg aac ctg cgt ggc tgc ctg gag aac atc cgc gag act        1585
Leu Cys Asp Met Asn Leu Arg Gly Cys Leu Glu Asn Ile Arg Glu Thr
            435                 440                 445 cta gaa agc cct gcc cac tcg tcc acg acc cac ctc ccg cga                1627
Leu Glu Ser Pro Ala His Ser Ser Thr Thr His Leu Pro Arg
        450                 455                 460 taaggccaca cccccacctc aggaacggga ctcgaaggac catcctgcta gatgccctgc     1687
ttccctgtga acctcctctt tggtcctcta gggggcaggc tcgatctggc aggctcgatc     1747
tggcagccac ttccttggtg ctaccgactt ggtgtacata gcttttccca gctgccgagg     1807
```

```
acagcctgtg ccagccactt gtgcatggca gggaagtgtg ccatctgctc ccagacagct    1867
gagggtgcca aaagccagga gaggtgattg tggagaaaaa gcacaatcta tctgataccc    1927
acttgggatg caaggaccca aacaaagctt ctcagggcct cctcagttga tttctgggcc    1987
cttttcacag tagataaaac agtctttgta ttgattatat cacactaatg gatgaacggt    2047
tgaactccct aaggtagggg caagcacaga acagtgggt ctccagctgg agcccccgac     2107
tcttgtaaat acactaaaaa tctaaaagtg aaaaaaaaaa aaaaaaaaaa aaaaaaaag     2167 gaattc                                                               2173
```

<210> SEQ ID NO 25
<211> LENGTH: 461
<212> TYPE: PRT
<213> ORGANISM: Artificial Sequence
<220> FEATURE:
<223> OTHER INFORMATION: Description of Artificial Sequence: raTNF-R8

<400> SEQUENCE: 25

```
Met Gly Leu Pro Ile Val Pro Gly Leu Leu Ser Leu Val Leu Leu
 1               5                  10                  15

Ala Leu Leu Met Gly Ile His Pro Ser Gly Val Thr Gly Leu Val Pro
                20                  25                  30

Ser Leu Gly Asp Arg Glu Lys Arg Asp Asn Leu Cys Pro Gln Gly Lys
            35                  40                  45

Tyr Ala His Pro Lys Asn Asn Ser Ile Cys Cys Thr Lys Cys His Lys
        50                  55                  60

Gly Thr Tyr Leu Val Ser Asp Cys Pro Ser Pro Gly Gln Glu Thr Val
    65                  70                  75                  80

Cys Glu Leu Ser His Lys Gly Thr Phe Thr Ala Ser Gln Asn His Val
                85                  90                  95

Arg Gln Cys Leu Ser Cys Lys Thr Cys Arg Lys Glu Met Phe Gln Val
                100                 105                 110

Glu Ile Ser Pro Cys Lys Ala Asp Met Asp Thr Val Cys Gly Cys Lys
            115                 120                 125

Lys Asn Gln Phe Gln Arg Tyr Leu Ser Glu Thr His Phe Gln Cys Val
        130                 135                 140

Asp Cys Ser Pro Cys Phe Asn Gly Thr Val Thr Ile Pro Cys Lys Glu
145                 150                 155                 160

Lys Gln Asn Thr Val Cys Asn Cys His Ala Gly Phe Phe Leu Ser Gly
                165                 170                 175

Asn Glu Cys Thr Pro Cys Ser His Cys Lys Lys Asn Gln Glu Cys Met
            180                 185                 190

Lys Leu Cys Leu Pro Pro Val Ala Asn Val Thr Asn Pro Gln Asp Ser
        195                 200                 205

Gly Thr Ala Val Leu Leu Pro Leu Val Ile Phe Leu Gly Leu Cys Leu
    210                 215                 220

Leu Phe Phe Ile Cys Ile Ser Leu Leu Cys Arg Tyr Pro Gln Trp Arg
225                 230                 235                 240

Pro Arg Val Tyr Ser Ile Ile Cys Arg Asp Ser Ala Pro Val Lys Glu
                245                 250                 255

Val Glu Gly Glu Gly Ile Val Thr Lys Pro Leu Thr Pro Ala Ser Ile
            260                 265                 270

Pro Ala Phe Ser Pro Asn Pro Gly Phe Asn Pro Thr Leu Gly Phe Ser
        275                 280                 285
```

-continued

```
Thr Thr Pro Arg Phe Ser His Pro Val Ser Thr Pro Ile Ser Pro
    290                 295                 300
Val Phe Gly Pro Ser Asn Trp His Asn Phe Val Pro Pro Val Arg Glu
305                 310                 315                 320
Val Val Pro Thr Gln Gly Ala Asp Pro Leu Leu Tyr Gly Ser Leu Asn
                325                 330                 335
Pro Val Pro Ile Pro Ala Pro Val Arg Lys Trp Glu Asp Val Ala
            340                 345                 350
Ala Gln Pro Gln Arg Leu Asp Thr Ala Asp Pro Ala Met Leu Tyr Ala
            355                 360                 365
Val Val Asp Gly Val Pro Pro Thr Arg Trp Lys Glu Phe Met Arg Leu
370                 375                 380
Leu Gly Leu Ser Glu His Glu Ile Glu Arg Leu Glu Leu Gln Asn Gly
385                 390                 395                 400
Arg Cys Leu Arg Glu Ala His Tyr Ser Met Leu Glu Ala Trp Arg Arg
                405                 410                 415
Arg Thr Pro Arg His Glu Ala Thr Leu Asp Val Val Gly Arg Val Leu
                420                 425                 430
Cys Asp Met Asn Leu Arg Gly Cys Leu Glu Asn Ile Arg Glu Thr Leu
            435                 440                 445
Glu Ser Pro Ala His Ser Ser Thr His Leu Pro Arg
    450                 455                 460

<210> SEQ ID NO 26
<211> LENGTH: 2141
<212> TYPE: DNA
<213> ORGANISM: Artificial Sequence
<220> FEATURE:
<223> OTHER INFORMATION: Description of Artificial Sequence: human TNF-R
      in lTNF-R2
<221> NAME/KEY: CDS
<222> LOCATION: (213)..(1577)

<400> SEQUENCE: 26
gaattctctg gactgaggct ccagttctgg cctttggggt tcaagatcac tgggaccagg      60
ccgtgatctc tatgcccgag tctcaaccct caactgtcac cccaaggcac ttggacgtc      120 ctggacagac cgagtcccgg gaagcccag cactgccgct gccacactgc cctgagccca      180
katgggggag tgagaggcca tagctgtctg gc atg ggc ctc tcc acc gtg cct      233
                                   Met Gly Leu Ser Thr Val Pro
                                    1               5 gac ctg ctg ctg cca ctg gtg ctc ctg gag ctg ttg gtg gga ata tac      281
Asp Leu Leu Leu Pro Leu Val Leu Leu Glu Leu Leu Val Gly Ile Tyr
    10                  15                  20 ccc tca ggg gtt att gga ctg gtc cct cac cta ggg gac agg gag aag      329
Pro Ser Gly Val Ile Gly Leu Val Pro His Leu Gly Asp Arg Glu Lys
25                  30                  35 aga gat agt gtg tgt ccc caa gga aaa tat atc cac cct caa aat aat      377
Arg Asp Ser Val Cys Pro Gln Gly Lys Tyr Ile His Pro Gln Asn Asn
40                  45                  50                  55 tcg att tgc tgt acc aag tgc cac aaa gga acc tac ttg tac aat gac      425
Ser Ile Cys Cys Thr Lys Cys His Lys Gly Thr Tyr Leu Tyr Asn Asp
                60                  65                  70 tgt cca ggc ccg ggg cag gat acg gac tgc agg gag tgt gag agc ggc      473
Cys Pro Gly Pro Gly Gln Asp Thr Asp Cys Arg Glu Cys Glu Ser Gly
            75                  80                  85 tcc ttc acc gct tca gaa aac cac ctc aga cac tgc ctc agc tgc tcc      521
Ser Phe Thr Ala Ser Glu Asn His Leu Arg His Cys Leu Ser Cys Ser
        90                  95                  100
```

-continued

```
aaa tgc cga aag gaa atg ggt cag gtg gag atc tct tct tgc aca gtg      569
Lys Cys Arg Lys Glu Met Gly Gln Val Glu Ile Ser Ser Cys Thr Val
105                 110                 115 gac cgg gac acc gtg tgt ggc tgc agg aag aac cag tac cgg cat tat      617
Asp Arg Asp Thr Val Cys Gly Cys Arg Lys Asn Gln Tyr Arg His Tyr
120                 125                 130                 135 tgg agt gaa aac ctt ttc cag tgc ttc aat tgc agc ctc tgc ctc aat      665
Trp Ser Glu Asn Leu Phe Gln Cys Phe Asn Cys Ser Leu Cys Leu Asn
                140                 145                 150 ggg acc gtg cac ctc tcc tgc cag gag aaa cag aac acc gtg tgc acc      713
Gly Thr Val His Leu Ser Cys Gln Glu Lys Gln Asn Thr Val Cys Thr
        155                 160                 165 tgc cat gca ggt ttc ttt cta aga gaa aac gag tgt gtc tcc tgt agt      761
Cys His Ala Gly Phe Phe Leu Arg Glu Asn Glu Cys Val Ser Cys Ser
170                 175                 180 aac tgt aag aaa agc ctg gag tgc acg aag ttg tgc cta ccc cag att      809
Asn Cys Lys Lys Ser Leu Glu Cys Thr Lys Leu Cys Leu Pro Gln Ile
185                 190                 195 gag aat gtt aag ggc act gag gac tca ggc acc aca gtg ctg ttg ccc      857
Glu Asn Val Lys Gly Thr Glu Asp Ser Gly Thr Thr Val Leu Leu Pro
200                 205                 210                 215 ctg gtc att ttc ttt ggt ctt tgc ctt tta tcc ctc ctc ttc att ggt      905
Leu Val Ile Phe Phe Gly Leu Cys Leu Leu Ser Leu Leu Phe Ile Gly
                220                 225                 230 tta atg tat cgc tac caa cgg tgg aag tcc aag ctc tac tcc att gtt      953
Leu Met Tyr Arg Tyr Gln Arg Trp Lys Ser Lys Leu Tyr Ser Ile Val
        235                 240                 245 tgt ggg aaa tcg aca cct gaa aaa gag ggg gag ctt gaa gga act act     1001
Cys Gly Lys Ser Thr Pro Glu Lys Glu Gly Glu Leu Glu Gly Thr Thr
250                 255                 260 act aag ccc ctg gcc cca aac cca agc ttc agt ccc act cca ggc ttc     1049
Thr Lys Pro Leu Ala Pro Asn Pro Ser Phe Ser Pro Thr Pro Gly Phe
                265                 270                 275 acc ccc acc ctg ggc ttc agt ccc gtg ccc agt tcc acc ttc acc tcc     1097
Thr Pro Thr Leu Gly Phe Ser Pro Val Pro Ser Ser Thr Phe Thr Ser
280                 285                 290                 295 agc tcc acc tat acc ccc ggt gac tgt ccc aac ttt gcg gct ccc cgc     1145
Ser Ser Thr Tyr Thr Pro Gly Asp Cys Pro Asn Phe Ala Ala Pro Arg
                300                 305                 310 aga gag gtg gca cca ccc tat cag ggg gct gac ccc atc ctt gcg aca     1193
Arg Glu Val Ala Pro Pro Tyr Gln Gly Ala Asp Pro Ile Leu Ala Thr
        315                 320                 325 gcc ctc gcc tcc gac ccc atc ccc aac ccc ctt cag aag tgg gag gac     1241
Ala Leu Ala Ser Asp Pro Ile Pro Asn Pro Leu Gln Lys Trp Glu Asp
330                 335                 340 agc gcc cac aag cca cag agc cta gac act gat gac ccc gcg acg ctg     1289
Ser Ala His Lys Pro Gln Ser Leu Asp Thr Asp Asp Pro Ala Thr Leu
345                 350                 355 tac gcc gtg gtg gag aac gtg ccc ccg ttg cgc tgg aag gaa ttc gtg     1337
Tyr Ala Val Val Glu Asn Val Pro Pro Leu Arg Trp Lys Glu Phe Val
360                 365                 370                 375 cgg cgc cta ggg ctg agc gac cac gag atc gat cgg ctg gag ctg cag     1385
Arg Arg Leu Gly Leu Ser Asp His Glu Ile Asp Arg Leu Glu Leu Gln
                380                 385                 390 aac ggg cgc tgc ctg cgc gag gcg caa tac agc atg ctg gcg acc tgg     1433
Asn Gly Arg Cys Leu Arg Glu Ala Gln Tyr Ser Met Leu Ala Thr Trp
        395                 400                 405 agg cgg cgc acg ccg cgg cgc gag gcc acg ctg gag ctg ctg gga cgc     1481
Arg Arg Arg Thr Pro Arg Arg Glu Ala Thr Leu Glu Leu Leu Gly Arg
```

-continued

```
            410                 415                 420
gtg ctc cgc gac atg gac ctg ctg ggc tgc ctg gag gac atc gag gag   1529
Val Leu Arg Asp Met Asp Leu Leu Gly Cys Leu Glu Asp Ile Glu Glu
    425                 430                 435 gcg ctt tgc ggc ccc gcc gcc ctc ccg ccc gcg ccc agt ctt ctc aga   1577
Ala Leu Cys Gly Pro Ala Ala Leu Pro Pro Ala Pro Ser Leu Leu Arg
440                 445                 450                 455 tgaggctgcg cccctgcggg cagctctaag gaccgtcctg cgagatcgcc ttccaacccc   1637
acttttttct ggaaaggagg ggtcctgcag gggcaagcag gagctagcag ccgcctactt   1697
ggtgctaacc cctcgatgta catagctttt ctcagctgcc tgcgcgccgc cgacagtcag   1757
cgctgtgcgc gcggagagag gtgcgccgtg ggctcaagag cctgagtggg tggtttgcga   1817
ggatgaggga cgctatgcct catgcccgtt ttgggtgtcc tcaccagcaa ggctgctcgg   1877
gggcccctgg ttcgtccctg agcctttttc acagtgcata agcagttttt tttgttttg    1937 ttttgttttg ttttgttttt aaatcaatca tgttacacta atagaaactt ggcactcctg   1997
tgccctctgc ctggacaagc acatagcaag ctgaactgtc ctaaggcagg ggcgagcacg   2057
gaacaatggg gccttcagct ggagctgtgg acttttgtac atacactaaa attctgaagt   2117
taaaaaaaaa aaaaaaagga attc                                         2141
```

<210> SEQ ID NO 27
<211> LENGTH: 455
<212> TYPE: PRT
<213> ORGANISM: Artificial Sequence
<220> FEATURE:
<223> OTHER INFORMATION: Description of Artificial Sequence: human TNF-R
      in lTNF-R2

<400> SEQUENCE: 27

```
Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
                 20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205
```

```
Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
                355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: N-terminal
      amino acid sequence of protein purified from urine
      (main sequence)
<221> NAME/KEY: UNSURE
<222> LOCATION: (4)
<223> OTHER INFORMATION: identity of "Xaa" could not be determined

<400> SEQUENCE: 28

Asp Ser Val Xaa Pro Gln Gly Lys Tyr Ile His Pro Gln
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: N-terminal
      amino acid sequence of protein purified from urine
      (subsidiary sequence)
<221> NAME/KEY: UNSURE
<222> LOCATION: (7)
<223> OTHER INFORMATION: identity of "Xaa" could not be determined
```

-continued

<400> SEQUENCE: 29

Leu Val Pro His Leu Gly Xaa Arg Glu
1               5

<210> SEQ ID NO 30
<211> LENGTH: 151
<212> TYPE: DNA
<213> ORGANISM: Homo sapiens

<400> SEQUENCE: 30 cagggaaaa tattcaccct caaataattc gatttgctgt accaagtgcc acaaggaaaa      60
ctacttgtac aatgactgtc caggcccggg gcaggatacg gactgcaggg agtgtgagag    120
cggctccttc acagcctcag aaaacaacaa g                                   151

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 31

Asp Ser Val Cys Pro Gln Gly Lys
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (1)..(2)
<223> OTHER INFORMATION: identity of "Xaa" could not be determined

<400> SEQUENCE: 32

Xaa Xaa Leu Ser Cys Ser Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 33

Asp Thr Val Cys Gly Cys Arg
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 34

Glu Asn Glu Cys Val Ser Cys Ser Asn Cys Lys
1               5                   10

```
<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 35

Glu Asn Glu Cys Val Ser Cys Ser Asn Cys Lys Lys
  1               5                  10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (6)
<223> OTHER INFORMATION: identity of "Xaa" could not be determined
<221> NAME/KEY: UNSURE
<222> LOCATION: (10)..(12)
<223> OTHER INFORMATION: identity of "Xaa" could not be determined

<400> SEQUENCE: 36

Tyr Ile His Pro Gln Xaa Asn Ser Ile Xaa Xaa Xaa Lys
  1               5                  10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 37

Glu Cys Glu Ser Gly Ser Phe Thr Ala Ser Glu Asn Asn Lys
  1               5                  10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 38

Leu Val Pro His Leu Gly Asp Arg
  1               5

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 39

Lys Glu Met Gly Gln Val Glu Ile Ser Ser Cys Thr Val Asp Arg
  1               5                  10                  15

<210> SEQ ID NO 40
<211> LENGTH: 13
```

```
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 40

Gly Thr Tyr Leu Tyr Asn Asp Cys Pro Gly Pro Gly Gln
  1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (9)..(11)
<223> OTHER INFORMATION: identity of "Xaa" could not be determined

<400> SEQUENCE: 41

Glu Met Gly Gln Val Glu Ile Ser Xaa Xaa Xaa Val Asp
  1               5                  10

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 42

Lys Glu Met Gly Gln Val Glu Ile Ser Ser Cys Thr Val Asp Arg Asp
  1               5                  10                  15

Thr Val Cys Gly
           20

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (6)
<223> OTHER INFORMATION: indentity of "Xaa" could not be determined
<221> NAME/KEY: UNSURE
<222> LOCATION: (18)
<223> OTHER INFORMATION: identity of "Xaa" could not be determined

<400> SEQUENCE: 43

Tyr Ile His Pro Gln Xaa Asn Ser Ile Cys Cys Thr Lys Cys His Lys
  1               5                  10                  15

Gly Xaa Tyr

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (16)..(17)
<223> OTHER INFORMATION: identity of "Xaa" could not be determined
```

```
<400> SEQUENCE: 44

Gly Thr Tyr Leu Tyr Asn Asp Cys Pro Gly Pro Gly Gln Asp Thr Xaa
 1               5                  10                  15

Xaa Arg

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 45

Leu Cys Leu Pro Gln Ile Glu Asn
 1               5

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: TNF-BP
      tryptic cleavage peptide
<221> NAME/KEY: UNSURE
<222> LOCATION: (7)
<223> OTHER INFORMATION: identity of "Xaa" could not be determined

<400> SEQUENCE: 46

Gln Asn Thr Val Cys Thr Xaa His Ala Gly Phe Phe Leu Arg
 1               5                  10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 47

Ser Leu Glu Cys Thr Lys Leu Cys Leu Pro Gln Ile Glu Asn
 1               5                  10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 48

Asp Ser Val Cys Pro Gln Gly Lys Tyr Ile His Pro Gln
 1               5                  10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 49

Gln Gly Lys Tyr Ile His Pro
 1               5
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 50
caaggtaaat atattcatcc                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 51
cagggtaagt acatccatcc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 52
caaggtaaat atatacatcc                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 53
caaggcaaat atattcatcc                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 54
cagggcaagt acatccaccc                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 55
caaggcaaat atatacatcc                                               20
```

```
<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 56
caaggaaaat atattcatcc                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 57
cagggaaagt acatccaccc                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 58
caaggaaaat atatacatcc                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 59
caagggaaat atattcatcc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 60 cagggggaagt acatccaccc                                             20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:
      hybridization probe

<400> SEQUENCE: 61
caagggaaat atatacatcc                                              20
```

```
<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 62

Glu Cys Gly Ser Gly Ser Phe Thr Ala Ser Glu Asn Asn Lys
 1               5                  10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 63

Glu Cys Gly Ser Gly Ser Phe Thr Ala Ser Cys Asn Asn Lys
 1               5                  10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 64

Phe Thr Ala Ser Glu Asn Asn Lys
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: TNF-BP
      tryptic cleavage peptide

<400> SEQUENCE: 65

Phe Thr Ala Ser Cys Asn Asn Lys
 1               5

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 66
aaatgacgga gactcttgtt gttcctaggg                                    30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 67
```
aagtggcgta gtcttttgtt gttcctaggg     30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 68
aaatgtcgga gactcttgtt gttcctaggg     30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 69
aaatgacggt cactcttgtt gttcctaggg     30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 70
aagtggcgtt ctcttttgtt gttcctaggg     30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 71
aaatgtcggt cactcttgtt gttcctaggg     30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 72
aaatgacgga gaacattgtt gttcctaggg     30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 73
aagtggcgta gtactttgtt gttcctaggg     30

```
<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 74
aaatgtcgga gaacattgtt gttcctaggg                                30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 75
aaatgacggt caacattgtt gttcctaggg                                30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 76
aagtggcgtt ctactttgtt gttcctaggg                                30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence:
      hybridization probe

<400> SEQUENCE: 77
aaatgtcggt caacattgtt gttcctaggg                                30

<210> SEQ ID NO 78
<211> LENGTH: 158
<212> TYPE: DNA
<213> ORGANISM: Homo sapiens
<220> FEATURE:
<221> NAME/KEY: CDS
<222> LOCATION: (1)..(153)

<400> SEQUENCE: 78 cag ggg aaa tat att cac cct caa aat aat tcg att tcg tgt acc aag        48
Gln Gly Lys Tyr Ile His Pro Gln Asn Asn Ser Ile Ser Cys Thr Lys
  1               5                  10                  15 tcg cac aaa gga acc tac ttg tac aat gac tgt cca ggc ccg ggg cag        96
Ser His Lys Gly Thr Tyr Leu Tyr Asn Asp Cys Pro Gly Pro Gly Gln
             20                  25                  30 gat acg gac tgc agg gag tgt gag agc ggc tcc ttc aca gcc tca gaa       144
Asp Thr Asp Cys Arg Glu Cys Glu Ser Gly Ser Phe Thr Ala Ser Glu
         35                  40                  45 aac aac aag gatcc                                                    158
Asn Asn Lys
         50
```

<210> SEQ ID NO 79
<211> LENGTH: 51
<212> TYPE: PRT
<213> ORGANISM: Homo sapiens

<400> SEQUENCE: 79

Gln Gly Lys Tyr Ile His Pro Gln Asn Asn Ser Ile Ser Cys Thr Lys
 1               5                  10                  15

Ser His Lys Gly Thr Tyr Leu Tyr Asn Asp Cys Pro Gly Pro Gly Gln
             20                  25                  30

Asp Thr Asp Cys Arg Glu Cys Glu Ser Gly Ser Phe Thr Ala Ser Glu
         35                  40                  45

Asn Asn Lys
     50

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: PCR primer
      EBI-1786

<400> SEQUENCE: 80
ggaattcagc ctgaatggcg aatggg                                    26

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: PCR primer
      EBI-1729

<400> SEQUENCE: 81
cctcgagcgt tgctggcgtt tttcc                                     25

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: PCR primer
      EBI-1733

<400> SEQUENCE: 82
ggtcgacatt gattattgac tag                                       23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: PCR primer
      EBI-1734

<400> SEQUENCE: 83
ggaattccct aggaatacag cgg                                       23

<210> SEQ ID NO 84
<211> LENGTH: 19
<212> TYPE: DNA
<213> ORGANISM: Artificial Sequence
<220> FEATURE:

<223> OTHER INFORMATION: Description of Artificial Sequence: mutagenesis
      primer EBI-1751

<400> SEQUENCE: 84
gtacttgaac tcgttcctg                                                    19

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: mutagenesis
      primer EBI-1857

<400> SEQUENCE: 85
ggcaagggca gcagccgg                                                     18

<210> SEQ ID NO 86
<211> LENGTH: 53
<212> TYPE: DNA
<213> ORGANISM: Artificial Sequence
<220> FEATURE:
<223> OTHER INFORMATION: Description of Artificial Sequence:
      oligonucleotide EBI-1823

<400> SEQUENCE: 86
agcttctgca ggtcgacatc gatggatcgg tacctcgagc ggccgcgaat tct              53

<210> SEQ ID NO 87
<211> LENGTH: 54
<212> TYPE: DNA
<213> ORGANISM: Artificial Sequence
<220> FEATURE:
<223> OTHER INFORMATION: Description of Artificial Sequence:
      oligonucleotide EBI-1829

<400> SEQUENCE: 87
ctagagaatt cgcggccgct cgaggtaccg gatccatcga tgtcgacctg caga             54

<210> SEQ ID NO 88
<211> LENGTH: 63
<212> TYPE: DNA
<213> ORGANISM: Artificial Sequence
<220> FEATURE:
<223> OTHER INFORMATION: Description of Artificial Sequence:
      oligonucleotide EBI-1820

<400> SEQUENCE: 88
agctctagag attcgcggcc gctcgaggta ccggatccat cgatgtcgac ctgcagaagc       60
ttg                                                                     63

<210> SEQ ID NO 89
<211> LENGTH: 64
<212> TYPE: DNA
<213> ORGANISM: Artificial Sequence
<220> FEATURE:
<223> OTHER INFORMATION: Description of Artificial Sequence:
      oligonucleotide EBI-1821

<400> SEQUENCE: 89
ctagcaagct tctgcaggtc gacatcgatg gatccggtac ctcgagcggc cgcgaattct       60
ctag                                                                    64

<210> SEQ ID NO 90
<211> LENGTH: 25

```
<212> TYPE: DNA
<213> ORGANISM: Artificial Sequence
<220> FEATURE:
<223> OTHER INFORMATION: Description of Artificial Sequence: PCR primer
      EBI-1986

<400> SEQUENCE: 90
caggatccga gtctcaaccc tcaac                                          25

<210> SEQ ID NO 91
<211> LENGTH: 43
<212> TYPE: DNA
<213> ORGANISM: Artificial Sequence
<220> FEATURE:
<223> OTHER INFORMATION: Description of Artificial Sequence: PCR primer
      EBI-1929

<400> SEQUENCE: 91
gggaattcct tatcaattct caatctgggg taggcacaac ttc                      43

<210> SEQ ID NO 92
<211> LENGTH: 81
<212> TYPE: DNA
<213> ORGANISM: Artificial Sequence
<220> FEATURE:
<223> OTHER INFORMATION: Description of Artificial Sequence: PCR primer
      EBI-2452

<400> SEQUENCE: 92
cacagtcgac ttacatttgc ttctgacaca actgtgttca ctagcaacct caaacagaca    60
ccatgggcct ctccaccgtg c                                              81

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: PCR primer
      EBI-1922

<400> SEQUENCE: 93
gaggctgcaa ttgaagc                                                   17

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: PCR primer
      EBI-2316

<400> SEQUENCE: 94
attcgtgcgg cgcctag                                                   17

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: PCR primer
      EBI-2467

<400> SEQUENCE: 95
gtcggtagca ccaagga                                                   17

<210> SEQ ID NO 96
```

-continued

```
<211> LENGTH: 17
<212> TYPE: DNA
<213> ORGANISM: Artificial Sequence
<220> FEATURE:
<223> OTHER INFORMATION: Description of Artificial Sequence: M13-40
      universal primer

<400> SEQUENCE: 96
gttttcccag tcacgac                                                17

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence:  PCR primer
      EBI-2112

<400> SEQUENCE: 97
gtccaattat gtcacacc                                               18
```

The invention claimed is:

1. An isolated nucleic acid molecule comprising the nucleotide sequence as set forth in SEQ ID NO: 3, wherein the isolated nucleic acid molecule does not further comprise residues 88-120 or residues 604-633 of the nucleotide sequence of SEQ ID NO: 1.

2. A vector comprising the nucleic acid molecule of claim 1.

3. An isolated nucleic acid molecule encoding a polypeptide having the ability to bind TNF, wherein said polypeptide comprises the amino acid sequence as set forth in SEQ ID NO: 4, and wherein said polypeptide does not comprise residues 30-40 or 202-211 of the amino acid sequence set forth in SEQ ID NO: 2.

4. The isolated nucleic acid molecule of claim 3, wherein said polypeptide further comprises an amino-terminal methionine.

5. A vector comprising the nucleic acid molecule of claim 4.

6. The nucleic acid molecule of claim 3, wherein said nucleic acid molecule encodes a polypeptide having at least one additional amino acid at the amino-terminus, at the carboxyl-terminus, or at both the amino-terminus and the carboxyl-terminus.

7. The nucleic acid of claim 6, wherein said nucleic acid molecule encodes a polypeptide having at least one additional amino acid at the amino-terminus.

8. The nucleic acid of claim 7, wherein said nucleic acid molecule encodes a polypeptide having a methionine at the amino-terminus.

9. The nucleic acid of claim 6, wherein said nucleic acid molecule encodes a polypeptide having at least one additional amino acid at the carboxyl-terminus.

10. A vector comprising the nucleic acid molecule of claim 3.

11. An isolated nucleic acid molecule encoding a polypeptide having the ability to bind TNF, wherein said polypeptide consists of the amino acid sequence of SEQ ID NO: 4 and an amino-terminal methionine.

12. A vector comprising the nucleic acid molecule of claim 11.

13. A process of producing a recombinant polypeptide having the ability to bind TNF comprising culturing a host cell comprising a nucleic acid molecule that encodes a polypeptide consisting of the amino acid sequence of SEQ ID NO: 4 and an amino-terminal methionine under suitable conditions to express the polypeptide.

n

* * * * *